(12) United States Patent
Schulz-Gasch et al.

(10) Patent No.: US 9,359,351 B2
(45) Date of Patent: Jun. 7, 2016

(54) CAP/ENDO DUAL INHIBITORS AND THEIR USE IN THE TREATMENT, AMELIORATION OR PREVENTION OF A VIRAL DISEASE

(71) Applicants: F. Hoffmann-La Roche AG, Basel (CH); Savira pharmaceuticals GmbH, Vienna (CH); European Molecular Biology Laboratory, Heidelberg (DE)

(72) Inventors: Tanja Schulz-Gasch, Ziefen (CH); Robert Weikert, Basel (CH); Werner Neidhart, Hagenthal-le-Bas (FR); Helmut Buschmann, Aachen (DE); Oliver Szolar, Vienna (AT); Andrea Wolkerstorfer, Vienna (AT); Norbert Handler, Vienna (AT); Franz-Ferdinand Roch, Vienna (AT); Stephen Cusack, Seyssinet-Pariset (FR)

(73) Assignees: F. Hoffmann-La Roche AG, Basel (CH); Savira pharmaceuticals GmbH, Vienna (AT); European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 14/793,699
(22) Filed: Jul. 7, 2015

(65) Prior Publication Data

US 2016/0002227 A1 Jan. 7, 2016

Related U.S. Application Data

(60) Provisional application No. 62/021,590, filed on Jul. 7, 2014.

(51) Int. Cl.
| | |
|---|---|
| C07D 471/04 | (2006.01) |
| A61K 31/4985 | (2006.01) |
| A61K 45/06 | (2006.01) |
| A61K 31/506 | (2006.01) |
| C07D 519/00 | (2006.01) |

(52) U.S. Cl.
CPC .......... *C07D 471/04* (2013.01); *A61K 31/4985* (2013.01); *A61K 31/506* (2013.01); *A61K 45/06* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 2006/0052361 | A1* | 3/2006 | Miyazaki | C07D 487/04 514/211.04 |
| 2007/0161639 | A1* | 7/2007 | Jones | C07D 471/04 514/249 |
| 2014/0328793 | A1* | 11/2014 | Gavegnano | A61K 31/52 424/85.2 |

FOREIGN PATENT DOCUMENTS

| | | | |
|---|---|---|---|
| WO | 2006066414 | * | 12/2005 |
| WO | 2006/066414 A1 | | 6/2006 |
| WO | 2014172188 | * | 10/2014 |

OTHER PUBLICATIONS

International Search Report and the Written Opinion of the International Searching Authority, Oct. 22, 2015, for International Application No. PCT/EP2015/065365.

*Primary Examiner* — Karl J Puttlitz
(74) *Attorney, Agent, or Firm* — Mintz Levin Cohn Ferris Glovsky and Popeo, P.C.

(57) ABSTRACT

The present invention relates to a compound having the general formula (V), optionally in the form of a pharmaceutically acceptable salt, solvate, polymorph, codrug, cocrystal, prodrug, tautomer, racemate, enantiomer, or diastereomer or mixture thereof,

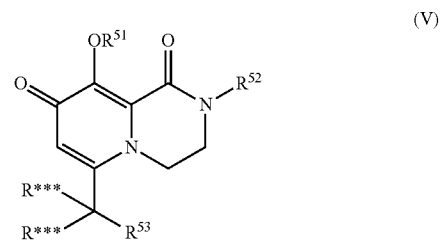

(V)

which are useful in treating, ameliorating or preventing a viral disease. Furthermore, specific combination therapies are disclosed.

19 Claims, 1 Drawing Sheet

```
capped primer   1       7
5'- gggggaaauacucaagagcaaa  agcagguagauaaucaucacugag  ugacaucaaaaucAUGgcgucc -3'
3'- cccccuuauagguucucguuu   [tcgtccatcattagtgagtgactc]                          -5'
                            LE1                        [actgtagtttagtaccgcagg]
                                                       CE1
                            33       start codon NP 55                          76                         100
5'- caaggcaccaaacggucuuac   gaacagaugggagaugauggagaa  cgccagaaugccacugaa     -3'
3'- [gttctgtggtttgccagaatg] [cttgtctacctctgactaccctt]                          -5'
    BP2                     CE2                       [gcggtcttaccggtgactt]
                                                      CE3

119                         139                        160
5'- ucagagcauccgucggaaaa    augauuggugaauuggacga      uucuacauccaaaugugcacagaa -3'
3'- [agtctcgtaggcagccttt]   [tactaaccacttaacctgct]                              -5'
    CE4                     BP3                       [aagatgtagtttacacgtgtctt]
                                                      BP4

184                         212  1425                 1448
5'- cuuaaacucagugauuaugaggacg...gc ggggagucuucgagcucucg  gccgaaaagcagcgagcc   -3'
3'- [gaattgagtcactaatactccctgc]   [ccctcagaagctcgagagc]                        -5'
    CE5                           CE6                   [ctgcttccgtcgtcggg]
                                                        CE7

1467                        1487                       1514
5'- cgaucgugccuuccuuugac    augaguaaaugaaggauucuuauuucuuc  ggagacaaagcagcagaggaguacg -3'
3'- [gctagcacggaggaactg]    [tactcattactttcctagaataaaag]                                -5'
    CE8                     CE9                           [cctctgttcgtctcctcatgc]
                                                          BP5 stop codon NP               poly A tail
5'- acaauuaaagaaaaaaaaaaaaaaaaaa.... -3'
3'- [tgtgatttttttttttttt]             -5'
    LE2
```

CAP/ENDO DUAL INHIBITORS AND THEIR USE IN THE TREATMENT, AMELIORATION OR PREVENTION OF A VIRAL DISEASE

CROSS-REFERENCE TO RELATED APPLICATIONS

This application claims benefit of U.S. Patent Application Ser. No. 62/021,590, filed on Jul. 7, 2014 which application is incorporated by reference herein in its entirety.

FIELD OF THE INVENTION

The present invention relates to a compound having the general formula (V), optionally in the form of a pharmaceutically acceptable salt, solvate, polymorph, codrug, cocrystal, prodrug, tautomer, racemate, enantiomer, or diastereomer or mixture thereof, (V)

[chemical structure with substituents $OR^{51}$, $R^{52}$, $R^{53}$, $R^{*}$, $R^{*}$]

which is useful in treating, ameliorating or preventing a viral disease. Furthermore, specific combination therapies are disclosed.

INCORPORATION BY REFERENCE OF SEQUENCE LISTING

This application contains references to amino acids and/or nucleic acid sequences that have been filed concurrently herewith as sequence listing text file 0384980.txt, file size of 5.2 KB, created on Jul. 7, 2015. The aforementioned sequence listing is hereby incorporated by reference in its entirety pursuant to 37 C.F.R. §1.52(e)(5).

BACKGROUND OF THE INVENTION

In recent years the serious threat posed by influenza virus infection to worldwide public health has been highlighted by, firstly, the ongoing level transmission to humans of the highly pathogenic avian influenza A virus H5N1 strain (63% mortality in infected humans, http://www.who.int/csr/disease/avian_influenza/en/) and secondly, the unexpected emergence in 2009 of a novel pandemic influenza virus strain A/H1N1 that has rapidly spread around the entire world (http://www.who.int/csr/disease/swineflu/en/). Whilst the new virus strain is highly contagious but currently generally results in relatively mild illness, the future evolution of this virus is unpredictable. In a much more serious, but highly plausible scenario, H5N1 and related highly pathogenic avian influenza viruses could acquire mutations rendering them more easily transmissible between humans or the new A/H1N1 could become more virulent and only a single point mutation would be enough to confer resistance to oseltamivir (Neumann et al., Nature, 2009 (18; 459(7249) 931-939)); as many seasonal H1N1 strains have recently done (Dharan et al., The Journal of the American Medical Association, 2009 Mar. 11; 301 (10), 1034-1041; Moscona et al., The New England Journal of Medicine, 2009 (March 5; 360(10) pp 953-956)). In this case, the delay in generating and deploying a vaccine (~6 months in the relatively favourable case of A/H1N1 and still not a solved problem for H5N1) could have been catastrophically costly in human lives and societal disruption.

It is widely accepted that to bridge the period before a new vaccine is available and to treat severe cases, as well as to counter the problem of viral resistance, a wider choice of anti-influenza drugs is required. Development of new anti-influenza drugs has therefore again become high priority, having been largely abandoned by the major pharmaceutical companies once the neuraminidase inhibitors became available.

An excellent starting point for the development of antiviral medication is structural data of essential viral proteins. Thus, the crystal structure determination of e.g. the influenza virus surface antigen neuraminidase (Von Itzstein, M. et al., (1993), Nature, 363, pp. 418-423) led directly to the development of neuraminidase inhibitors with antiviral activity preventing the release of virus from the cells, however, not the virus production itself. These and their derivatives have subsequently developed into the anti-influenza drugs, zanamivir (Glaxo) and oseltamivir (Roche), which are currently being stockpiled by many countries as a first line of defence against a possible pandemic. However, these medicaments only provide a reduction in the duration of the clinical disease. Alternatively, adamantanes, the other class of licensed anti-influenza drugs (e.g. amantadine and rimantadine) target the viral M2 ion channel protein, which is located in the viral membrane interfering with the uncoating of the virus particle inside the cell. However, they have not been extensively used due to their side effects and the rapid development of resistant virus mutants (Magden, J. et al., (2005), Appl. Microbiol. Biotechnol., 66, pp. 612-621). In addition, more unspecific viral drugs, such as ribavirin, have been shown to work for treatment of influenza and other virus infections (Eriksson, B. et al., (1977), Antimicrob. Agents Chemother., 11, pp. 946-951). However, ribavirin is only approved in a few countries, probably due to severe side effects (Furuta et al., ANTIMICROBIAL AGENTS AND CHEMOTHERAPY, 2005, p. 981-986). Clearly, new antiviral compounds are needed, preferably directed against different targets.

Influenza virus as well as Thogotovirus and isavirus belong to the family of Orthomyxoviridae which, as well as the family of the Bunyaviridae, including the Hantavirus, Nairovirus, Orthobunyavirus, and Phlebovirus, are, amongst others, negative stranded RNA viruses. Their genome is segmented and comes in ribonucleoprotein particles that include the RNA dependent RNA polymerase which carries out (i) the initial copying of the single-stranded negative-sense viral RNA (vRNA) into viral mRNAs (i.e. transcription) and (ii) the vRNA replication. This enzyme, a trimeric complex composed of subunits PA, PB1 and PB2, is central to the life cycle of the virus since it is responsible for the replication and transcription of viral RNA. In previous work the atomic structure of two key domains of the polymerase, the mRNA cap-binding domain in the PB2 subunit (Guilligay et al., Nature Structural & Molecular Biology 2008; May; 15(5): 500-506) and the endonuclease-active site residing within the PA subunit (Dias et al., Nature 2009. 458, 914-918) have been identified and and their molecular architecture has been characterized. These two sites are critical for the unique "cap-snatching" mode used to initiate mRNA transcription that is used by the influenza virus and certain other virus families of this genus to generate viral mRNAs. A 5' cap is a modified guanine nucleotide that has been added to the 5' end of a messenger RNA. The 5' cap (also termed an RNA cap or RNA m7G cap) consists of a terminal 7-methylguanosine residue which is linked through a 5'-5'-triphosphate bond to the first transcribed nucleotide. The viral polymerase binds to the 5' RNA cap of cellular mRNA molecules and cleaves the RNA cap together with a stretch of 10 to 15 nucleotides. The capped RNA fragments then serve as primers for the synthesis of viral mRNA (Plotch, S. J. et al., (1981), Cell, 23, pp. 847-858; Kukkonen, S. K. et al (2005), Arch. Virol., 150, pp. 533-556; Leahy, M. B. et al., (2005), J. Virol., 71, pp. 8347-8351; Noah, D. L. et al., (2005), Adv. Virus Res., 65, pp. 121-145).

The polymerase complex seems to be an appropriate antiviral drug target since it is essential for synthesis of viral mRNA and viral replication and contains several functional active sites likely to be significantly different from those found in host cell proteins (Magden, J. et al., (2005), Appl. Microbiol. Biotechnol., 66, pp. 612-621). Thus, for example, there have been attempts to interfere with the assembly of polymerase subunits by a 25-amino-acid peptide resembling the PA-binding domain within PB1 (Ghanem, A. et al., (2007), J. Virol., 81, pp. 7801-7804). Furthermore, the endonuclease activity of the polymerase has been targeted and a series of 4-substituted 2,4-dioxobutanoic acid compounds has been identified as selective inhibitors of this activity in influenza viruses (Tomassini, J. et al., (1994), Antimicrob. Agents Chemother., 38, pp. 2827-2837). In addition, flutimide, a substituted 2,6-diketopiperazine, identified in extracts of *Delitschia confertaspora*, a fungal species, has been shown to inhibit the endonuclease of influenza virus (Tomassini, J. et al., (1996), Antimicrob. Agents Chemother., 40, pp. 1189-1193). Moreover, there have been attempts to interfere with viral transcription by nucleoside analogs, such as 2'-deoxy-2'-fluoroguanosine (Tisdale, M. et al., (1995), Antimicrob. Agents Chemother., 39, pp. 2454-2458).

WO 2006/066414 relates to certain hydroxydihydropyridopyrazine-1,8-diones which are stated to be suitable for inhibiting HIV integrase.

EP-A-1 544 199 discloses specific nitrogenous condensed-ring compounds which are described as HIV integrase inhibitors.

It is an object of the present invention to identify further compounds which are effective against viral diseases and which have improved pharmacological properties.

SHORT DESCRIPTION OF THE FIGURE

FIG. 1

Sequence of the de novo synthesized viral mRNA used for Quantigene TA assay probe set design: Label Extenders (LE) hybridize to the capped primer sequence derived from provided synthetic RNA substrate and first bases of the de novo synthesized viral mRNA at the 5'-end (LE1), and to the poly a tail at the 3'-end (LE2). Capture Extenders (CE1-9) specifically hybridize to gene specific regions and concomitantly immobilize the captured RNA to the plate. Blocking Probes (BP) hybridize to different stretches of the de novo synthesized viral mRNA. The sequence shown in italics at the 3'-end was verified by 3'-RLM RACE (not complete sequence shown). The probe sets are supplied as a mix of all three by Panomics.

SUMMARY OF THE INVENTION

Accordingly, in a first embodiment, the present invention provides a compound having the general formula (V).

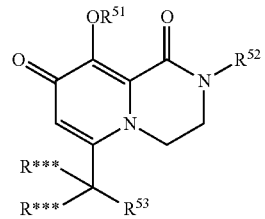

It is understood that throughout the present specification the term "a compound having the general formula (V)" encompasses pharmaceutically acceptable salts, solvates, polymorphs, prodrugs, codrugs, cocrystals, tautomers, racemates, enantiomers, or diastereomers or mixtures thereof unless mentioned otherwise.

A further embodiment of the present invention relates to a pharmaceutical composition comprising a compound having the general formula (V) and optionally one or more pharmaceutically acceptable excipient(s) and/or carrier(s).

The compounds having the general formula (V) are useful for treating, ameliorating or preventing viral diseases.

It has been surprisingly found that the compounds according to the present invention provide a combination of cap-binding and endonuclease fragments via a linker system (butterfly conformation) using the optimal connectivity and substitution pattern of the cap-binding and endonuclease cores. This approach provides chemical and metabolic stability under consideration of tolerated drug-like properties and translates the linker strategy to a hybrid approach since both core fragments are connected but replace respective relevant parts of the selective ligands.

In the current compounds, the bimetal binding head group as a bicyclic ring system is connected with a bulky hydrophobic group providing additional interaction important for increasing ligand efficiency and selectivity for the influenza polymerase to obtain selective and in vivo potent compounds superior to currently available treatment options. As hydrophobic groups, a broad variation of different aromatic ring systems is tolerated to optimize the binding affinity with additional functionalities. The connecting linker group between the bimetal head functionality and the hydrophobic substituent ensures the optimal spatial arrangement of both fragments and also influences the overall polarity of the molecule determining the cellular permeability. The cap-fragment of the present compounds ensures an optimal planar core providing the significant π-stacking interactions within the flat cap-binding pocket.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "alkyl" refers to a saturated straight or branched hydrocarbon chain.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "bicyclic fused ring system comprising from 10 to 14 ring atoms and 1 to 4 nitrogen atoms" refers to a ring system which includes at least two rings which are fused together, i.e., share a bond. The rings constituting the ring system can be saturated, unsaturated or aromatic. Typical examples are ring systems in which two rings having 5, 6, or 7 ring atoms are fused together. In the bicyclic fused ring system employed in compounds of the present invention 1 to 4 of the ring atoms are nitrogen atoms. In addition, the bicyclic fused ring system can be substituted by carbonyl groups (=O) or other substituents as defined in the appended claims.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

The term "carbocyclyl" covers any five- or six-membered hydrocarbon ring which does not include heteroatoms in the ring. The term "carbocyclyl ring" covers saturated (including cycloalkyl rings), unsaturated rings and aromatic rings (including aryl rings).

"Hal" or "halogen" represents F, Cl, Br and I.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, pyrazole, oxazolidine, oxazole, thiazole, piperidine, pyridine, morpholine, piperazine, and dioxolane.

The term "heterocyclyl" covers any five- or six-membered ring wherein at least one of the carbon atoms in the ring has been replaced by 1, 2, 3, or 4 (for the five-membered ring) or 1, 2, 3, 4, or 5 (for the six-membered ring) of the same or different heteroatoms, whereby the heteroatoms are selected from O, N and S. The term "heterocyclyl ring" covers saturated, unsaturated rings and aromatic rings (including heteroaryl rings). Examples include pyrrole, pyrrolidine, oxolane, furan, imidazolidine, imidazole, pyrazole, oxazolidine, oxazole, thiazole, piperidine, pyridine, morpholine, piperazine, and dioxolane.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups. Preferred examples of the prodrug include compounds in which $R^{51}$ is selected from —C(O)—R, —C(O)—OR, —PO(OR$^A$)(OR$^B$) or —OC(O)OR, in which R, $R^A$ and $R^B$ are independently selected from $C_{1-6}$ alkyl, aryl, or heteroaryl, whereby the alkyl, aryl, or heteroaryl can be optionally substituted, e.g., by —OH or O—$C_{1-6}$alkyl. Examples of R include $C_{1-6}$ alkyl (CH$_3$, t-butyl), phenyl, phenyl-OH or phenyl-OCH$_3$.

Compounds Having the General Formula (V)

The present invention provides a compound having the general formula (V).

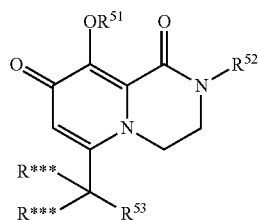

The present invention provides a compound having the general formula (V) in which the following definitions apply.

$R^{51}$ is selected from —H, -(optionally substituted $C_{1-6}$ alkyl) and —C(O)-(optionally substituted $C_{1-6}$ alkyl); preferably $R^{51}$ is selected from —H and —$C_{1-6}$ alkyl; more preferably $R^{51}$ is —H.

$R^{52}$ is selected from —H, -(optionally substituted $C_{1-6}$ alkyl), —(CH$_2$)$_q$-(optionally substituted heterocyclyl), —(CH$_2$)$_q$-(optionally substituted carbocyclyl), —(CH$_2$)$_p$—OR$^{55}$, and —(CH$_2$)$_p$—NR$^{56}$R$^{57}$; preferably $R^{52}$ is selected from —H and —$C_{1-6}$ alkyl.

$R^{53}$ is selected from —$R^{54}$ and —$X^{51}R^{54}$; preferably $R^{53}$ is —$X^{51}R^{54}$.

$R^{54}$ is a bicyclic fused ring system comprising from 10 to 14 ring atoms and 1 to 4 nitrogen atoms as ring atoms, wherein the bicyclic fused ring system can optionally be substituted. Preferably $R^{54}$ is a bicyclic fused ring system comprising two fused rings, wherein the fused rings are independently selected from 5-membered rings, 6-membered rings and 7-membered rings. More preferably $R^{54}$ is a bicyclic fused ring system comprising two fused rings, wherein the fused rings are independently selected from 5-membered rings and 6-membered rings, particularly $R^{54}$ is a bicyclic fused ring system comprising two fused rings, wherein the fused rings are a 5-membered ring and a 6-membered ring. The bicyclic fused ring system comprises 1 to 4 nitrogen atoms, preferably 2 to 3 nitrogen atoms.

The bicyclic fused ring system can be optionally substituted with one or more (e.g., 1, 2 or 3) substituents which are independently selected from (=O), halogen, —CN, —CF$_3$, —(CH$_2$)$_s$—X$^{52}$—R$^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms). Preferred substituents in this respect are (=O), halogen, —CN, —CF$_3$, and —$C_{3-7}$ carbocyclyl, more preferably one or more substituents selected from (=O), halogen and —$C_{3-7}$ carbocyclyl, even more preferably (=O) and halogen.

In a preferred embodiment, $R^{54}$ is selected from the group consisting of

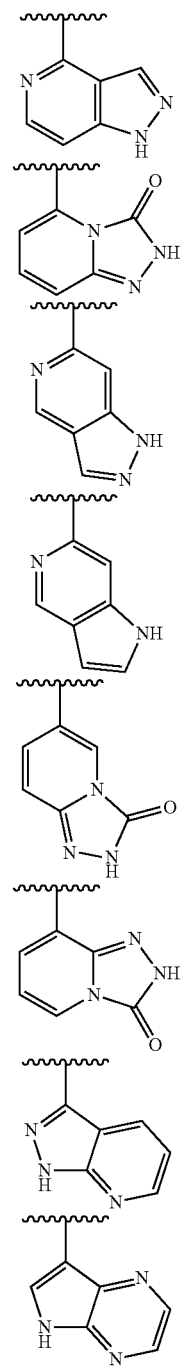

wherein

⁓⁓⁓ indicates the point of attachment to the remainder of the molecule; and wherein the group can be optionally substituted with one or more substituents selected from halogen, —CN, —CF$_3$, —(CH$_2$)$_s$—X$^{52}$—R$^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms), preferably one or more substituents selected from halogen, —CN, —$CF_3$, and —$C_{3-7}$ carbocyclyl, more preferably one or more substituents selected from halogen and —$C_{3-7}$ carbocyclyl, even more preferably halogen.

$R^{55}$ is selected from —H, —$C_{1-6}$ alkyl, and —$(CH_2CH_2O)_rH$.

$R^{56}$ is selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); preferably —H, and -(optionally substituted $C_{1-6}$ alkyl), more preferably —H and —$C_{1-6}$ alkyl.

$R^{57}$ is selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); preferably —H, and -(optionally substituted $C_{1-6}$ alkyl); more preferably —H and —$C_{1-6}$ alkyl.

$R^{58}$ is selected from —H and —$C_{1-6}$ alkyl.

$X^{51}$ is selected from -$L_1$-(A-($L_2$)$_m$)$_n$-; preferably $X^{51}$ is selected from -$L_1$- and -$L_1$-A-$L_2$-.

$X^{52}$ is selected from $NR^{56}$, $N(R^{56})C(O)$, $C(O)NR^{56}$, O, C(O), C(O)O, OC(O); $N(R^{56})SO_2$, $SO_2N(R^{56})$, S, SO, and $SO_2$; preferably $X^{52}$ is selected from $N(R^{56})C(O)$, $C(O)NR^{56}$, $N(R^{56})SO_2$, and $SO_2N(R^{56})$.

$L_1$ is selected from $NR^{56}$, $N(R^{56})C(O)$, $C(O)NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$; preferably $L_1$ is selected from $NR^{56}$, $N(R^{56})C(O)$, $C(O)NR^{56}$, C(O)O, OC(O), O and (optionally substituted heterocyclyl having 3 to 7 ring atoms)-$NR^{56}$. One example is

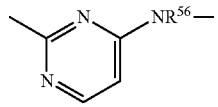

which can be optionally substituted, e.g., by halogen such as F.

$L_2$ is selected from $NR^{56}$, $N(R^{56})C(O)$, $C(O)NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$; preferably $L_2$ is selected from $NR^{56}$, $N(R^{56})C(O)$, $C(O)NR^{56}$, C(O)O, OC(O), O and (optionally substituted heterocyclyl having 3 to 7 ring atoms)-$NR^{56}$. One example is

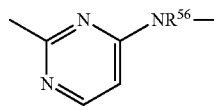

which can be optionally substituted, e.g., by halogen such as F.

A is selected from $(CR*R**)_t$, optionally substituted $C_{3-7}$ carbocyclyl, optionally substituted heterocyclyl having 3 to 7 ring atoms, wherein at least one (e.g., 1, 2 or 3) of the ring atoms of the carbocyclyl or the heterocyclyl is bonded in chain with the moieties $L_1$ and $L_2$ or $R^{54}$, respectively.

Combinations of two or more moieties A can also be present. For instance, two moieties A can be covalently bonded to each other to provide a moiety -$L_1$-(A-A-($L_2$)$_m$)$_n$-. In one option, A can be selected from $(CR*R**)_t$, cyclohexyl and phenyl and combinations thereof. Examples of $(CR*R**)_t$ include —$(CH_2)_t$—, and —$(CHR*)_t$—.

R* is independently for each occurrence selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); preferably R* is independently for each occurrence selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); more preferably —H, —($C_{1-6}$ alkyl), -(optionally substituted $C_{3-7}$ carbocyclyl), and —$C_{1-4}$ alkyl-(optionally substituted $C_{3-7}$ carbocyclyl).

R is independently for each occurrence selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); preferably R is independently for each occurrence selected from —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms); more preferably —H, —($C_{1-6}$ alkyl), -(optionally substituted $C_{3-7}$ carbocyclyl), and —$C_{1-4}$ alkyl-(optionally substituted $C_{3-7}$ carbocyclyl).

In an alternative embodiment, R* and R** together with the carbon atom to which they are attached form an optionally substituted $C_{3-7}$ carbocyclyl group or optionally substituted heterocyclyl group having 3 to 7 ring atoms, preferably an optionally substituted $C_{3-7}$ carbocyclyl group.

R*** is independently for each occurrence —H, a —$C_{1-6}$ alkyl group, or a —$C_{1-6}$ alkyl group which is substituted by one or more halogen atoms.

m is 0 or 1.
n is 0 or 1.
p is 1 to 4.
q is 0 to 4.
r is 1 to 3.
s is 0 to 4.
t is 1 to 6.

The alkyl group can be optionally substituted with one or more substituents which are independently selected from halogen, —CN, —$NR^{56}R^{57}$, —OH, and —O—$C_{1-6}$ alkyl.

The hydrocarbon group, heterocyclyl group, and/or carbocyclyl group can be optionally substituted with one or more substituents which are independently selected from halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms); preferably halogen, —CN, —$NR^{56}R^{57}$, —OH, and —O—$C_{1-6}$ alkyl.

All combinations of the above definitions and preferred definitions are also envisaged by the present inventors.

The present inventors have surprisingly found that the compounds of the present invention which have a specific linker —$(CR*R*)$—$R^{53}$ have improved pharmacological properties compared to corresponding compounds which do not have such a linker. Without wishing to be bound by theory it is assumed that the present compounds do not only offer bimetal binding but also hydrophobic interaction which contributes to the intrinsic binding properties of the ligands. A more flexible linker combining the bimetal head group with a bulky hydrophobic substituent gives a higher conformational flexibility providing the right vectors to adapt to the specific interaction and to interact in a more optimal way to several amino acids of the binding pocket by a higher conformational flexibility without loosing entropic contributions (one molecule).

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a caplet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;

b) lubricants such as magnesium stearate, talc, calcium stearate, zinc stearate, stearic acid, hydrogenated vegetable oil, leucine, glycerids and sodium stearyl fumarates, c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatine, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous.

Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxviridae, Herpesviridae, Adenoviridae, Papillomaviridae, Polyomaviridae, Parvoviridae, Hepadnaviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
|---|---|
| Poxviridae | Smallpox virus |
| | Molluscum contagiosum virus |
| Herpesviridae | Herpes simplex virus |
| | Varicella zoster virus |
| | Cytomegalo virus |
| | Epstein Barr virus |
| | Kaposi's sarcoma-associated herpes virus |
| Adenoviridae | Human adenovirus A-F |
| Papillomaviridae | Papilloma virus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxovirida | eInfluenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean-Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |
| | Machupo virus |
| | Sabia virus |
| Coronaviridae | Human coronavirus |
| Picornaviridae | Human enterovirus types A-D (Poliovirus, Echovirus, Coxsackie virus NB) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |
| Deltavirus | Hepatitis deltavirus |
| Bornaviridae | Bornavirus |
| | Prions |

Preferably, the compounds of the present invention are employed to treat influenza. The present invention covers all virus genera belonging to the family of orthomyxoviridae, specifically influenza virus type A, B, and C, isavirus, and thogotovirus. Within the present invention, the term "influenza" includes influenza caused by any influenza virus such as influenza virus type A, B, and C including their various stains and isolates, and also covers influenza A virus strains commonly referred to as bird flu and swine flu. The subject to be treated is not particularly restricted and can be any vertebrate, such as birds and mammals (including humans).

Without wishing to be bound by theory, it is assumed that the compounds of the present invention are capable of inhibiting endonuclease activity, particularly that of influenza virus. More specifically it is assumed that they directly interfere with the N-terminal part of the influenza virus PA protein, which harbors endonuclease activity and is essential for influenza virus replication. Influenza virus replication takes place inside the cell within the nucleus. Thus, compounds designed to inhibit PA endonuclease activity need to cross both the cellular and the nuclear membrane, a property which strongly depends on designed-in physico-chemical properties of the compounds.

Furthermore, also without wishing to be bound by theory, it is assumed that the compounds of the present invention are capable of inhibiting binding of host mRNA cap structures to the cap-binding domain (CBD), particularly of the influenza virus. More specifically it is assumed that they directly interfere with the CBD of the influenza PB2 protein. However, delivery of a compound into a cell may represent a problem depending on, e.g., the solubility of the compound or its capabilities to cross the cell membrane.

The present invention shows that the claimed compounds have in vitro endonuclease inhibitory activity as well as in vitro polymerase inhibitory activity.

A possible measure of the in vitro endonuclease inhibitory activity of the compounds having the formula (V) is the FRET (fluorescence-resonance energy transfer)-based endonuclease activity assay disclosed herein. Preferably, the compounds exhibit a % reduction of at least about 50% at 25 µM in the FRET assay. In this context, the % reduction is the % reduction of the initial reaction velocity (v0) measured as fluorescence increase of a dual-labelled RNA substrate cleaved by the influenza virus endonuclease subunit (PA-Nter) upon compound treatment compared to untreated samples. Preferably, the compounds exhibit an $IC_{50}$ of less than about 50 µM, more preferably less than about 20 µM, in this assay. The half maximal inhibitory concentration ($IC_{50}$) is a measure of the effectiveness of a compound in inhibiting biological or biochemical function and was calculated from the initial reaction velocities (v0) in a given concentration series ranging from maximum 100 µM to at least 2 nM.

The compounds having the general formula (V) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza that has been caused by influenza virus infection and conditions associated with this viral infection such as viral pneumonia or secondary bacterial pneumonia and medicaments to treat symptoms such as chills, fever, sore throat, muscle pains, severe headache, coughing, weakness and fatigue. Furthermore, the compounds having the general formula (V) can be used in combination with anti-inflammatories.

The following combinations of medicaments are envisaged as being particularly suitable:

(i) The combination of endonuclease and cap-binding inhibitors (particularly targeting influenza). The endonuclease inhibitors are not particularly limited and can be any endonuclease inhibitor, particularly any viral endonuclease inhibitor. Preferred endonuclease inhibitors are those as defined in the US applications US 2013/0102600, US 2013/0317022, US 2013/0317021, and US 2014/0038990. The complete disclosure of these applications is incorporated herein by reference. In particular, all descriptions with respect to the general formula of the compounds according to these US applications, the preferred embodiments of the various substituents as well as the medical utility and advantages of the compounds are incorporated herein by reference.

Further preferred endonuclease inhibitors are the compounds having the general formula (II) as defined U.S. Ser. No. 61/750,023 (filed on Jan. 8, 2013) and the compounds having the general formula (V) as defined in U.S. Ser. No. 61/750,032 (filed on Jan. 8, 2013), the complete disclosure of which is incorporated by reference. In particular, all descriptions with respect to the general formula of these compounds, the preferred embodiments of the various substituents as well as the medical utility and advantages of the compounds are incorporated herein by reference. These compounds can be optionally in the form of a pharmaceutically acceptable salt, solvate, polymorph, codrug, cocrystal, prodrug, tautomer, racemate, enantiomer, or diastereomer or mixture thereof.

The cap-binding inhibitors are not particularly limited either and can be any cap-binding inhibitor, particularly any viral cap-binding inhibitor. Preferred cap-binding inhibitors are those having the general formula (II) as defined in US application 2013/0102601 and/or the compounds disclosed in WO2011/000566, the complete disclosure of which is incorporated by reference. In particular, all descriptions with respect to the general formula of the compounds according to US 2013-0102601 or WO2011/000566, the preferred embodiments of the various substituents as well as the medical utility and advantages of the compounds are incorporated herein by reference.

Widespread resistance to both classes of licensed influenza antivirals (M2 ion channel inhibitors (adamantanes) and neuraminidase inhibitors (e.g. oseltamivir)) occurs in both pandemic and seasonal emerging influenza strains, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to adamantanes (rimantadine and amantadine), and for oseltamivir, the most widely prescribed neuraminidase inhibitor (NAI), the WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no oseltamivir-susceptibility. Considering the fact that now most national governments have been stockpiling NAIs as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and were found to act highly synergistically. However, it is known that for both types of antivirals resistant viruses emerge rather rapidly and this issue is not tackled by combining these established antiviral drugs.

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. These two targets are located within distinct subunits of the polymerase complex and thus represent unique drug targets. Due to the fact that both functions are required for the so-called "cap-snatching" mechanism which is essential for viral transcription, concurrent inhibition of both functions is expected to act highly synergistically. This highly efficient drug combination would result in lower substance concentrations and hence improved dose-response-relationships and better side effect profiles.

Both active sites are highly conserved among all influenza A strains (e.g., avian and human) and even influenza B viruses, and hence this high degree of sequence conservation underpins the perception that these targets are not likely to trigger rapid resistant virus generation. Additionally, close interaction with host proteins render these viral proteins less prone to mutations. Thus, endonuclease and cap-binding inhibitors individually and in combination are ideal drug candidates to combat both seasonal and pandemic influenza, irrespectively of the virus strain.

The combination of an endonuclease inhibitor and a cap-binding inhibitor or a dual specific polymerase inhibitor targeting both the endonuclease active site and the cap-binding domain would be effective against virus strains resistant against adamantanes and neuraminidase inhibitors and moreover combine the advantage of low susceptibility to resistance generation with activity against a broad range of virus strains.

(ii) The combination of inhibitors of different antiviral targets (particularly targeting influenza virus) focusing on the combination with (preferably influenza virus) polymerase inhibitors as dual or multiple combination therapy. Influenza virus polymerase inhibitors are novel drugs targeting the transcription and replication activity of the polymerase. Selective inhibitors against the viral polymerase severely attenuate virus infection by stopping the viral reproductive cycle. The combination of a polymerase inhibitor specifically addressing a viral intracellular target with an inhibitor of a different antiviral target is expected to act highly synergistically. This is based on the fact that these different types of antiviral drugs exhibit completely different mechanisms of action requiring different pharmacokinetics properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the first group of polymerase inhibitors (e.g., cap-binding and endonuclease inhibitors) is combined with at least one compound selected from the second group of polymerase inhibitors.

The first group of polymerase inhibitors which can be used in this type of combination therapy includes, but is not limited to, the compounds having the formula (V).

The second group of polymerase inhibitors which can be used in this type of combination therapy includes, but is not limited to, the compounds having the general formula (I) as defined in the US application US 2013/0102600, the compounds having the general formula (II) as defined in US application US 2013/0102601, the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

(iii) The combination of polymerase inhibitors with neuraminidase inhibitors

Influenza virus polymerase inhibitors are novel drugs targeting the transcription and replication activity of the polymerase. The combination of a polymerase inhibitor specifically addressing a viral intracellular target with an inhibitor of a different extracellular antiviral target, especially the (e.g., viral) neuraminidase is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one neuraminidase inhibitor.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination of polymerase inhibitors with M2 channel inhibitors

Influenza virus polymerase inhibitors are novel drugs targeting the transcription and replication activity of the polymerase. The combination of a polymerase inhibitor specifically addressing a viral intracellular target with an inhibitor of a different extracellular and cytoplasmic antiviral target, especially the viral M2 ion channel, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically, at least one compound selected from the above mentioned first group of polymerase inhibitors is combined with at least one M2 channel inhibitor.

The M2 channel inhibitor (particularly influenza M2 channel inhibitor) is not specifically limited. Examples include amantadine and rimantadine.

(v) The combination of polymerase inhibitors with alpha glucosidase inhibitors

Influenza virus polymerase inhibitors are novel drugs targeting the transcription and replication activity of the polymerase. The combination of a polymerase inhibitor specifically addressing a viral intracellular target, with an inhibitor of a different host-cell target, especially alpha glucosidase, is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of cellular targets interacting with viral replication with polymerase inhibitors.

Typically, at least one compound selected from the above-mentioned first group of polymerase inhibitors is combined with at least one alpha glucosidase inhibitor.

The alpha glucosidase inhibitor is not specifically limited. Examples include the compounds described in Chang et al., Antiviral Research 2011, 89, 26-34.

(vi) The combination of polymerase inhibitors with ligands of other influenza targets Influenza virus polymerase inhibitors are novel drugs targeting the transcription and replication activity of the polymerase. The combination of a polymerase inhibitor specifically addressing a viral intracellular target with an inhibitor of different extracellular, cytoplasmic or nucleic antiviral targets is expected to act highly synergistically. This is based on the fact that these different types of antiviral drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Typically at least one compound selected from the above mentioned first group of polymerase inhibitors is combined with at least one ligand of another influenza target.

The ligand of another influenza target is not specifically limited. Examples include compounds acting on the sialidase fusion protein (e.g., Fludase (DAS181), siRNAs and phosphorothioate oligonucleotides), signal transduction inhibitors (e.g., ErbB tyrosine kinase, Abl kinase family, MAP kinases, PKCa-mediated activation of ERK signalling) as well as interferon (inducers).

(vii) The combination of (preferably influenza) polymerase inhibitors with a compound used as an adjuvant to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists)). Influenza virus polymerase inhibitors are novel drugs targeting the transcription and replication activity of the polymerase. The combination of a polymerase inhibitor specifically addressing a viral intracellular target with a compound used as an adjuvance to minimize the symptoms of the disease address the causative and symptomatic pathological consequences of viral infection. This combination is expected to act synergistically because these different types of drugs exhibit completely different mechanisms of action requiring different pharmacokinetic properties which act advantageously and synergistically on the antiviral efficacy of the combination.

This highly efficient drug combination would result in lower substance concentrations and hence improved dose-response-relationships and better side effect profiles. Moreover, advantages described above for polymerase inhibitors would prevail for combinations of inhibitors of different antiviral targets with polymerase inhibitors.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention as indicated by the appended claims in any way.

EXAMPLES

FRET Endonuclease Activity Assay

The influenza A virus (IAV) PA-Nter fragment (amino acids 1-209) harboring the influenza endonuclease activity was generated and purified as described in Dias et al., Nature 2009; April 16; 458(7240), 914-918. The protein was dissolved in buffer containing 20 mM Tris pH 8.0, 100 mM NaCl and 10 mM β-mercaptoethanol and aliquots were stored at −20° C.

A 20 bases dual-labelled RNA oligo with 5'-FAM fluorophore and 3'-BHQ1 quencher was used as a substrate to be cleaved by the endonuclease activity of the PA-Nter. Cleavage of the RNA substrate frees the fluorophore from the quencher resulting in an increase of the fluorescent signal.

All assay components were diluted in assay buffer containing 20 mM Tris-HCl pH 8.0, 100 mM NaCl, 1 mM $MnCl_2$, 10 mM $MgCl_2$ and 10 mM β-mercaptoethanol. The final concentration of PA-Nter was 0.5 μM and 1.6 μM RNA substrate. The test compounds were dissolved in DMSO and generally tested at two concentrations or a concentration series resulting in a final plate well DMSO concentration of 0.5%. In those cases where the compounds were not soluble at that concentration, they were tested at the highest soluble concentration.

5 μl of each compound dilution was provided in the wells of white 384-well microtiter plates (PerkinElmer) in eight replicates. After addition of PA-Nter dilution, the plates were sealed and incubated for 30 min at room temperature prior to the addition of 1.6 μM RNA substrate diluted in assay buffer. Subsequently, the increasing fluorescence signal of cleaved RNA was measured in a microplate reader (Synergy HT, Biotek) at 485 nm excitation and 535 nm emission wavelength. The kinetic read interval was 35 sec at a sensitivity of 35. Fluorescence signal data over a period of 20 min were used to calculate the initial velocity (v0) of substrate cleavage. Final readout was the % reduction of v0 of compound-treated samples compared to untreated. The half maximal inhibitory concentration ($IC_{50}$) is a measure of the effectiveness of a compound in inhibiting biological or biochemical function and was calculated from the initial reaction velocities (v0) in a given concentration series ranging from maximum 100 μM to at least 2 nM.

Cytopathic Effect (CPE) Assay

The influenza A virus (IAV) was obtained from American Tissue Culture Collection (A/Aichi/2/68 (H3N2); VR-547). Virus stocks were prepared by propagation of virus on Mardin-Darby canine kidney (MDCK; ATCC CCL-34) cells and infectious titres of virus stocks were determined by the 50% tissue culture infective dose ($TCID_{50}$) analysis as described in Reed, L. J., and H. Muench. 1938, Am. J. Hyg. 27:493-497.

MDCK cells were seeded in 96-well plates at $2\times10^4$ cells/well using DMEM/Ham's F-12 (1:1) medium containing 10% foetal bovine serum (FBS), 2 mM L-glutamine and 1% antibiotics (all from PAA). Until infection the cells were incubated for 5 hrs at 37° C., 5.0% $CO_2$ to form a ~80% confluent monolayer on the bottom of the well. Each test compound was dissolved in DMSO and generally tested at 25 μM and 250 μM. In those cases where the compounds were not soluble at that concentration they were tested at the highest soluble concentration. The compounds were diluted in infection medium (DMEM/Ham's F-12 (1:1) containing 5 μg/ml trypsin, and 1% antibiotics) for a final plate well DMSO concentration of 1%. The virus stock was diluted in infection medium (DMEM/Ham's F-12 (1:1) containing 5 μg/ml Trypsin, 1% DMSO, and 1% antibiotics) to a theoretical multiplicity of infection (MOI) of 0.05.

After removal of the culture medium and one washing step with PBS, virus and compound were added together to the cells. In the wells used for cytotoxicity determination (i.e. in the absence of viral infection), no virus suspension was added. Instead, infection medium was added. Each treatment was conducted in two replicates. After incubation at 37° C., 5% $CO_2$ for 48 hrs, each well was observed microscopically for apparent cytotoxicity, precipitate formation, or other notable abnormalities. Then, cell viability was determined using CellTiter-Glo luminescent cell viability assay (Promega). The supernatant was removed carefully and 65 μl of the reconstituted reagent were added to each well and incubated with gentle shaking for 15 min at room temperature. Then, 60 μl of the solution was transferred to an opaque plate and luminescence (RLU) was measured using Synergy HT plate reader (Biotek).

Relative cell viability values of uninfected-treated versus uninfected-untreated cells were used to evaluate cytotoxicity of the compounds. Substances with a relative viability below 80% at the tested concentration were regarded as cytotoxic and retested at lower concentrations.

Reduction in the virus-mediated cytopathic effect (CPE) upon treatment with the compounds was calculated as follows: The response (RLU) of infected-untreated samples was subtracted from the response (RLU) of the infected-treated samples and then normalized to the viability of the corresponding uninfected sample resulting in % CPE reduction. The half maximal inhibitory concentration ($IC_{50}$) is a measure of the effectiveness of a compound in inhibiting biological or biochemical function and was calculated from the RLU response in a given concentration series ranging from maximum 100 μM to at least 100 nM.

Biacore Assay

The PB2 cap binding domain (CBD) of an avian H5N1 influenza virus was immobilized on the surface of a CM7 sensor chip (GE Healthcare) by amine coupling according to the manufacturer's protocol. The protein was diluted in a 10 mM phosphate buffer pH 6.5. As running buffer for immobilization a HBS-EP buffer (10 mM HEPES, 150 mM NaCl, 3 mM EDTA, 0.005% Surfactant p20) was used. Using a protein concentration of 30 μg/ml and a contact time of 12 min an immobilization level of approximately 8000 RU (relative response units) was achieved.

For compound screening a running buffer containing 10 mM TRIS, 3 mM EDTA, 150 mM NaCl, 0.005% Surfactant p20 (GE Healthcare/Biacore), 1 mM DTT, 0.5% DMSO was used. 2 mM DMSO stock solutions of each compound were diluted in 1.005× sample buffer without DMSO (1.005× TRIS/EDTA/NaCl/p20/DTT; diluted from a 10× stock) to a final compound concentration of 10 μM and 0.5% DMSO. m7GTP (Sigma Aldrich) and SAV-7160 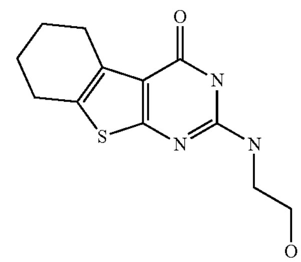 [SMILES: O=c1[nH]c(NCCO)nc2sc3c(c12)CCCC3] were used as references and chip stability controls at a concentration of 4 mM and 10 μM, respectively. Stock solutions of each reference compound were made and aliquots were stored at −20° C.

For buffer bulk effects (matrix) was accounted by reducing the response obtained for the reference flow cell Fc1 from the active flow cell Fc2 resulting in relative response units (RU) reflecting binding of the compounds to the ligand. Organic solvents such as DMSO in the buffer cause high bulk effects which differ in the reference flow cell and the active flow cell due to ligand immobilization. To account for these differences, a calibration curve was established. Eight DMSO concentrations ranging from 0.1% to 1.5% in buffer were measured and a linear calibration curve was calculated by plotting Fc2-Fc1 vs. Fc1. The relative response of each sample was then corrected by the solvent factor given by the respective Fc1 signal on the calibration curve and the corresponding Fc2-Fc1 difference. To account for the different size of the compounds, the buffer and solvent corrected response units were normalized to the molecular weight.

Affinity constants (KD values) were determined by measuring the binding affinity of the analyte to the ligand over a concentration range ranging from 200 μM to 1 nM. The KD value is that concentration at which 50% of the binding sites are saturated and was calculated using a linear curve fit model.

Determination of $IC_{50}$ Values—Transcription Assay (TA Assay)

TA Assay Principle

To analyze the activity of the inhibitors, a transcription assay (TA) was employed using the whole RNP complex in a cell-free environment without the use of radioactively labeled nucleotides.

An in vitro synthesized capped mRNA oligo serves as primer for viral mRNA synthesis as cap-snatching substrate for the viral RNPs and newly synthesized viral mRNA is detected using Quantigene® 2.0 technology. The Quantigene® (QG) technology is based on RNA hybridization bound to coated 96-well plates followed by branched DNA (bDNA) signal amplification. Three different types of probes are responsible for specific hybridization to the gene of interest. The Capture Extenders (CE) hybridize to specific gene regions and concurrently immobilize the RNA to the QG Capture Plate. The Label Extenders (LE) also specifically hybridize to the gene of interest and provide a sequence for the signal amplification tree to be built up via sequential hybridization of preAmplifier (PreAmp), Amplifier (Amp) and alkaline phosphatase Label Probe. The signal is then detected by adding chemiluminescent substrate and using a microplate luminometer for the read out. The third probe blocks nonspecific interactions (Blocking Probe; BP). Generally, probe sets for IAV detection are designed to detect either the negative sense genomic vRNA or synthesized positive sense RNA (+RNA), without differentiating between cRNA or mRNA for translation. For the TA assay, the probe sets and the QG 2.0 protocol were adapted and modified to fit the purpose of a biochemical assay suitable for testing of antiviral compounds in a cell-free environment.

Materials and Methods

Compounds

All compounds were dissolved in DMSO and stored at 4° C. All other reagents were obtained from Sigma-Aldrich if not stated otherwise.

Preparation of RNA Substrate

The substrate RNA used was derived from in vitro transcribed RNA synthesized by T7 High Yield RNA Synthesis Kit (New England BioLabs Inc.) generated according to the manufacturer's protocol but with extended incubation time of 16 hr. The RNA product was gel-purified using miRNeasy Mini Kit (Qiagen). The RNA was enzymatically capped using ScriptCap m7G Capping System (CellScript, Madison Wis.). The resulting capped RNA oligonucleotide (5'-m7GpppG-GGG AAU ACU CAA GCU AUG CAU CGC AUU AGG CAC GUC GAA GUA-3'; SEQ ID NO:1) served as primer for the influenza virus polymerase.

Preparation of RNPs

All experiments were done on IAV strain A/PR/8/34, amplified either in embryonated chicken eggs or obtained purified and concentrated from Charles River Laboratories. Egg-amplified virus was PEG-precipitated using 4% w/v PEG8000 in 2 mM Tris-HCl (pH 8.0) buffer containing 100 mM NaCl (4° C., 45 min) and centrifuged at 3600 g at 4° C. for 45 min. The pellet was suspended in a 10 mM Tris-HCl (pH 8.0) buffer containing 100 mM NaCl and 6% w/v sucrose and was then purified through a 30% w/v sucrose cushion (109,000 g, 120 min, 4° C.).

The RNP purification was performed as previously published with some modifications (Klumpp et al. 2001. Influenza virus endoribonuclease, p. 451-466, 342 ed.). The virus lyophilisate was solved in 1× lysis buffer (1% w/v Triton X-100, 1 mg/mL lysolecithin, 2.5 mM $MgCl_2$, 100 mM KCl, 5 mM DTT, 2.5% v/v glycerol, 20 mM Tris-HCl (pH8.0), 20 U/mL RNase inhibitor) at a final virus protein concentration of 2 mg/mL and was then incubated for 60 minutes at 30° C. 3.3 mL of the resulting lysate was loaded onto a glycerol gradient (2 mL 70% v/v, 1.5 mL 50% v/v, 0.75 mL 40% v/v and 3.6 mL 33% v/v—buffered in 20 mM Tris-HCl, 50 mM NaCl, 5 mM DTT, 5 mM 2-mercaptoehtanol). The gradients were spun in a Sorvall Ultra centrifuge, AH641 rotor, for 6 hours at 4° C. and 240,000 g. Fractions (0.5 mL) were collected from the top of the gradient. The fractions containing the RNP particles were pooled, further concentrated with 10 kD VivaSpin2 columns and stored at −20° C. The RNP concentration was determined by UV spectroscopy, using OD260 nm of 1.0=60 mg/mL RNP as conversion factor (Klumpp et al. 2001. Influenza virus endoribonuclease, p. 451-466, 342 ed.).

RNA Analysis and Transcription Assay (TA Assay)

All types of viral RNA were analysed by Quantigene® using specific probe sets designed to detect either the negative sense genomic vRNA (−RNA; Cat. No. SF-10318), newly synthesized positive sense RNA (+RNA; Cat. No. SF-10049), or newly synthesized viral mRNA (TA assay; SF-10542) according to the manufacturer's instructions with the exception that all incubation steps during the Quantigene® procedure were done at 49° C.

For the standard reaction, 80 μM RNPs were incubated for 2 hrs at 30° C. with a dilution series of the inhibitors at 1% v/v final DMSO concentration in reaction buffer (55 mM Tris-HCl, 20 mM KCl, 1 mM $MgCl_2$, 0.2% v/v Triton X-100, 0.25 U/μL RNaseOut, 12.5 mM NaCl, 1.25 mM DTT, 1.25 mM 2-mercaptoethanol, 12.5% v/v glycerol). Then 2 nM capped RNA substrate was added, followed by incubation for 2 hrs at 30° C. The reaction was terminated by incubation at 95° C. for 5 min.

For the detection of the synthesized mRNA the Quantigene® 2.0 (Panomics. 2007. QuantiGene 2.0 Reagent System. User Manual) was used with the probe sets specified. The probe sets consists of Capture Extenders (CE), Label Extenders (LE) and Blocking Probes (BP) and were generated by and supplied as a mix of all three by by Affymetrix/ Panomics. The probe sequences are represented in SEQ ID NOs: 5 to 20 and are also given in FIG. 1.

The response values (relative luminescence units) were analyzed using GraphPad Prism to determine $IC_{50}$ values and 95% confidence intervals using a 4-parameter logistic equation. Positive and negative controls were included to define top and bottom for fitting the curve.

De novo synthesized viral mRNA was generated by incubating purified RNPs with a capped RNA substrate of known sequence.

The Quantigene® probe set "TA assay" detects newly synthesized viral mRNA coding for nucleoprotein (NP), the Label Extenders (LE1 and LE2) specifically hybridize to the snatched cap sequence 5'-cap-GGGGGAAUACUCAAG-3' (SEQ ID NO: 2) cleaved off from the 44-mer RNA substrate and to the polyA sequence, respectively. The Capture Extenders (CE1-9) specifically hybridize to regions within the coding region of the IAV NP gene. Probe set "+RNA" detects positive sense viral RNA coding for NP by specifically binding to more than 10 different regions within the gene. LE and CE of this probe set hybridize to regions between nucleotides 1 and 1540 (GenBank CY147505) and does not distinguish between viral mRNA and viral cRNA. The third probe set "−RNA" specifically hybridized to negative sense RNA (nsRNA), coding for the nonstructural protein (NS).

TA Assay Results for the Compounds of the Invention

Employing the above described TA assay, $IC_{50}$ values were determined for the compounds of the present invention.

| Formula, no. | Biacore | FRET | CPE |
|---|---|---|---|
| [structure] | $K_D > 100$ μM | $IC_{50} = 0.40$ μM | $IC_{50} > 50$ μM |

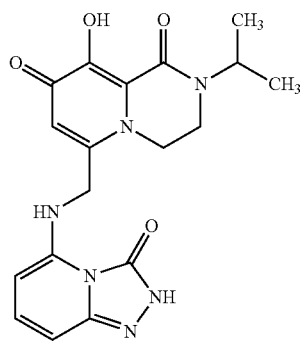 [SMILES: CC(C)N1CCn2c(CNc3cccc4n[nH]c(=O)n34)cc(=O)c(O)c2C1=O]
$K_D = 99.3\ \mu M$  $IC_{50} = 0.936\ \mu M$  $IC_{50} > 50\ \mu M$
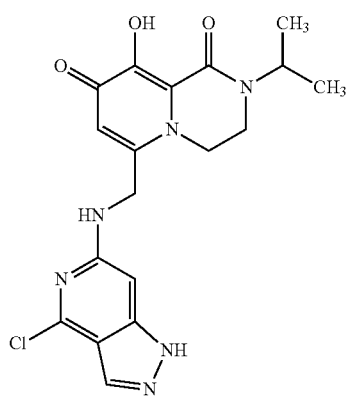 [SMILES: CC(C)N1CCn2c(CNc3cc4[nH]ncc4c(Cl)n3)cc(=O)c(O)c2C1=O]
$K_D = 305.2\ \mu M$  $IC_{50} = 0.848\ \mu M$  $IC_{50} > 50\ \mu M$
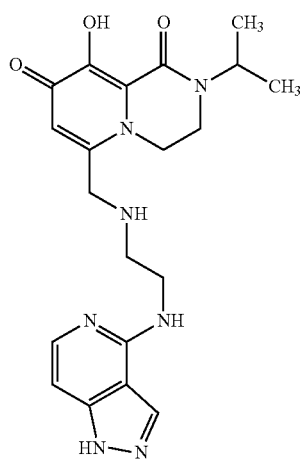 [SMILES: CC(C)N1CCn2c(CNCCNc3nccc4[nH]ncc34)cc(=O)c(O)c2C1=O]
n.d.  $IC_{50} = 1.46\ \mu M$  $IC_{50} > 50\ \mu M$ -continued
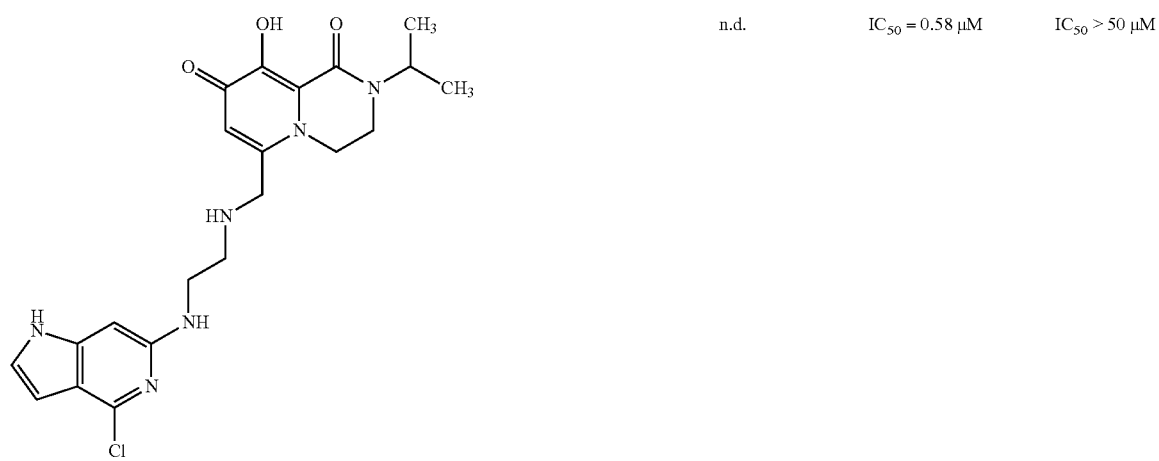
n.d.  IC$_{50}$ = 0.58 µM  IC$_{50}$ > 50 µM
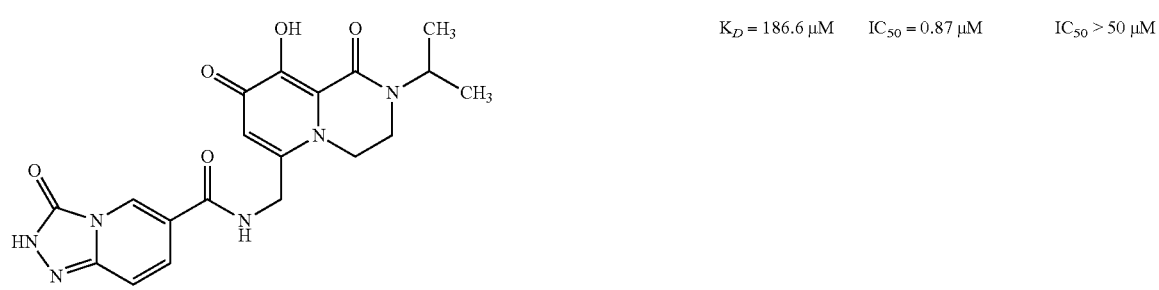
K$_D$ = 186.6 µM  IC$_{50}$ = 0.87 µM  IC$_{50}$ > 50 µM
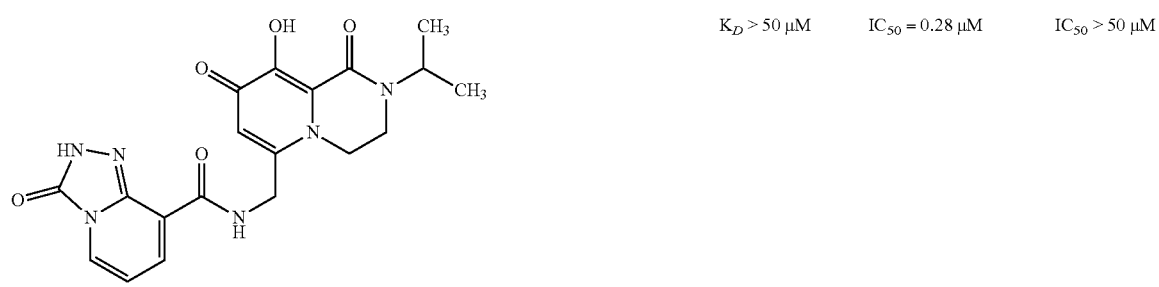
K$_D$ > 50 µM  IC$_{50}$ = 0.28 µM  IC$_{50}$ > 50 µM
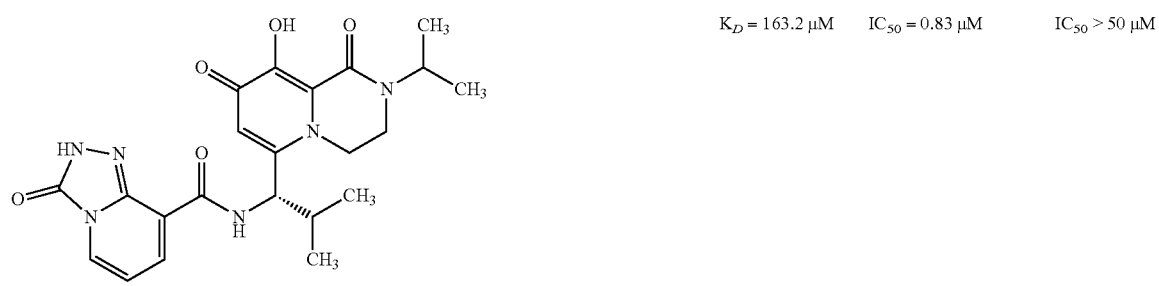
K$_D$ = 163.2 µM  IC$_{50}$ = 0.83 µM  IC$_{50}$ > 50 µM -continued
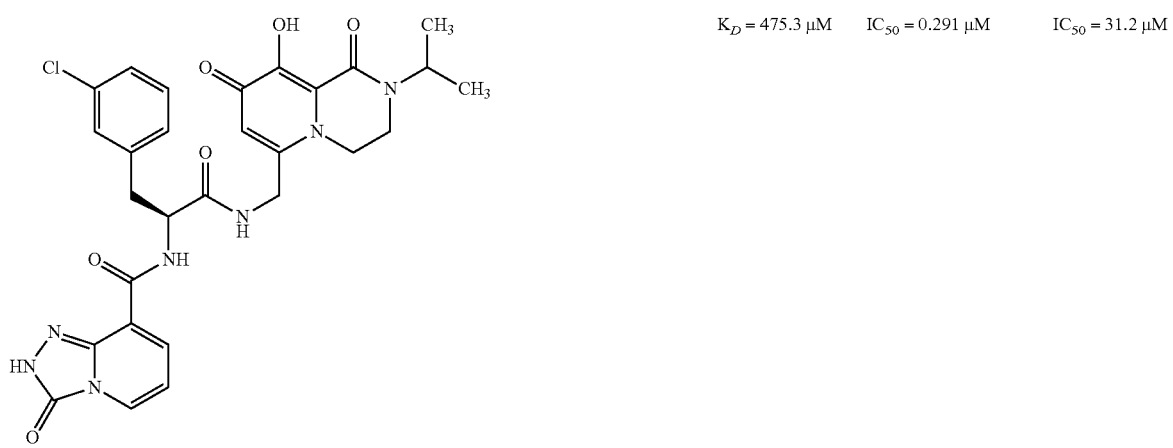
$K_D$ = 475.3 μM   $IC_{50}$ = 0.291 μM   $IC_{50}$ = 31.2 μM
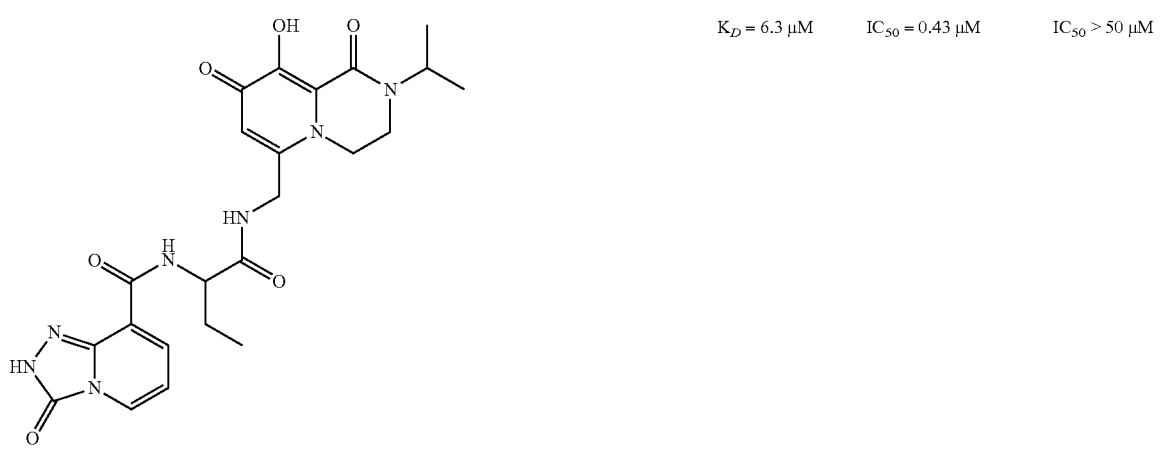
$K_D$ = 6.3 μM   $IC_{50}$ = 0.43 μM   $IC_{50}$ > 50 μM
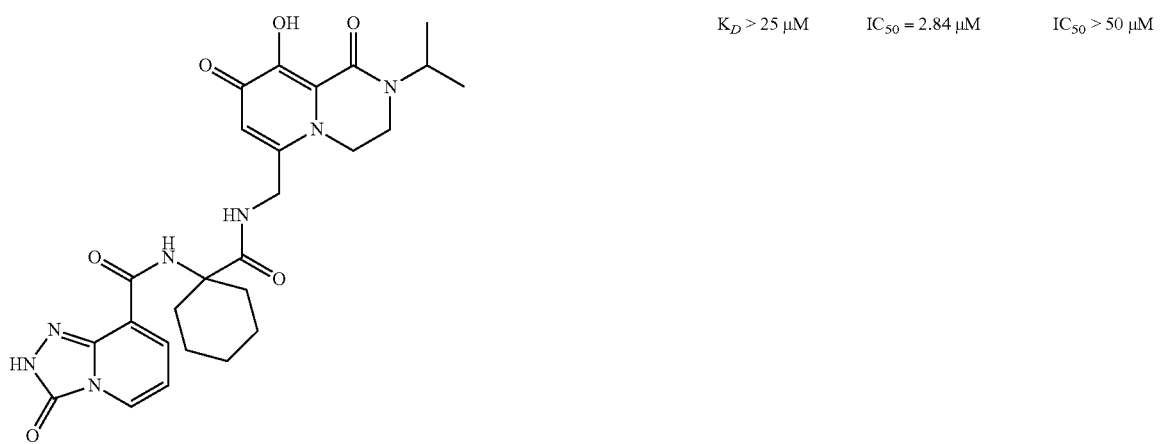
$K_D$ > 25 μM   $IC_{50}$ = 2.84 μM   $IC_{50}$ > 50 μM

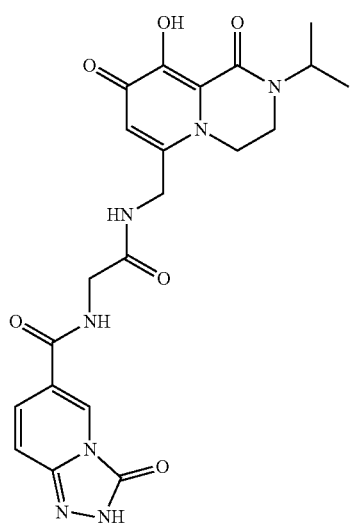 [SMILES: CC(C)N1CCn2c(CNC(=O)CNC(=O)c3ccc4n[nH]c(=O)n4c3)cc(=O)c(O)c2C1=O]
$K_D = 14.1\ \mu M$     $IC_{50} = 1.94\ \mu M$     $IC_{50} > 50\ \mu M$
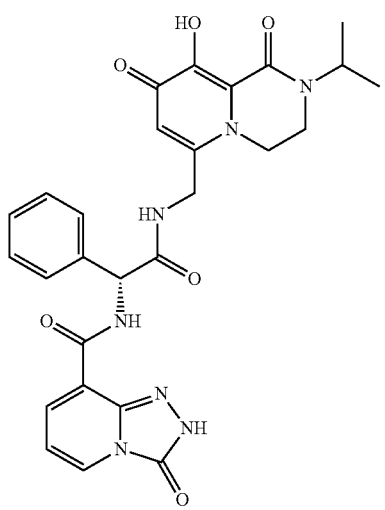 [SMILES: CC(C)N1CCn2c(CNC(=O)[C@H](NC(=O)c3cccn4c(=O)[nH]nc34)c3ccccc3)cc(=O)c(O)c2C1=O]
$K_D > 100\ \mu M$     $IC_{50} = 9.87\ \mu M$     $IC_{50} > 50\ \mu M$
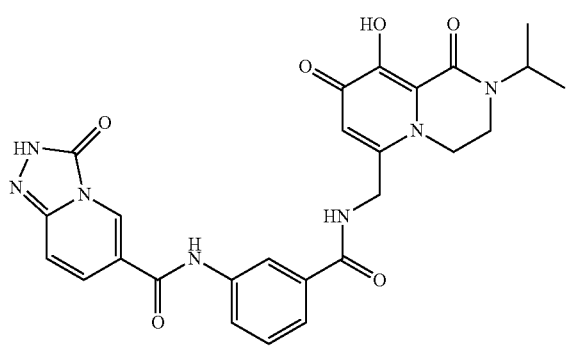 [SMILES: CC(C)N1CCn2c(CNC(=O)c3cccc(NC(=O)c4ccc5n[nH]c(=O)n5c4)c3)cc(=O)c(O)c2C1=O]
$K_D = 21.9\ \mu M$     $IC_{50} = 1.66\ \mu M$     $IC_{50} = 35.1\ \mu M$

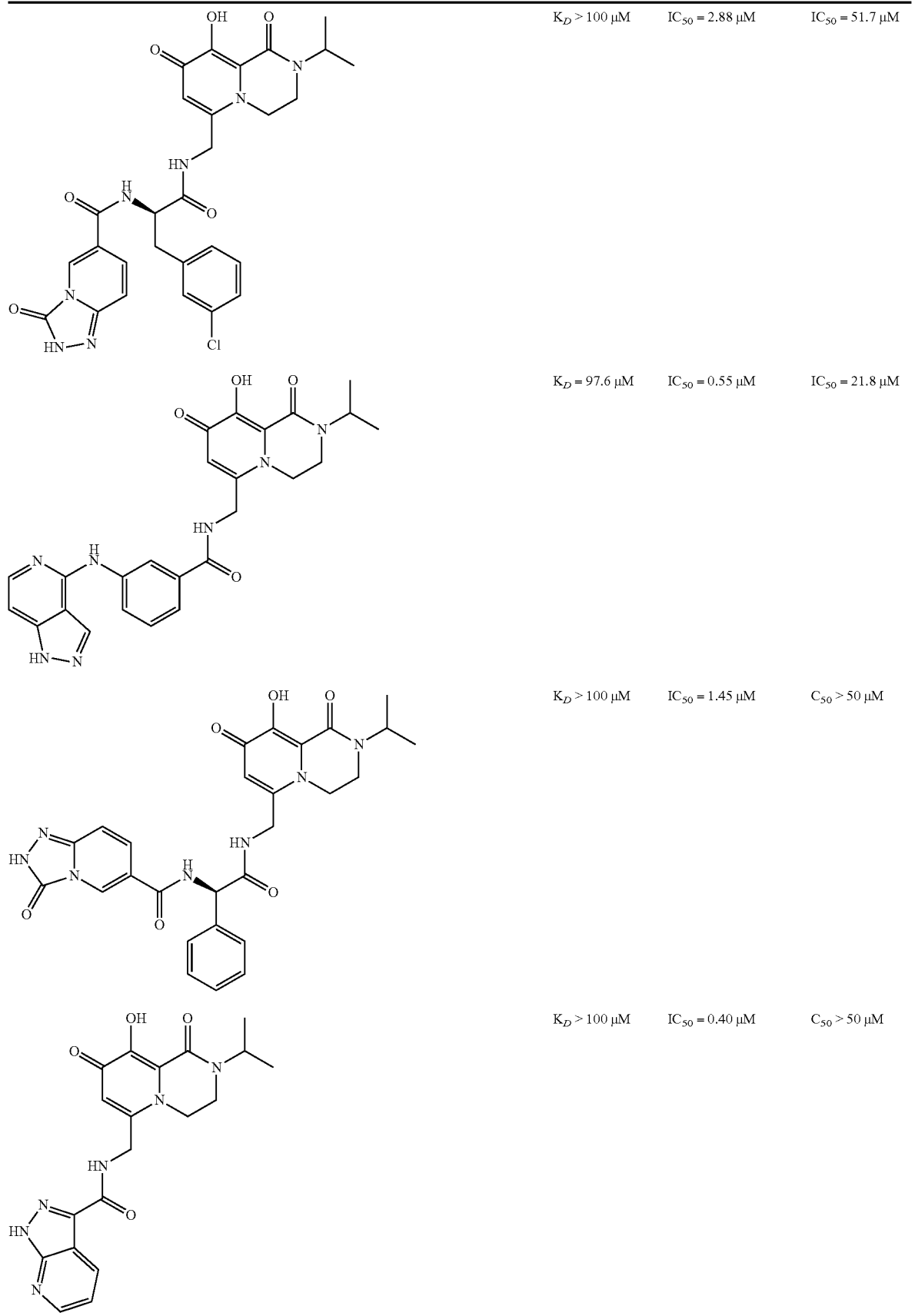
| | | |
|---|---|---|
| $K_D > 100$ μM | $IC_{50} = 2.88$ μM | $IC_{50} = 51.7$ μM |
| $K_D = 97.6$ μM | $IC_{50} = 0.55$ μM | $IC_{50} = 21.8$ μM |
| $K_D > 100$ μM | $IC_{50} = 1.45$ μM | $C_{50} > 50$ μM |
| $K_D > 100$ μM | $IC_{50} = 0.40$ μM | $C_{50} > 50$ μM |

-continued
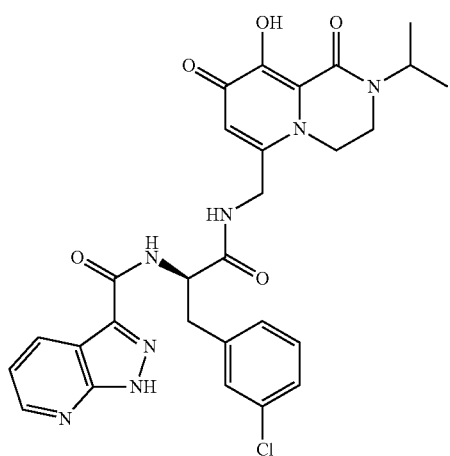 [SMILES: CC(C)N1CCn2c(CNC(=O)[C@@H](Cc3cccc(Cl)c3)NC(=O)c3n[nH]c4ncccc34)cc(=O)c(O)c2C1=O]
$K_D = 55.1\ \mu M$  $IC_{50} = 1.09\ \mu M$  $C_{50} > 50\ \mu M$
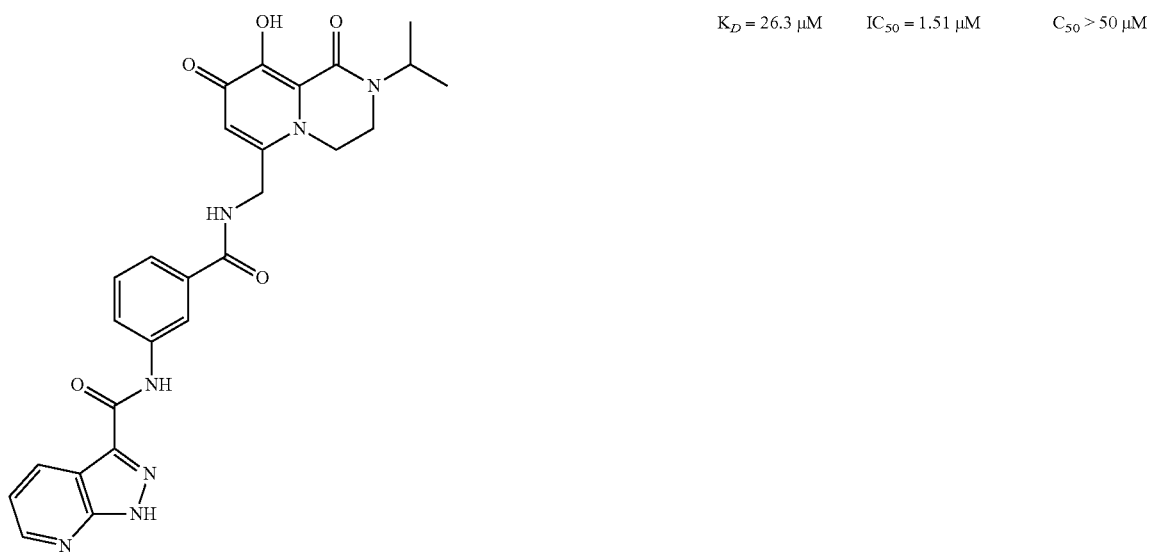
$K_D = 26.3\ \mu M$  $IC_{50} = 1.51\ \mu M$  $C_{50} > 50\ \mu M$
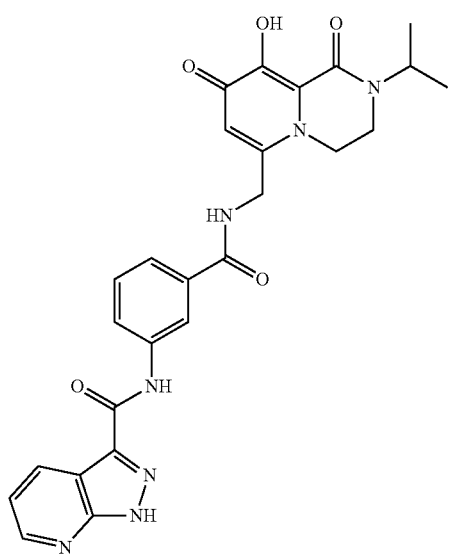 [SMILES: CC(C)N1CCn2c(CNC(=O)c3cccc(NC(=O)c4n[nH]c5ncccc45)c3)cc(=O)c(O)c2C1=O]
$K_D = 19.6\ \mu M$  $IC_{50} = 1.22\ \mu M$  $C_{50} > 50\ \mu M$ -continued
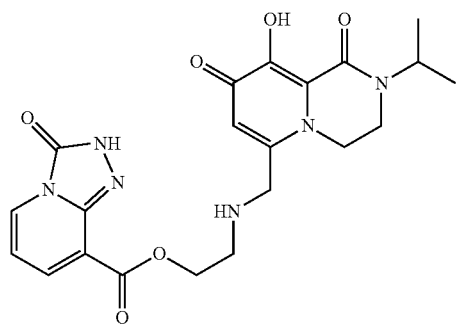 [SMILES: CC(C)N1CCn2c(CNCCOC(=O)c3cccn4c(=O)[nH]nc34)cc(=O)c(O)c2C1=O]
| $K_D > 100$ μM | $IC_{50} = 1.41$ μM | $IC_{50} > 50$ μM |
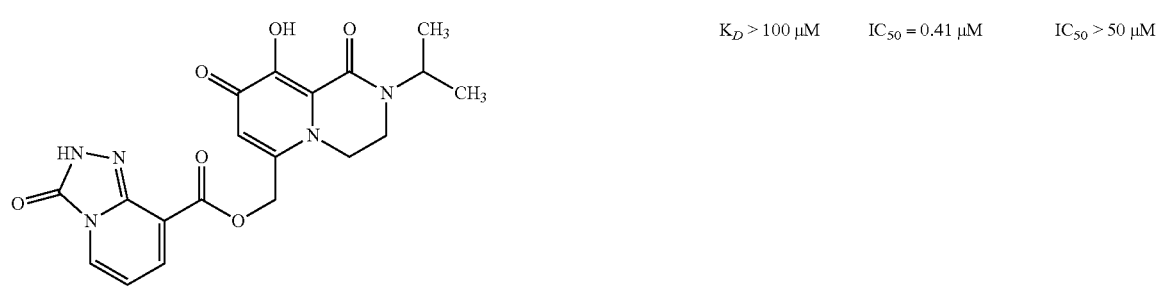
| $K_D > 100$ μM | $IC_{50} = 0.41$ μM | $IC_{50} > 50$ μM |
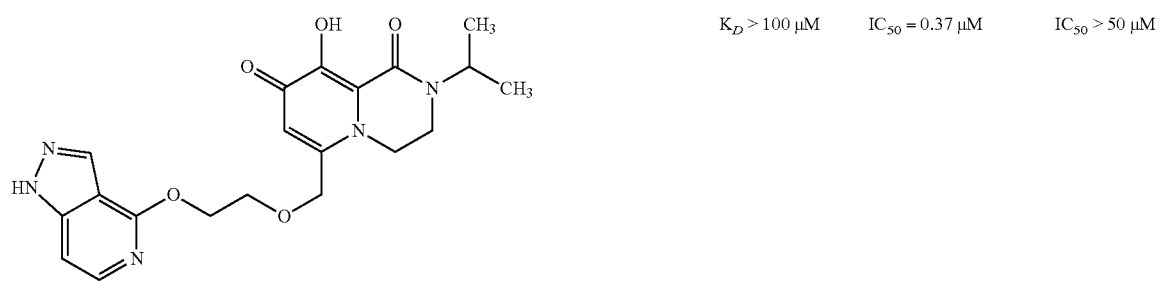
| $K_D > 100$ μM | $IC_{50} = 0.37$ μM | $IC_{50} > 50$ μM |
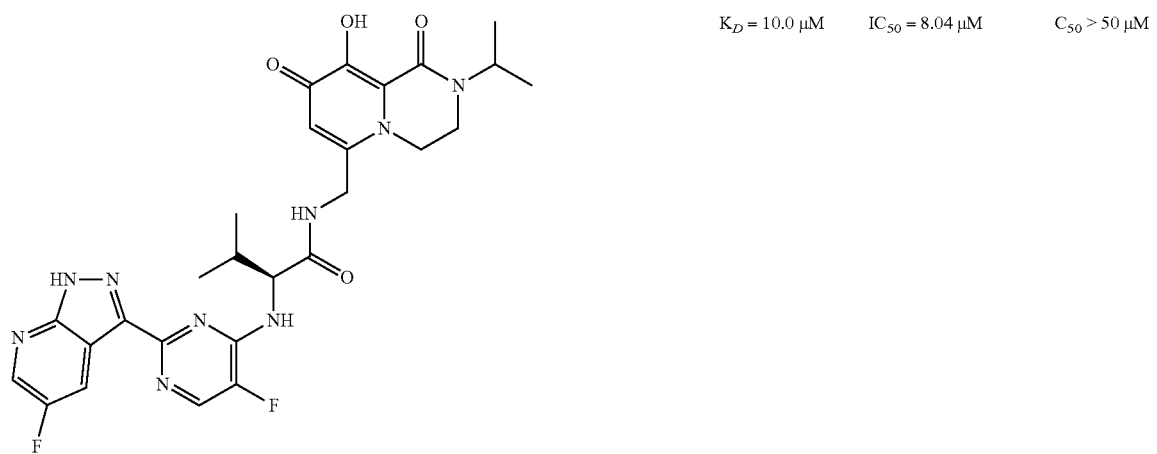
| $K_D = 10.0$ μM | $IC_{50} = 8.04$ μM | $C_{50} > 50$ μM |

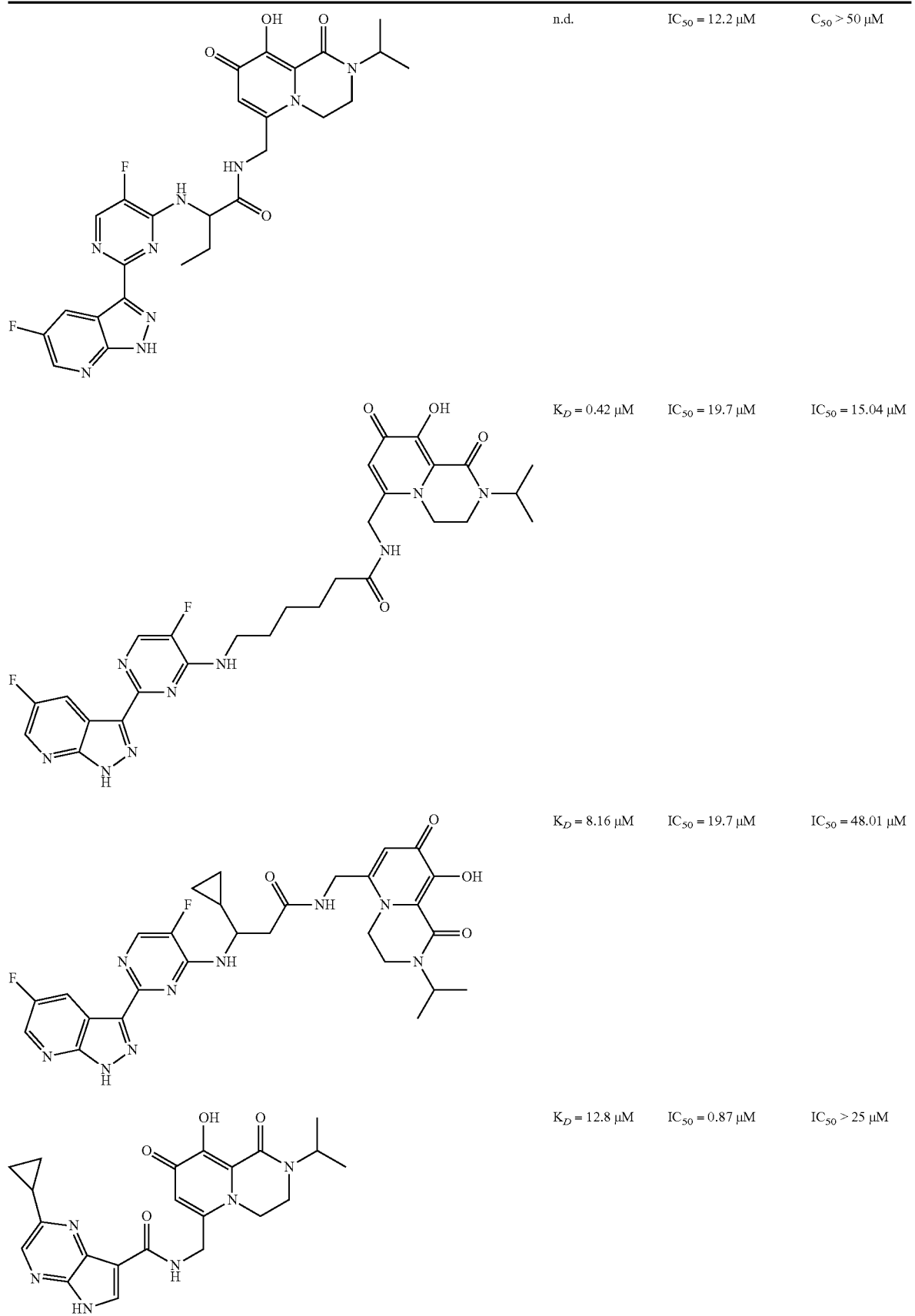

-continued
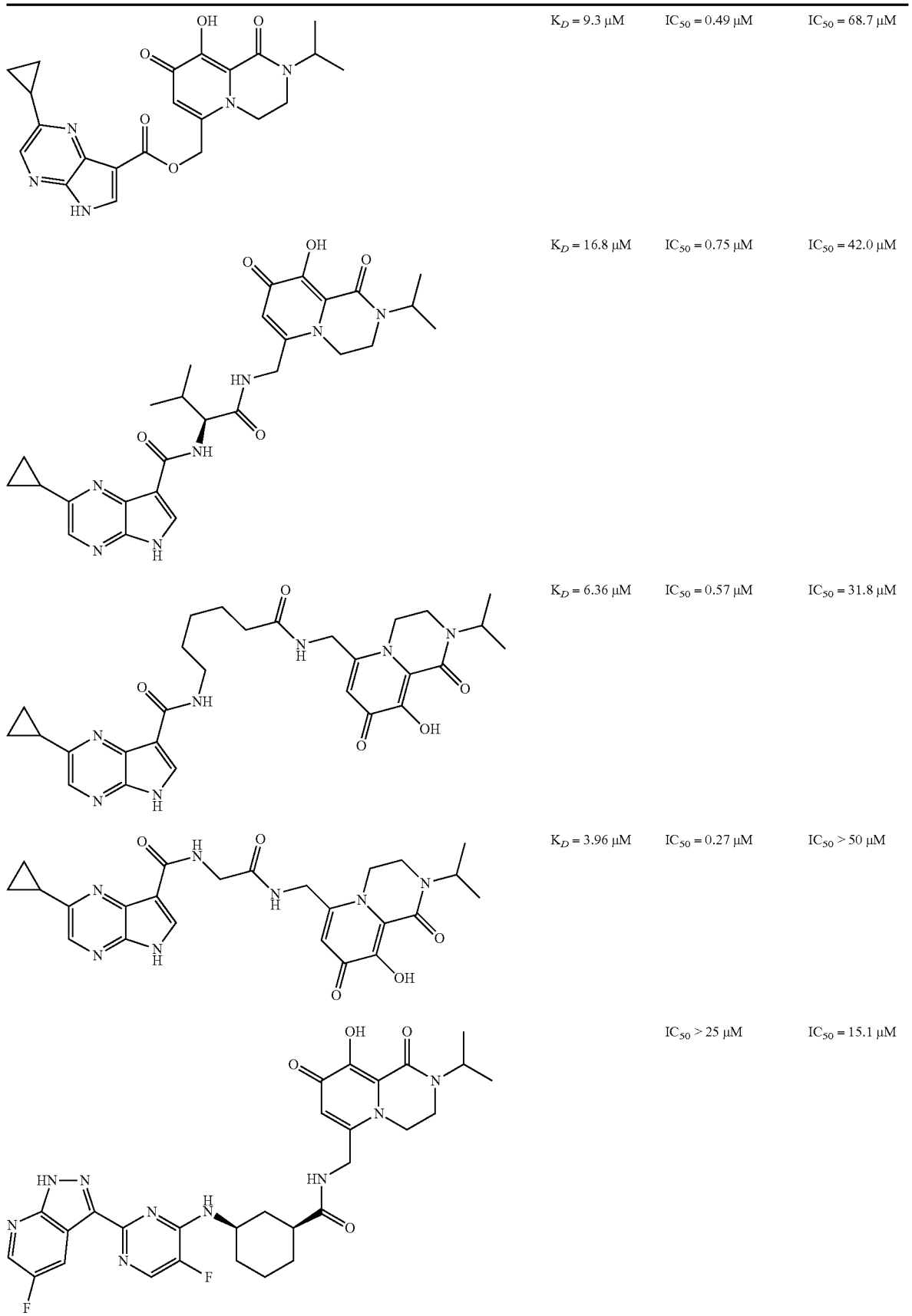
| | | |
|---|---|---|
| $K_D$ = 9.3 μM | $IC_{50}$ = 0.49 μM | $IC_{50}$ = 68.7 μM |
| $K_D$ = 16.8 μM | $IC_{50}$ = 0.75 μM | $IC_{50}$ = 42.0 μM |
| $K_D$ = 6.36 μM | $IC_{50}$ = 0.57 μM | $IC_{50}$ = 31.8 μM |
| $K_D$ = 3.96 μM | $IC_{50}$ = 0.27 μM | $IC_{50}$ > 50 μM |
| $IC_{50}$ > 25 μM | $IC_{50}$ = 15.1 μM | |

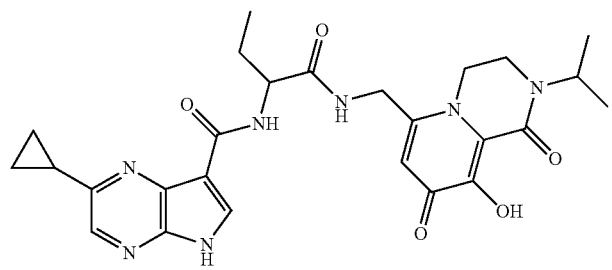 [SMILES: CCC(NC(=O)c1c[nH]c2ncc(C3CC3)nc12)C(=O)NCc1cc(=O)c(O)c2n1CCN(C(C)C)C2=O]
IC$_{50}$ = 0.46 μM    IC$_{50}$ > 50 μM
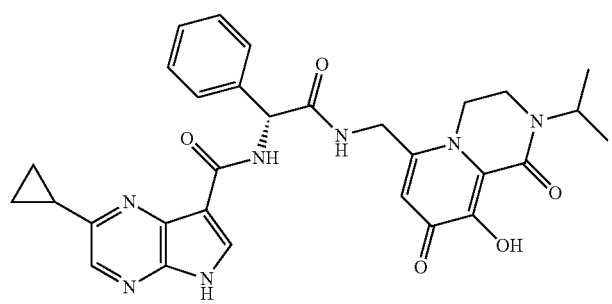 [SMILES: CC(C)N1CCn2c(CNC(=O)[C@H](NC(=O)c3c[nH]c4ncc(C5CC5)nc34)c3ccccc3)cc(=O)c(O)c2C1=O]
IC$_{50}$ = 2.34 μM    IC$_{50}$ = 8.2 μM
| Formula | TA assay | CPE |
|---|---|---|
| 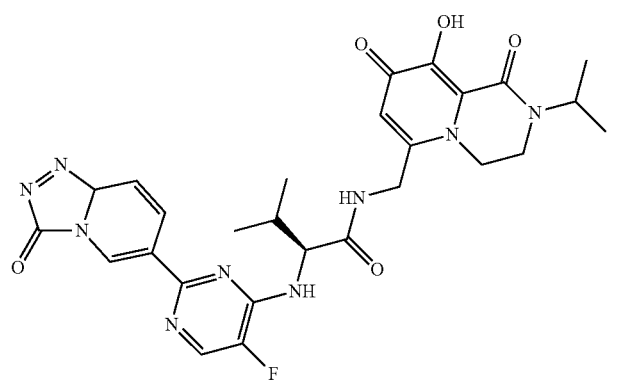 [SMILES: CC(C)[C@H](Nc1nc(C2=CN3C(=O)N=NC3C=C2)ncc1F)C(=O)NCc1cc(=O)c(O)c2n1CCN(C(C)C)C2=O] | TA<br>IC$_{50}$ = 0.38 μM | C$_{50}$ > 50 μM |
| (structure below) | TA<br>IC$_{50}$ > 50 μM | C$_{50}$ > 50 μM |

-continued
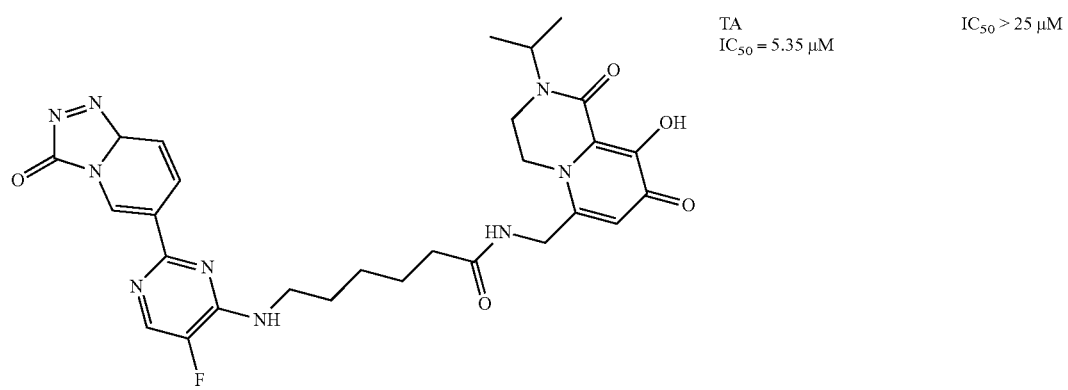
TA
IC$_{50}$ = 5.35 μM
IC$_{50}$ > 25 μM
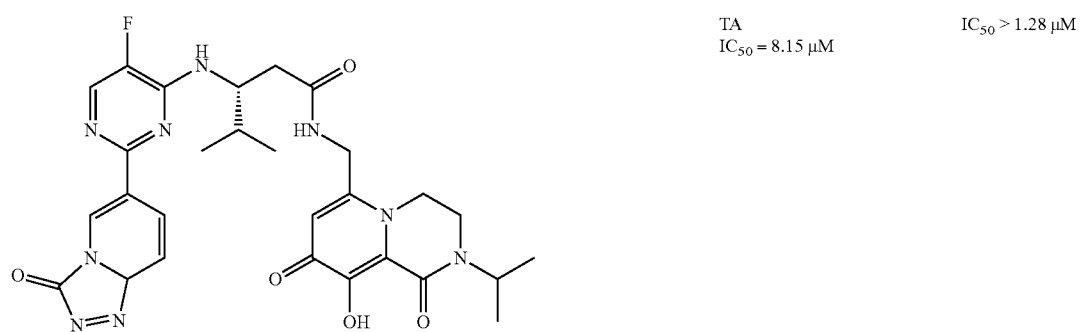
TA
IC$_{50}$ = 8.15 μM
IC$_{50}$ > 1.28 μM
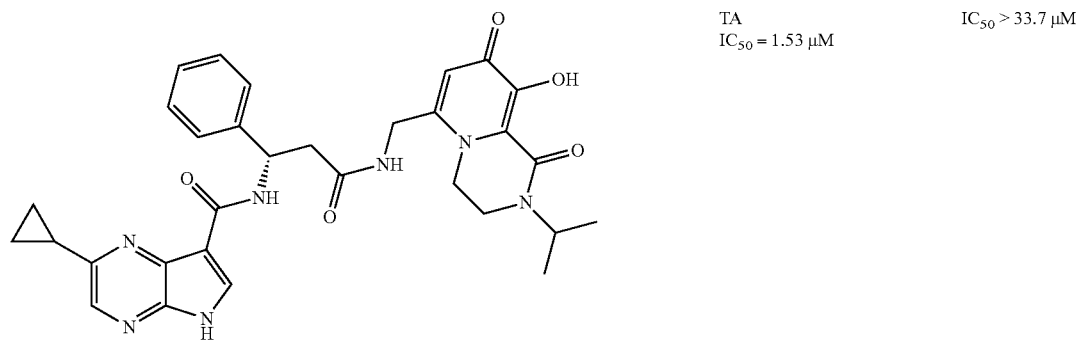
TA
IC$_{50}$ = 1.53 μM
IC$_{50}$ > 33.7 μM
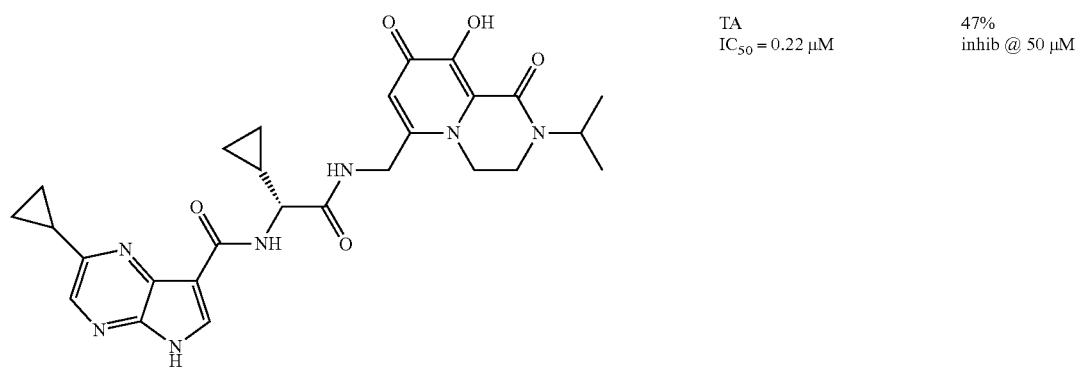
TA
IC$_{50}$ = 0.22 μM
47%
inhib @ 50 μM

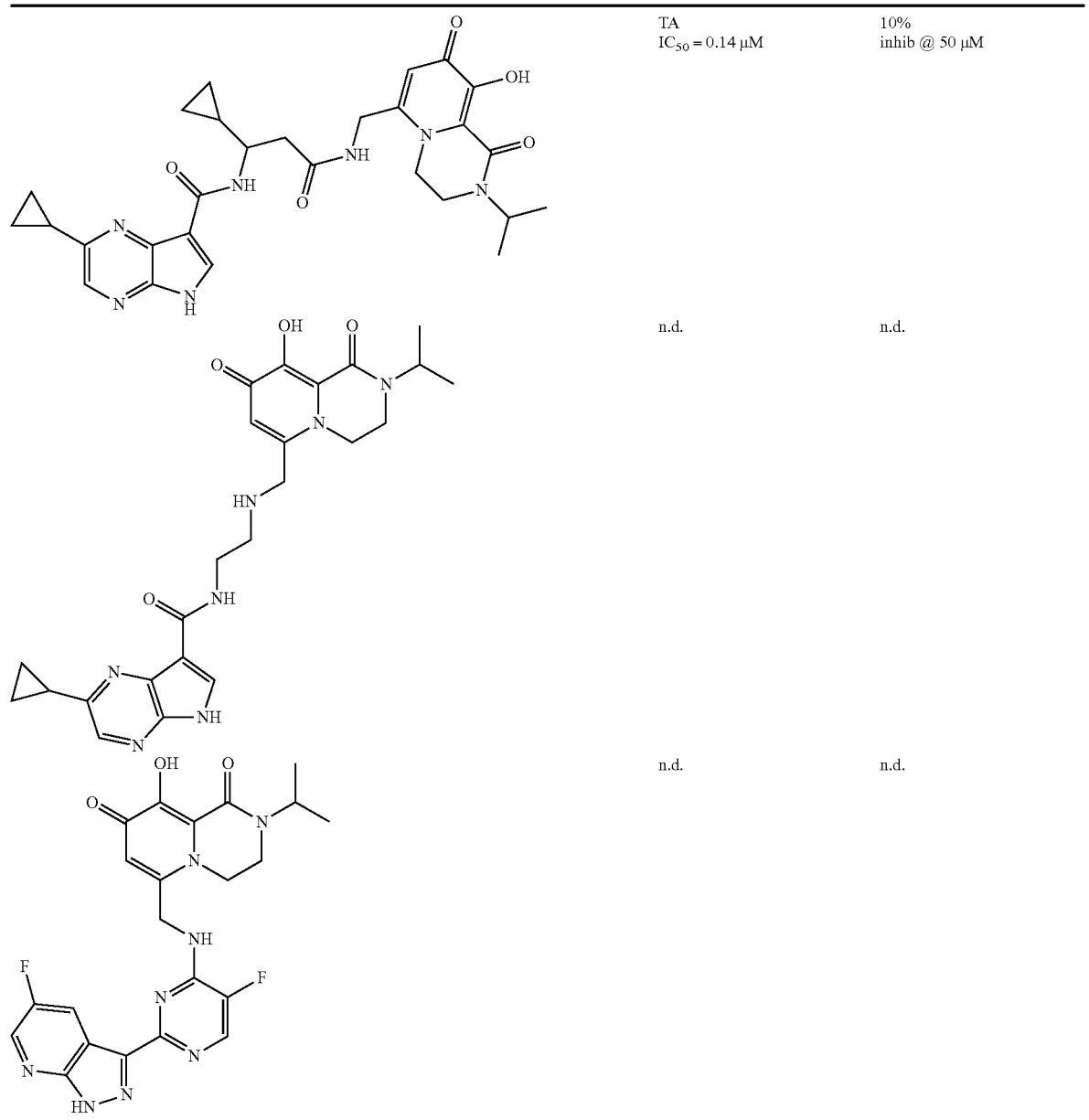
| | TA IC$_{50}$ = 0.14 µM | 10% inhib @ 50 µM |
| --- | --- | --- |
| | n.d. | n.d. |
| | n.d. | n.d. |
Synthesis Examples
In the following, the compounds were prepared according to the general schemes, unless a specific synthesis method is given.
D-1-01
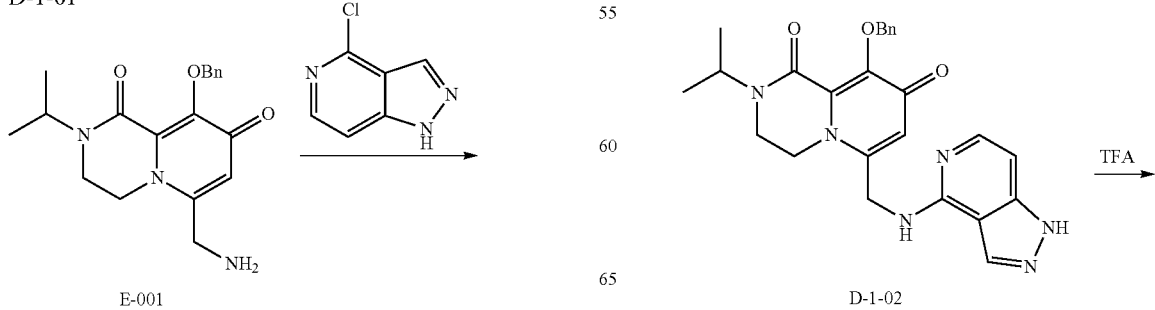

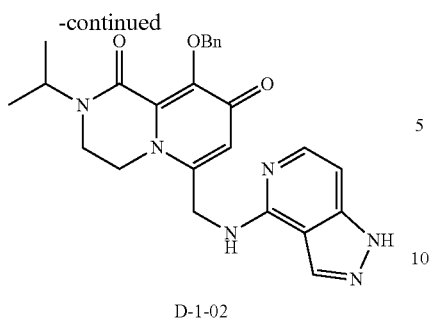

D-1-02

Synthesis of D-01-02

A mixture of tert-butyl 4-chloro-1H-pyrazolo[4,3-c]pyridine (30.6 mg, 0.2 mmol) and E-001 (68 mg, 0.2 mmol) was heated at 100° C. overnight. MeOH (2 mL) was added and the resultant was purified by Prep-TLC (ethyl acetate/petroleum ether=1/1) to give D-01-02 (50 mg, 54.5%) as a yellow oil.

Synthesis of D-1-01:

To a solution of D-01-02 (50 mg, 0.1 mmol) in DCM (2 mL) was added TFA (2 mL). The solution was stirred at r.t. until the disappearance of D-01-02 according to LCMS. The resultant was then concentrated under the reduced pressure and the residue was purified by Prep-HPLC to afford the product D-1-01 (24.8 mg, 61%) as pale a yellow solid.

6-((1H-pyrazolo[4,3-c]pyridin-4-ylamino)methyl)-9-hydroxy-2-isopropyl-3,4-dihydro-1H-pyrido[1,2-a]pyrazine-1,8(2H)-dione

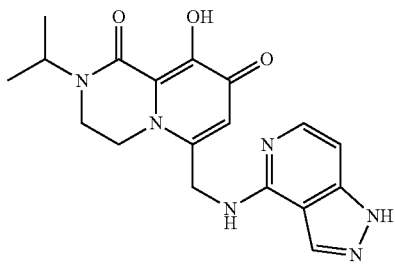 [SMILES: CC(C)N1CCn2c(CNc3nccc4[nH]ncc34)cc(=O)c(O)c2C1=O]

D-1-01 was obtained as a pale yellow solid
Yield: 33%
Mp:
MS (ESI): 369 (M+H)$^+$
1H NMR (d$_6$-DMSO, 400 Hz):
δ 8.63 (s, 1H), 7.67-7.68 (m, 1H), 7.22 (d, J=7.2 Hz, 1H), 6.50 (s, 1H), 4.87 (s, 2H), 4.75-4.79 (m, 1H), 4.29 (s, 2H), 3.71 (s, 2H), 1.22 (d, J=6.8 Hz, 6H).

D-2-01:

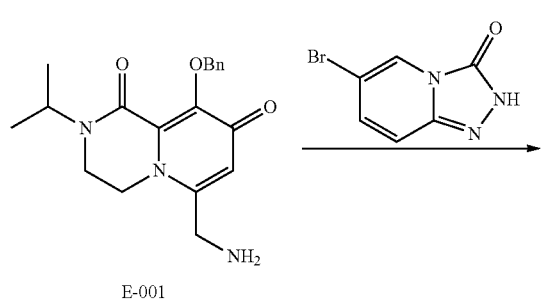

E-001

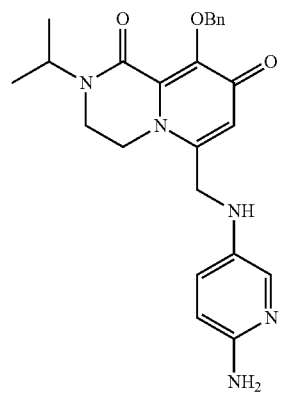 [SMILES: CC(C)N1CCn2c(CNc3ccc(N)nc3)cc(=O)c(OCc3ccccc3)c2C1=O]

D-2-01

Synthesis of D-2-01:

A mixture of 6-bromo-[1,2,4]triazolo[4,3-a]pyridin-3(2H)-one (21.4 mg, 0.1 mmol) and E-001 (34 mg, 0.1 mmol) was heated at 100° C. overnight. MeOH (2 mL) was added and the resultant was purified by Prep-TLC (ethyl acetate/petroleum ether=1/1) to give D-2-01 (1.5 mg, 3.5%) as a white solid.

6-((6-aminopyridin-3-ylamino)methyl)-9-(benzyloxy)-2-isopropyl-3,4-dihydro-1H-pyrido[1,2-a]pyrazine-1,8(2H)-dione

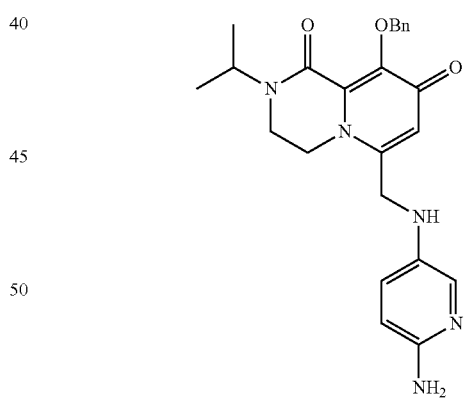

D-2-01 was obtained as a white solid
Yield: 3.5%
Mp:
MS (ESI): 432 (M−H)$^+$
1H NMR (CD$_3$OD, 400 Hz):
δ 7.45-7.47 (m, 2H), 7.31-7.36 (m, 6H), 7.25-7.27 (m, 1H), 6.59 (s, 1H), 5.18 (s, 2H), 4.71-4.74 (m, 1H), 4.24-4.26 (m, 2H), 3.81 (s, 2H), 3.76 (s, 2H), 3.40-3.43 (m, 2H), 1.21 (d, J=6.8 Hz, 6H)

D-2-02:

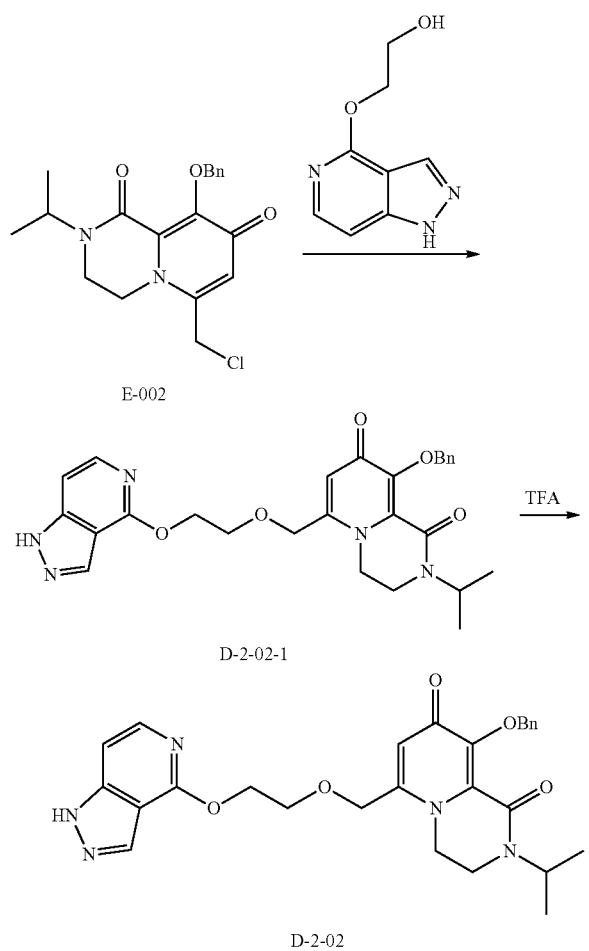

Synthesis of D-2-02-1:

To a mixture of 2-(1H-pyrazolo[4,3-c]pyridin-4-yloxy) ethanol (36 mg, 0.2 mmol) in DMF (2 mL) was added NaH (7.6 mg, 0.3 mmol) and E-002 (68 mg, 0.2 mmol). The mixture was stirred at 30° C. for 3 h. The resultant was purified by Prep-TLC (ethyl acetate/petroleum ether=1/1) to give D-2-02-1 (50 mg, 50%) as yellow oil.

Synthesis of D-2-02:

In the same manner as D-1-01, purification by Prep-HPLC afforded D-2-02 (5.8 mg, 1.3%) as brown oil.

6-((2-(1H-pyrazolo[4,3-c]pyridin-4-yloxy)ethoxy) methyl)-9-hydroxy-2-isopropyl-3,4-dihydro-1H-pyrido[1,2-a]pyrazine-1,8(2H)-dione

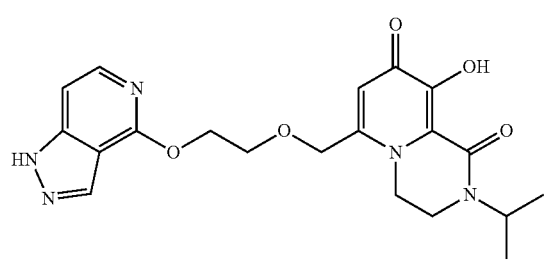 [SMILES: CC(C)N1CCn2c(COCCOc3nccc4[nH]ncc34)cc(=O)c(O)c2C1=O]

D-2-02 was obtained as a brown solid
Yield: 0.7%

Mp:

MS (ESI): 414 (M+H)+

1H NMR (CD3OD, 400 Hz):

δ 8.35 (s, 1H), 7.98 (s, 1H), 7.27 (br, 1H), 6.32 (s, 1H), 5.95 (s, 2H), 4.85-4.93 (m, 1H), 4.60-4.62 (m, 4H), 3.99 (t, J=4.4 Hz, 2H), 3.81 (s, 2H), 1.30 (d, J=6.8 Hz, 6H).

D-2-03:

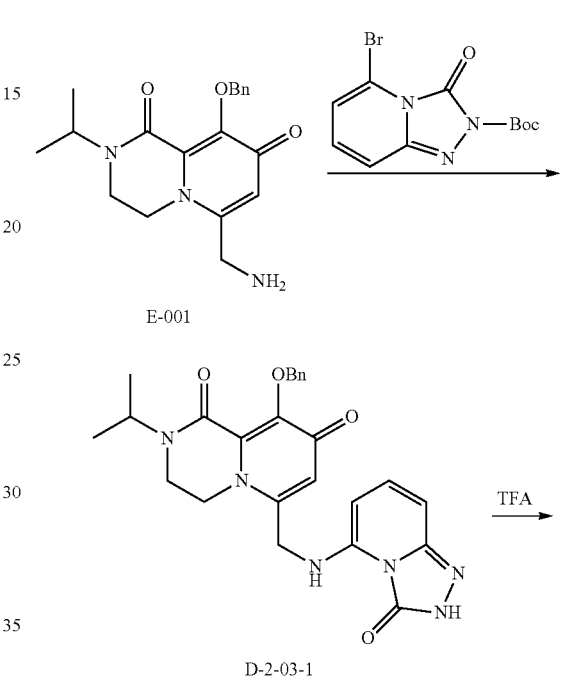

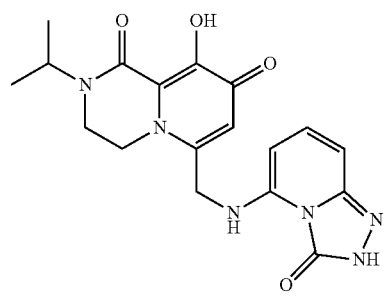

Synthesis of D-2-03-1:

A mixture of E-001 (68 mg, 0.2 mmol) and tert-butyl 5-bromo-3-oxo-[1,2,4]triazolo[4,3-a]pyridine-2(3H)-carboxylate (62.8 mg, 0.2 mmol) Pd(dppf)Cl2 (5 mg), Cs2CO3 (130 mg, 0.4 mmol) in 1,4-dioxane (3 ml) was stirred at 155° C. for 50 min. The resultant was purified by column chromatograph (ethyl acetate/petroleum ether=1/1) over silica gel to give DUAL-008-1 (35 mg, 13%) as a yellow oil.

Synthesis of D-2-03:

In the same manner as D-1-01, purification by Prep-HPLC afforded D-2-03 (6.9 mg, 29.6%) as a brown solid.

9-hydroxy-2-isopropyl-6-((3-oxo-2,3-dihydro-[1,2,4] triazolo[4,3-a]pyridin-5-ylamino)methyl)-3,4-dihydro-1H-pyrido[1,2-a]pyrazine-1,8(2H)-dione

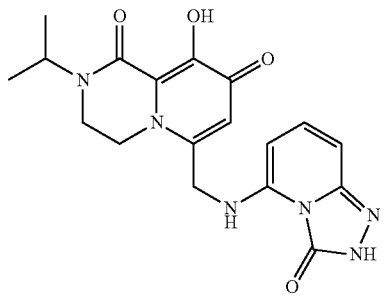 [SMILES: CC(C)N1CCn2c(CNc3cccc4n[nH]c(=O)n34)cc(=O)c(O)c2C1=O]

D-2-03 was obtained as a brown solid
Yield: 3.8%
Mp:
MS (ESI): 385 (M+H)+
1H NMR (d6-DMSO, 400 Hz):
δ 12.39 (s, 1H), 8.35 (s, 1H), 6.93-6.95 (m, 1H), 6.28-6.31 (m, 2H), 6.29 (d, J=7.2 Hz, 1H), 4.72-4.75 (m, 1H), 4.49 (s, 2H), 4.19 (s, 2H), 3.64 (s, 2H), 1.19 (d, J=6.8 Hz, 6H),
D-2-04:

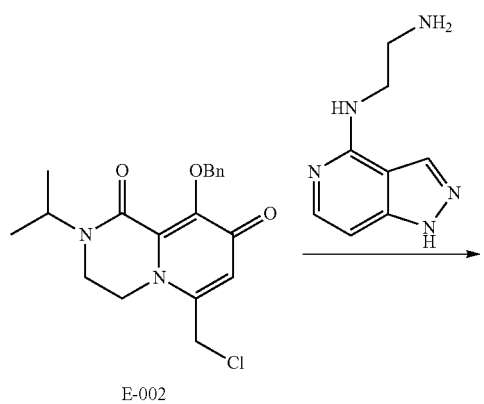

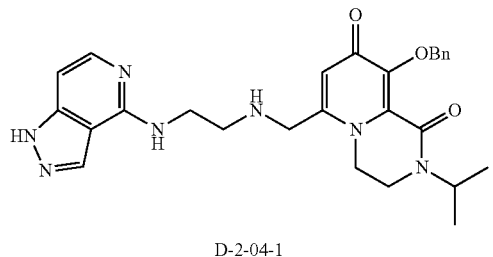

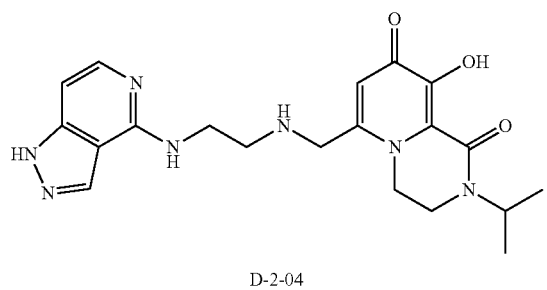

Synthesis of D-2-04-1:
To a mixture of N1-(1H-pyrazolo[4,3-c]pyridin-4-yl) ethane-1,2-diamine (35.4 mg, 0.2 mmol) in DMF (2 mL) was added K2CO3 (40 mg, 0.3 mmol) and E-002 (68 mg, 0.2 mmol). The mixture was stirred at 30° C. for 3 h. The resultant was purified by Prep-TLC (ethyl acetate/petroleum ether=1/1) to give D-2-04-1 (50 mg, 50%) as brown oil.

Synthesis of D-2-04:
In the same manner as D-1-01, purification by Prep-HPLC afforded D-2-04 (5.8 mg, 1.3%) as a brown solid.

6-((2-(1H-pyrazolo[4,3-c]pyridin-4-ylamino)ethylamino)methyl)-9-hydroxy-2-isopropyl-3,4-dihydro-1H-pyrido[1,2-a]pyrazine-1,8(2H)-dione

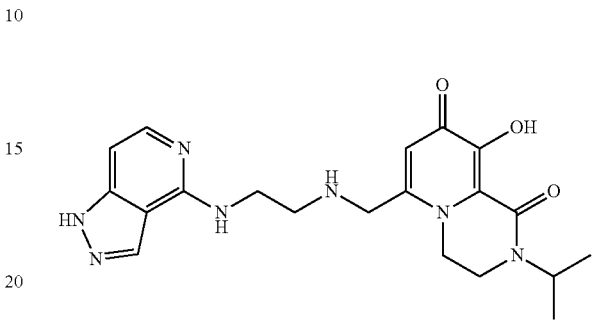

D-2-04 was obtained as brown solid
Yield: 0.7%
Mp:
MS (ESI): 412 (M+H)+
1H NMR (CD3OD, 400 Hz):
δ 8.50 (s, 1H), 7.62 (d, J=6.8 Hz, 1H), 7.12 (d, J=6.8 Hz, 1H), 6.80 (s, 1H), 4.52-4.60 (m, 1H), 4.46 (s, 2H), 4.29 (s, 2H), 4.01 (s, 2H), 3.73 (s, 2H), 3.52 (s, 2H), 1.28 (d, J=6.8 Hz, 6H).
D-3-01-2:

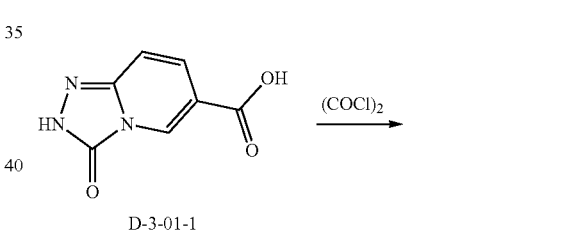

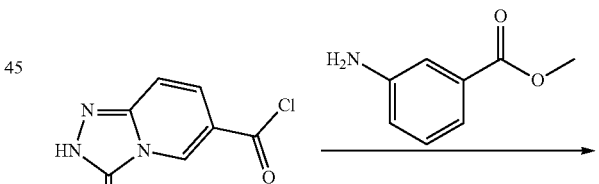

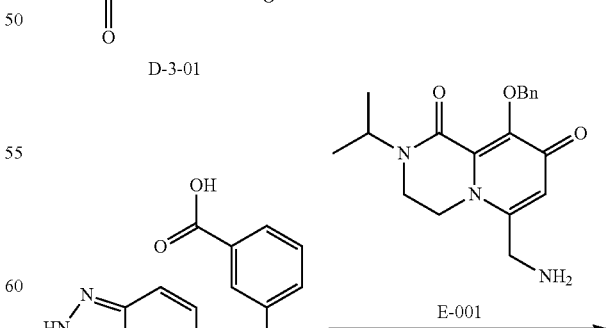

-continued

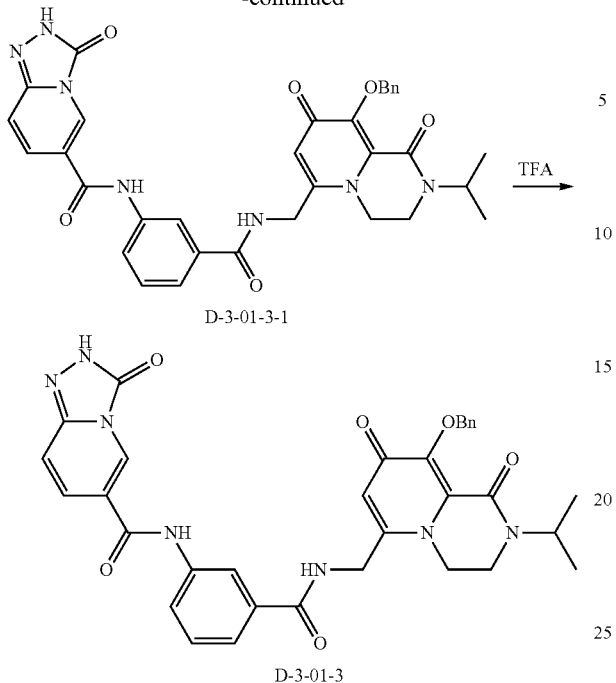

D-3-01-3-1

D-3-01-3

Synthesis of D-3-01:

To a solution of 3-oxo-2,3-dihydro-[1,2,4]triazolo[4,3-a]pyridine-6-carboxylic acid (50 mg, 0.28 mmol) in DCM (5 mL) was added oxalyl dichloride (71 mg, 0.56 mmol) and DMF (1 drop) successively. The reaction mixture was stirred at r.t. for 3 h. Concentration under the reduced pressure to give crude D-3-01 (50 mg, 91%), which was used directly for the next step.

Synthesis of D-3-01-3-3:

To a solution of ethyl methyl 3-aminobenzoate (38 mg, 0.25 mmol), TEA (50 mg, 0.50 mmol) in DCM (5 mL) was added D-3-01 (50 mg, 0.25 mmol) dropwise. The solution was stirred at r.t overnight and then concentrated. The residue was purified by Prep-TLC (MeOH/DCM=1/15) to give D-3-01-3-3 (59 mg, 76%) as yellow oil.

Synthesis of D-3-01-3-2:

A mixture of D-3-01-3-3 (59 mg, 0.19 mmol) and LiOH (9 mg, 0.38 mmol) in MeOH (3 mL) was stirred at r.t. overnight. The solvent was removed in vacuo. Water was added and the pH of the solution was adjusted to 5 with 2N HCl. The resultant was filtered and the solid was washed over water to give D-3-01-3-2 (41 mg, 77%) as pale yellow solid.

Synthesis of D-3-01-3-1:

A mixture of D-3-01-3-2 (41 mg, 0.15 mmol) and HATU (68 mg, 0.18 mmol) in DMF (3 mL) was stirred at r.t. for 0.5 h. After that, TEA (30 mg, 0.30 mmol) and E-001 (51 mg, 0.15 mmol) was added. The reaction mixture was stirred at r.t. overnight. The resultant was purified by Prep-TLC to give D-3-01-3-1 (29.5 mg, 36%) as yellow oil.

Synthesis of D-3-01-3:

In the same manner as D-1-01, purification by Prep-HPLC afforded D-3-01-1 (2.5 mg, 10%) as a brown solid.

N-(3-((9-hydroxy-2-isopropyl-1,8-dioxo-2,3,4,8-tetrahydro-1H-pyrido[1,2-a]pyrazin-6-yl)methylcarbamoyl)phenyl)-3-oxo-2,3-dihydro-[1,2,4]triazolo[4,3-a]pyridine-6-carboxamide

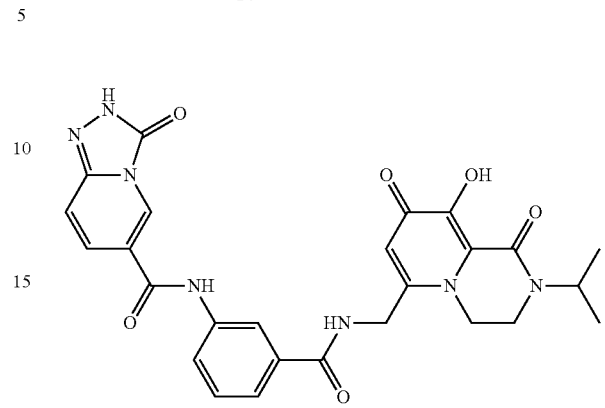

D-3-01-3 was obtained as a brown solid.

Yield: 1.6%

Mp:

MS (ESI): 532 (M+H)$^+$

1H NMR (d$_6$-DMSO, 400 Hz):

δ 12.70 (s, 1H), 10.54 (s, 1H), 9.10 (s, 1H), 8.76 (s, 1H), 8.27 (s, 1H), 7.97 (d, J=8.0 Hz, 1H), 7.60-7.67 (m, 2H), 7.50 (t, J=8.0 Hz, 1H), 7.32 (d, J=10.0 Hz, 1H), 6.41 (s, 1H), 4.70-4.75 (m, 1H), 4.56 (s, 2H), 4.29 (s, 2H), 3.76 (s, 2H), 1.18 (d, J=6.8 Hz, 6H).

D-3-01-4:

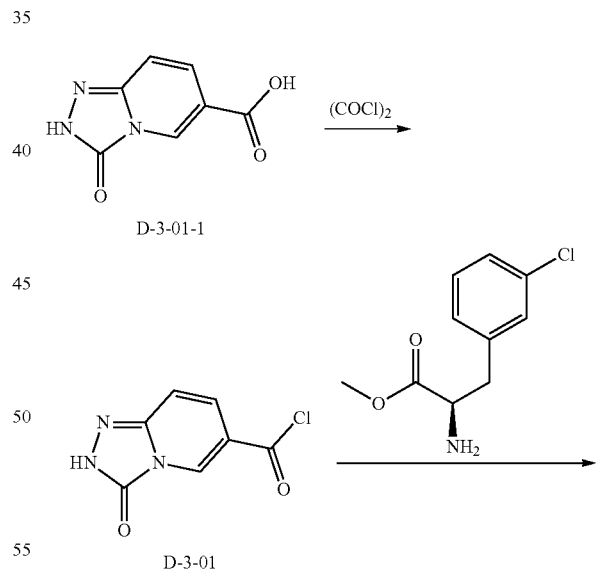

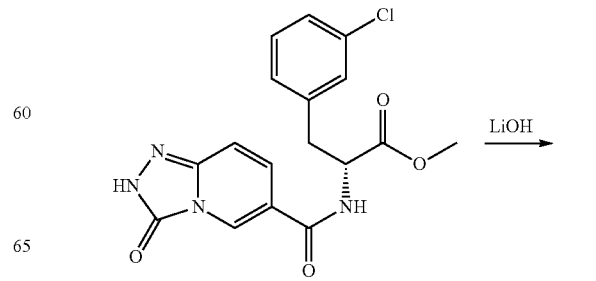

-continued

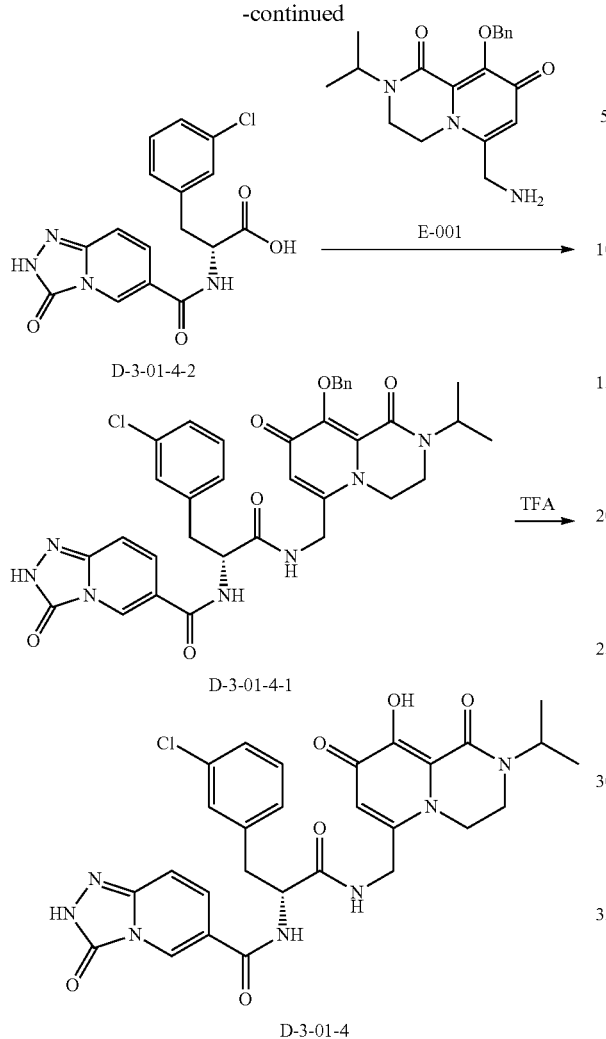

D-3-01-4 was synthesized in the same manner as D-3-01-3. Purification by Prep-HPLC afforded D-3-01-4 (2.2 mg, 8%) as a brown solid.

(R)—N-(3-(3-chlorophenyl)-1-((9-hydroxy-2-isopropyl-1,8-dioxo-2,3,4,8-tetrahydro-1H-pyrido[1,2-a]pyrazin-6-yl)methylamino)-1-oxopropan-2-yl)-3-oxo-2,3-dihydro-[1,2,4]triazolo[4,3-a]pyridine-6-carboxamide

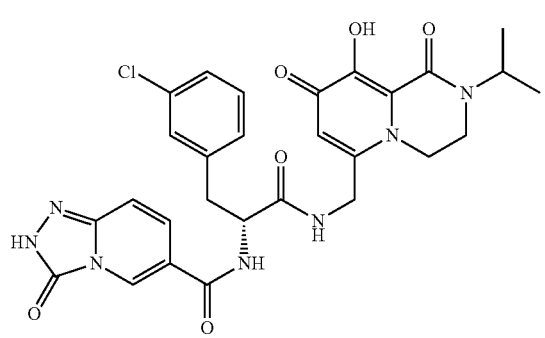 [SMILES: CC(C)N1CCn2c(CNC(=O)[C@@H](Cc3cccc(Cl)c3)NC(=O)c3ccc4n[nH]c(=O)n4c3)cc(=O)c(O)c2C1=O]

D-3-01-4 was obtained as a brown solid.
Yield: 1.3%

Mp:
MS (ESI): 594 (M+H)$^+$
1H NMR (d$_6$-DMSO, 400 Hz):
δ 12.65 (br, 1H), 8.93-8.98 (m, 1H), 8.73-8.75 (m, 1H), 7.35-7.51 (m, 2H), 7.23-7.28 (m, 6H), 5.32 (t, J=4.8 Hz, 1H), 4.66-4.73 (m, 2H), 4.37-4.46 (m, 2H), 4.03 (br, 1H), 3.07-3.12 (m, 2H), 2.97-3.03 (m, 2H), 1.17 (d, J=7.2 Hz, 6H).

D-3-01-5:

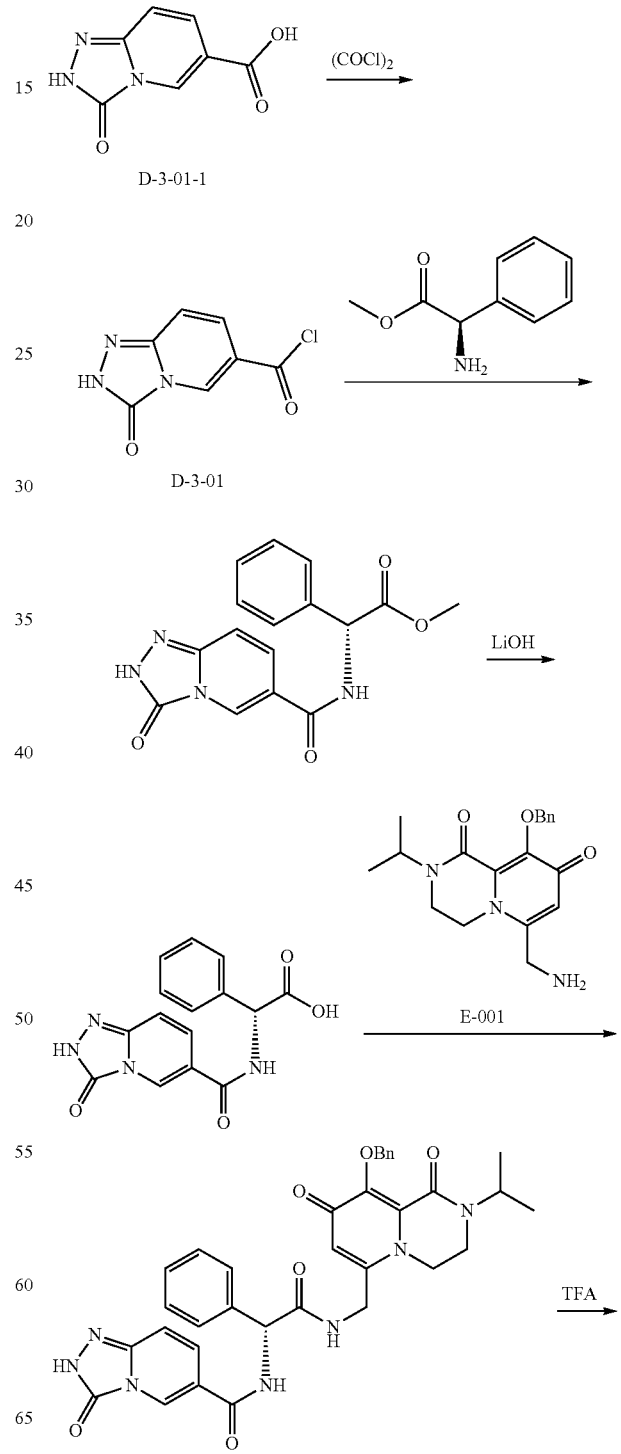

-continued

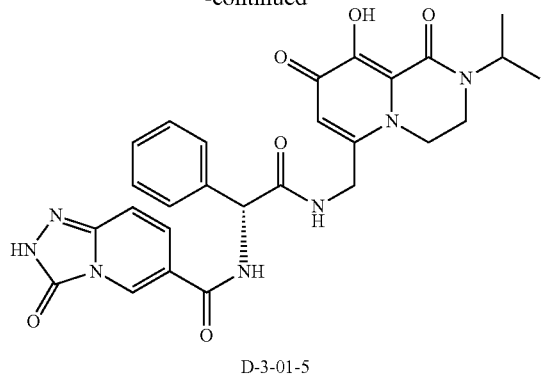

D-3-01-5

D-3-01-5 was synthesized in the same manner as D-3-01-3. Purification by Prep-HPLC afforded D-3-01-5 (3.3 mg, 13%) as a brown solid.

(R)—N-(2-((9-hydroxy-2-isopropyl-1,8-dioxo-2,3,4,8-tetrahydro-1H-pyrido[1,2-a]pyrazin-6-yl)methylamino)-2-oxo-1-phenylethyl)-3-oxo-2,3-dihydro-[1,2,4]triazolo[4,3-a]pyridine-8-carboxamide

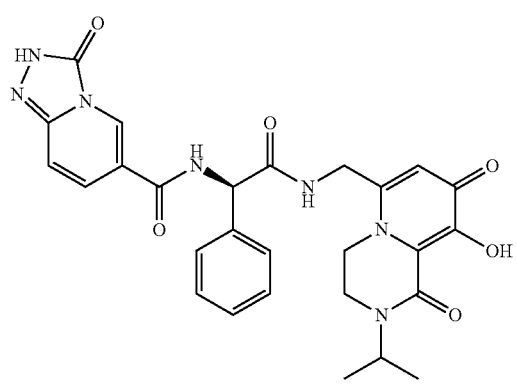 [SMILES: CC(C)N1CCn2c(CNC(=O)[C@H](NC(=O)c3ccc4n[nH]c(=O)n4c3)c3ccccc3)cc(=O)c(O)c2C1=O]

D-3-01-5 was obtained as a brown solid.
Yield: 1.3%
Mp:
MS (ESI): 546 (M+H)$^+$
1H NMR (CD$_3$OD, 400 Hz):
δ 8.38 (br, 1H), 7.44-7.58 (m, 2H), 7.21-7.38 (m, 5H), 7.09 (br, 1H), 5.42 (br, 1H), 5.24 (t, J=4.4 Hz, 1H), 4.41 (br, 2H), 4.00-4.16 (m, 2H), 3.40-3.53 (m, 2H), 1.18-1.20 (m, 6H).

D-3-02-1:

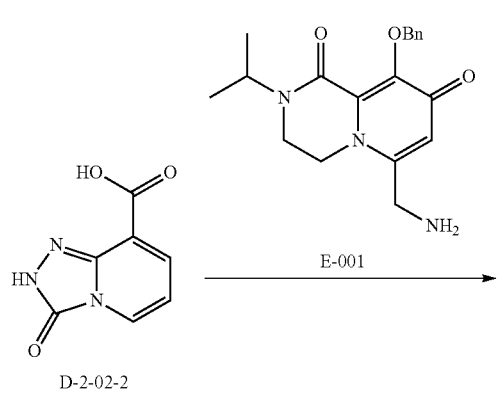

D-2-02-2 → E-001

-continued

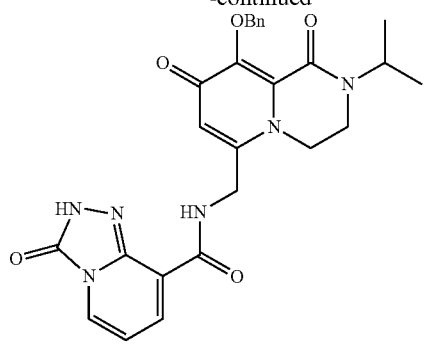

D-2-02-1-1

TFA →

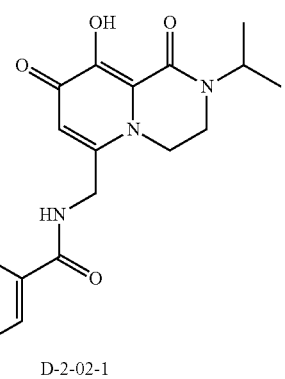

D-2-02-1

D-3-02-1-1 was synthesized in the similar manner as D-3-01-3. Purification by Prep-HPLC afforded D-3-02-1 (9.5 mg, 38%) as yellow solid.

N-((9-hydroxy-2-isopropyl-1,8-dioxo-2,3,4,8-tetrahydro-1H-pyrido[1,2-a]pyrazin-6-yl)methyl)-3-oxo-2,3-dihydro-[1,2,4]triazolo[4,3-a]pyridine-8-carboxamide

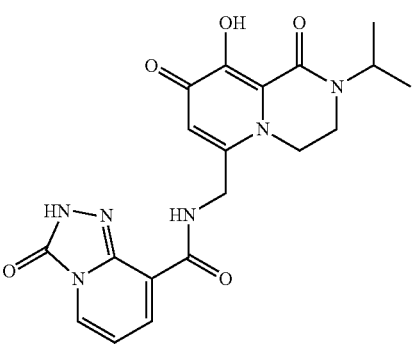 [SMILES: CC(C)N1CCn2c(CNC(=O)c3cccn4c(=O)[nH]nc34)cc(=O)c(O)c2C1=O]

D-3-02-1 was obtained as yellow solid.
Yield: 7%
Mp:
MS (ESI): 413 (M+H)$^+$
1H NMR (CD$_3$OD, 400 Hz):
δ 8.09 (d, J=6.4 Hz, 2H) 7.02 (s, 1H), 6.85 (t, J=6.8 Hz, 1H), 4.90-4.93 (m, 1H), 4.81 (s, 2H), 4.56 (s, 2H), 3.81 (s, 2H), 1.30 (d, J=6.8 Hz, 6H).

D-3-02-3:

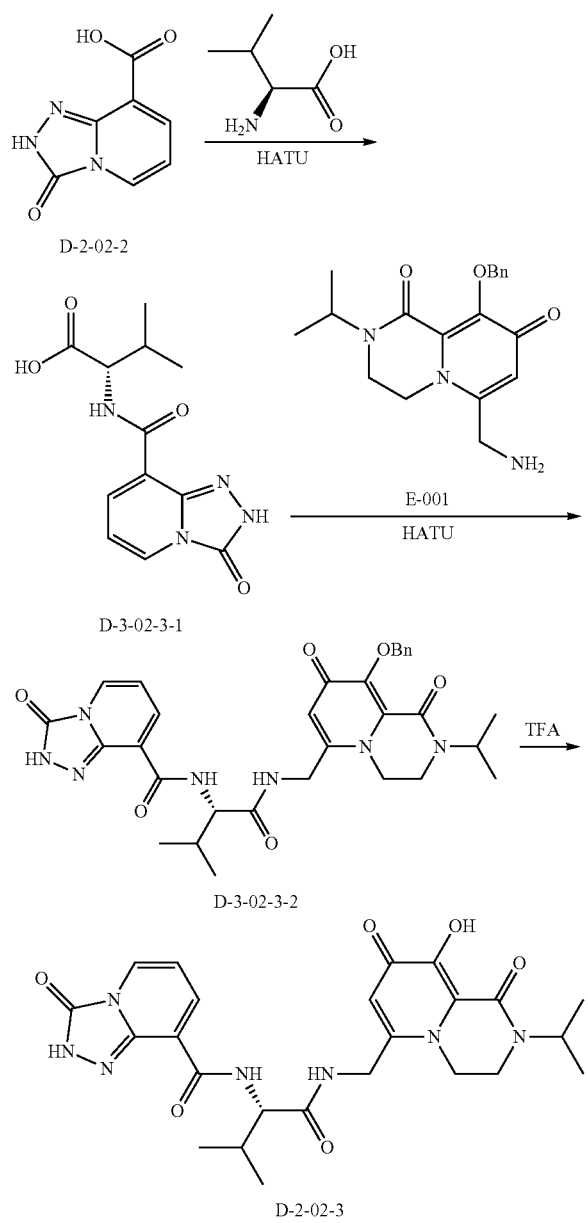

N-(1-((9-hydroxy-2-isopropyl-1,8-dioxo-2,3,4,8-tetrahydro-1H-pyrido[1,2-a]pyrazin-6-yl)methylcarbamoyl)cyclohexyl)-3-oxo-2,3-dihydro-[1,2,4]triazolo[4,3-a]pyridine-8-carboxamide

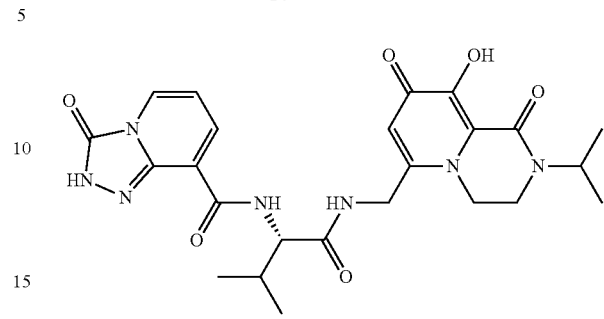

D-3-02-3 was obtained as pale a pale yellow solid.
Yield: 4%
Mp:
MS (ESI): 512 (M+H)$^+$
1H NMR (d$_6$-DMSO, 400 Hz):
δ 12.93 (s, 1H), 8.85 (t, J=4.8 Hz, 1H), 8.81 (d, J=8.4 Hz, 1H), 8.10 (d, J=5.6 Hz, 1H), 7.97 (d, J=6.4 Hz, 1H), 6.78 (d, J=6.8 Hz, 1H), 6.51 (s, 1H), 4.70-4.73 (m, 1H), 4.53-4.56 (m, 1H), 4.43 (s, 2H), 4.24 (s, 2H), 3.63 (s, 2H), 2.15-2.16 (m, 1H), 1.13-1.18 (m, 6H), 0.95 (d, J=6.4 Hz, 6H).

D-3-02-4:

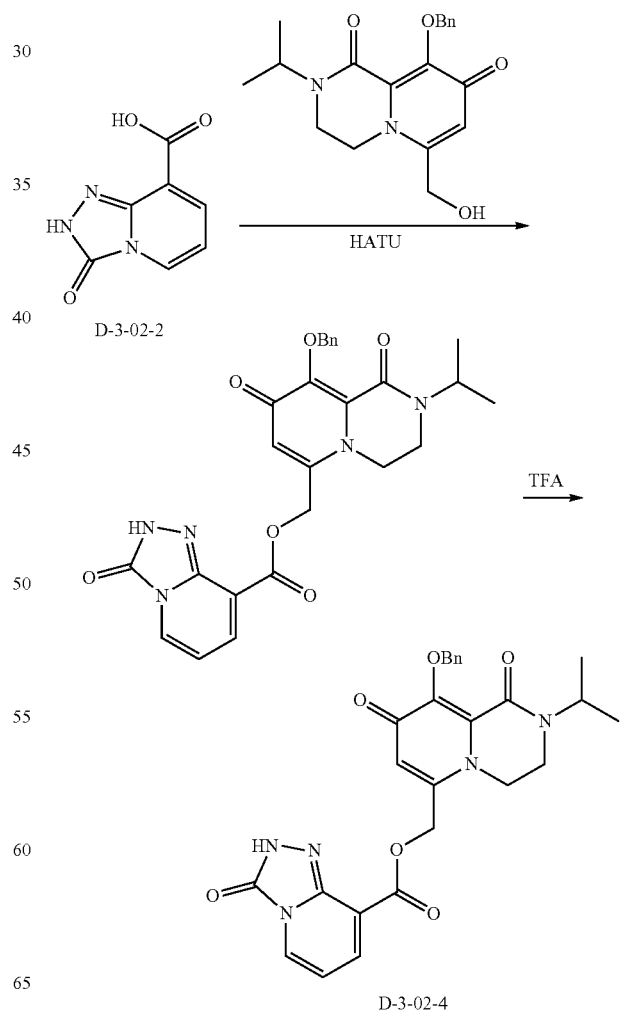

Synthesis of D-3-02-3-2:

A mixture of D-3-02-2 (60 mg, 0.33 mmol) and HATU (153 mg, 0.40 mmol) in DMF (3 mL) was stirred at r.t. for 0.5 h. After that, TEA (67 mg, 0.66 mmol) and 1-aminocyclohexanecarboxylic acid (47 mg, 0.33 mmol) was added successively. The reaction mixture was stirred at r.t. for 3 h. The resultant was filtered and the filtration was concentrated to give crude D-3-02-3-1. To the solution of crude D-3-02-3-1 in DMF (3 mL) was added TEA (67 mg, 0.66 mmol), HATU (153 mg, 0.40 mmol) and E-001 (112 mg, 0.33 mmol) successively. The mixture was stirred at r.t. overnight and then concentrated. The residue was purified by Prep-TLC (MeOH/DCM=1/10) to give D-3-02-3-2 (30 mg, 14%) as yellow oil.

Synthesis of D-3-02-3:

In the same manner as D-1-01, purification by Prep-HPLC afforded D-3-02-3 (8 mg, 31%) as a pale yellow solid.

D-3-02-4 was synthesized in the similar manner as D-3-01-3. Purification by Prep-HPLC afforded D-3-02-4 (6.5 mg, 26%) as a yellow solid.

(9-Hydroxy-2-isopropyl-1,8-dioxo-2,3,4,8-tetrahydro-1H-pyrido[1,2-a]pyrazin-6-yl)methyl-3-oxo-2,3-dihydro-[1,2,4]triazolo[4,3-a]pyridine-8-carboxylate

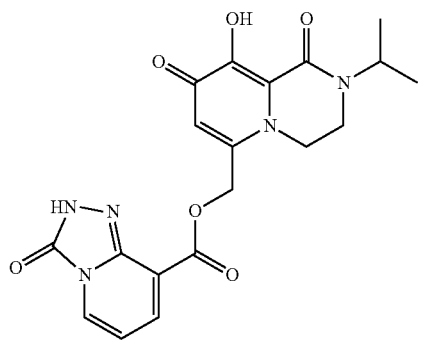 [SMILES: CC(C)N1CCn2c(COC(=O)c3cccn4c(=O)[nH]nc34)cc(=O)c(O)c2C1=O]

D-3-02-4 was obtained as a yellow solid.
Yield: 4.8%
Mp:
MS (ESI): 414 (M+H)$^+$
1H NMR (d$_6$-DMSO, 400 Hz):
δ 12.72 (s, 1H), 12.68 (br, 1H), 8.12 (d, J=7.2 Hz, 1H), 8.02 (d, J=6.0 Hz, 1H), 6.70 (t, J=6.8 Hz, 1H), 6.47 (s, 1H), 5.38 (s, 2H), 4.73-4.76 (m, 1H), 4.24-4.27 (m, 2H), 3.61-3.64 (m, 2H), 1.18 (d, J=6.8 Hz, 6H).

D-3-02-5:

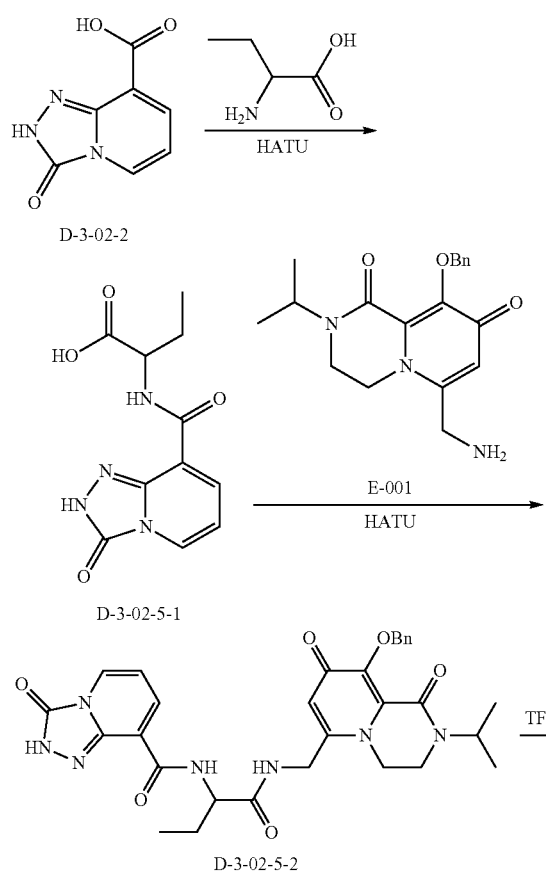

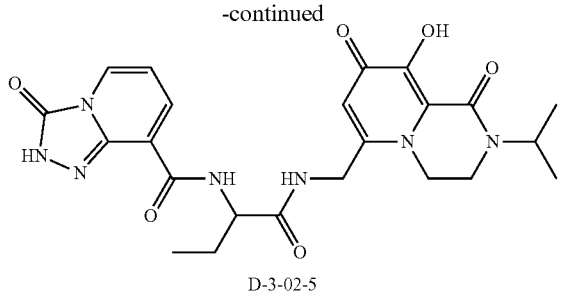

D-3-02-5 was synthesized in the similar manner as D-3-02-3. Purification by Prep-HPLC afforded D-3-02-5 (4.1 mg, 16%) as a pale yellow solid.

N-(1-((9-hydroxy-2-isopropyl-1,8-dioxo-2,3,4,8-tetrahydro-1H-pyrido[1,2-a]pyrazin-6-yl)methylamino)-1-oxobutan-2-yl)-3-oxo-2,3-dihydro-[1,2,4]triazolo[4,3-a]pyridine-8-carboxamide

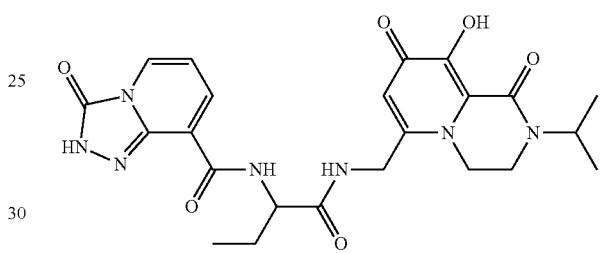

D-3-02-5 was obtained as a pale yellow solid.
Yield: 2.1%
Mp:
MS (ESI): 498 (M+H)$^+$
1H NMR (d$_6$-DMSO, 400 Hz):
δ 8.85 (d, J=7.2 Hz, 1H), 8.79 (s, 1H), 8.09 (d, J=6.0 Hz, 1H), 7.96 (d, J=6.0 Hz, 1H), 6.77 (t, J=6.4 Hz, 1H), 6.18 (s, 1H), 4.71-4.74 (m, 1H), 4.57-4.59 (m, 1H), 4.35 (s, 2H), 4.09 (s, 2H), 3.58 (s, 2H), 3.09-3.11 (m, 2H), 1.16-1.19 (m, 6H), 0.91 (d, J=7.2 Hz, 3H).

D-3-02-6:

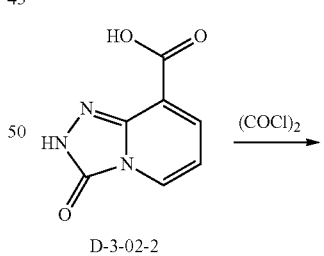

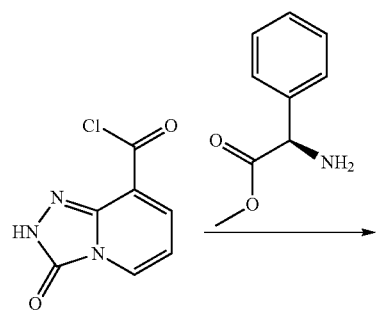

65

-continued

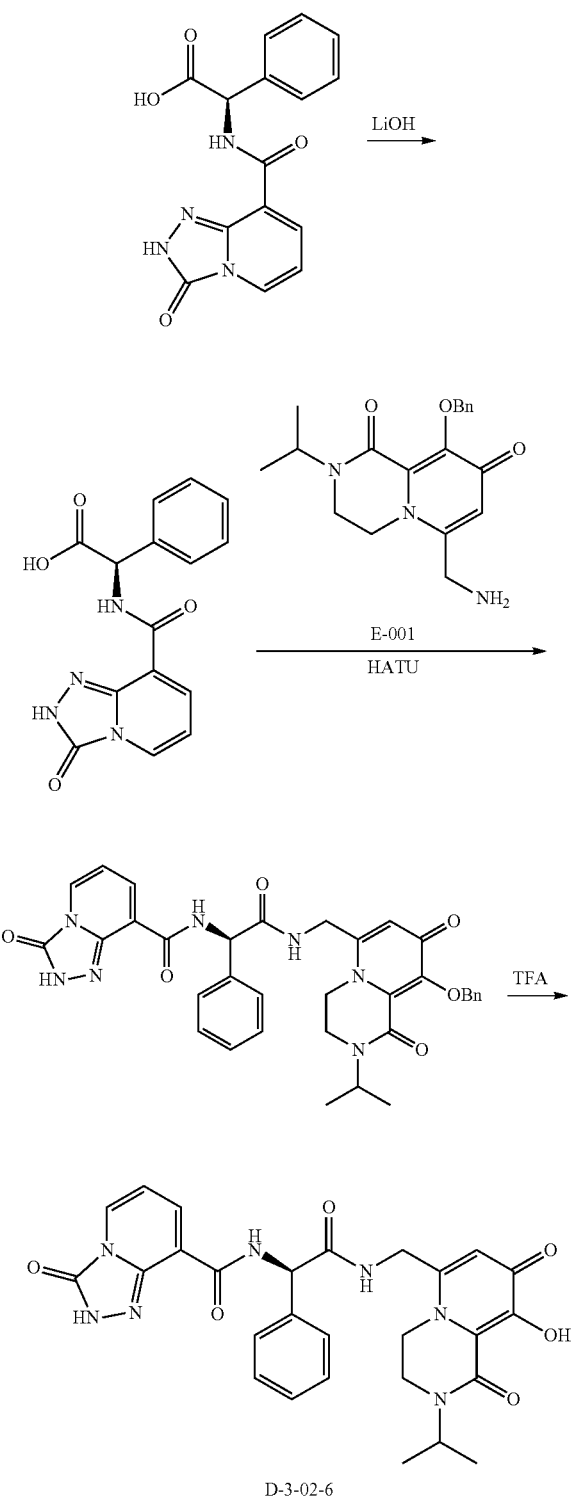

D-3-02-6 was synthesized in the similar manner as D-3-01-3. Purification by Prep-HPLC afforded D-3-02-6 (3.2 mg, 13%) as a brown solid.

66

(R)—N-(2-((9-hydroxy-2-isopropyl-1,8-dioxo-2,3,4,8-tetrahydro-1H-pyrido[1,2-a]pyrazin-6-yl)methylamino)-2-oxo-1-phenylethyl)-3-oxo-2,3-dihydro-[1,2,4]triazolo[4,3-a]pyridine-8-carboxamide

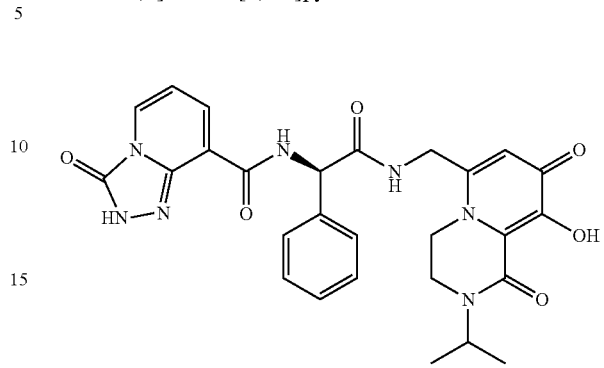

D-3-02-6 was obtained as a brown solid.

Yield: 1.3%

Mp:

MS (ESI): 546 (M+H)$^+$

1H NMR (d$_6$-DMSO, 400 Hz):

δ 12.91-12.94 (m, 1H), 9.45-9.49 (m, 1H), 9.08 (br, 1H), 8.09 (d, J=6.0 Hz, 1H), 7.94 (d, J=6.4 Hz, 1H), 7.37-7.49 (m, 6H), 6.76-6.78 (m, 1H), 5.68-5.70 (m, 1H), 4.69-4.72 (m, 1H), 4.42-4.48 (m, 2H), 3.92 (br, 2H), 3.82 (br, 2H), 1.12 (d, J=6.8 Hz, 6H).

(R)—N-(3-(3-chlorophenyl)-1-((9-hydroxy-2-isopropyl-1,8-dioxo-2,3,4,8-tetrahydro-1H-pyrido[1,2-a]pyrazin-6-yl)methylamino)-1-oxopropan-2-yl)-3-oxo-2,3-dihydro-[1,2,4]triazolo[4,3-a]pyridine-8-carboxamide

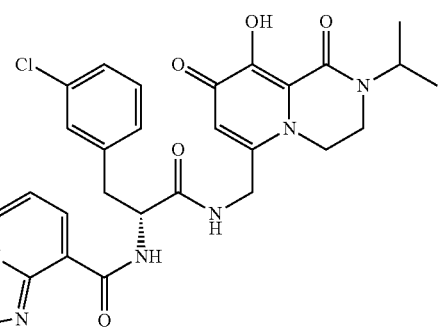

D-3-02-7 was obtained as brown solid in the same manner as D-3-01-3

Yield: 4.6%

Mp:

MS (ESI): 594 (M+H)$^+$

1H NMR (d$_6$-DMSO, 400 Hz):

δ 12.94 (s, 1H), 8.84 (d, J=7.2 Hz, 1H), 8.08 (d, J=7.2 Hz, 1H), 7.91 (d, J=6.8 Hz, 1H), 7.28 (s, 1H), 7.24 (s, 2H), 7.15 (s, 1H), 6.75 (d, J=6.8 Hz, 1H), 6.36 (s, 1H), 4.85-4.88 (m, 1H), 4.75-4.78 (m, 1H), 4.35 (s, 2H), 4.06 (s, 2H), 3.57 (s, 2H), 3.02-3.12 (m, 2H), 1.17 (d, J=6.8 Hz, 6H).

D-3-03-1:

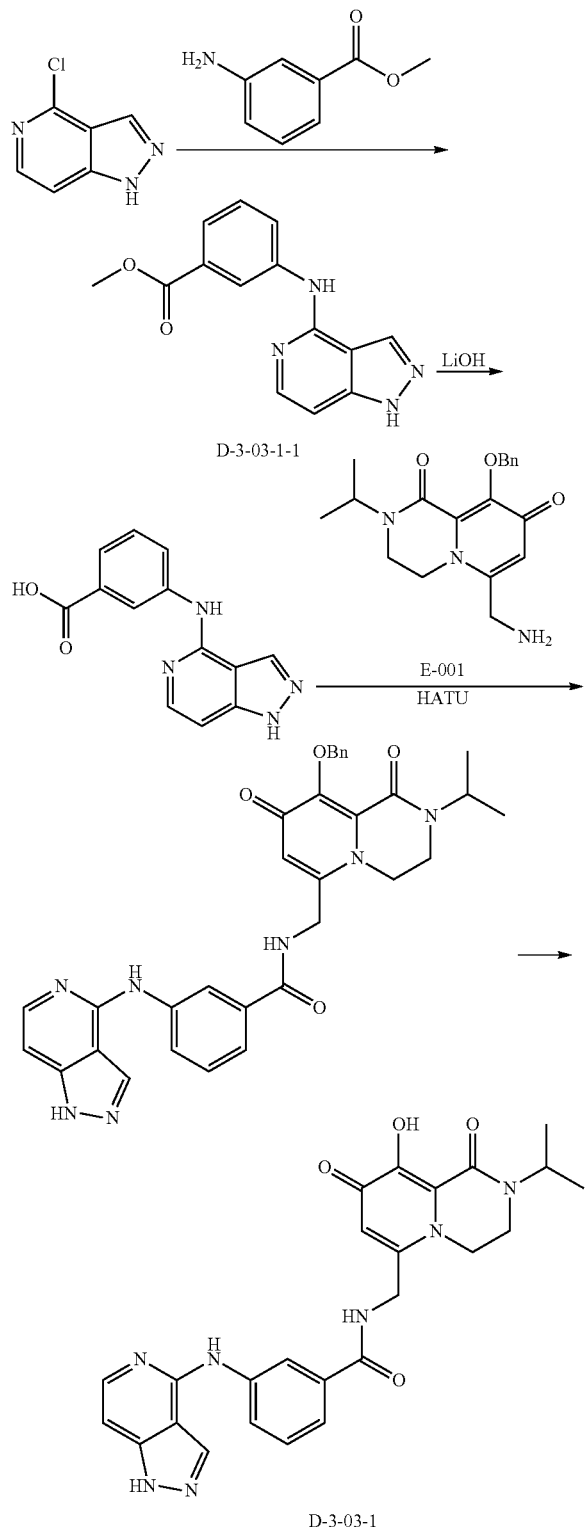

Synthesis of D-3-03-1:
A mixture of 4-chloro-1H-pyrazolo[4,3-c]pyridine (30.6 mg, 0.2 mmol) and methyl 3-aminobenzoate (30.2 mg, 0.2 mmol) was heated at 100° C. overnight. MeOH (2 mL) was added and the resultant was purified by Prep-TLC (ethyl acetate/petroleum ether=1/1) to give D-3-03-1-1 (38 mg, 71%) as a white solid.

In the following steps, D-3-03-1 was synthesized in the similar manner as D-3-01-3. Purification by Prep-HPLC afforded D-3-03-1 (2.8 mg, 13%) as a brown solid.

3-(1H-pyrazolo[4,3-c]pyridin-4-ylamino)-N-((9-(benzyloxy)-2-isopropyl-1,8-dioxo-2,3,4,8-tetrahydro-1H-pyrido[1,2-a]pyrazin-6-yl)methyl)benzamide

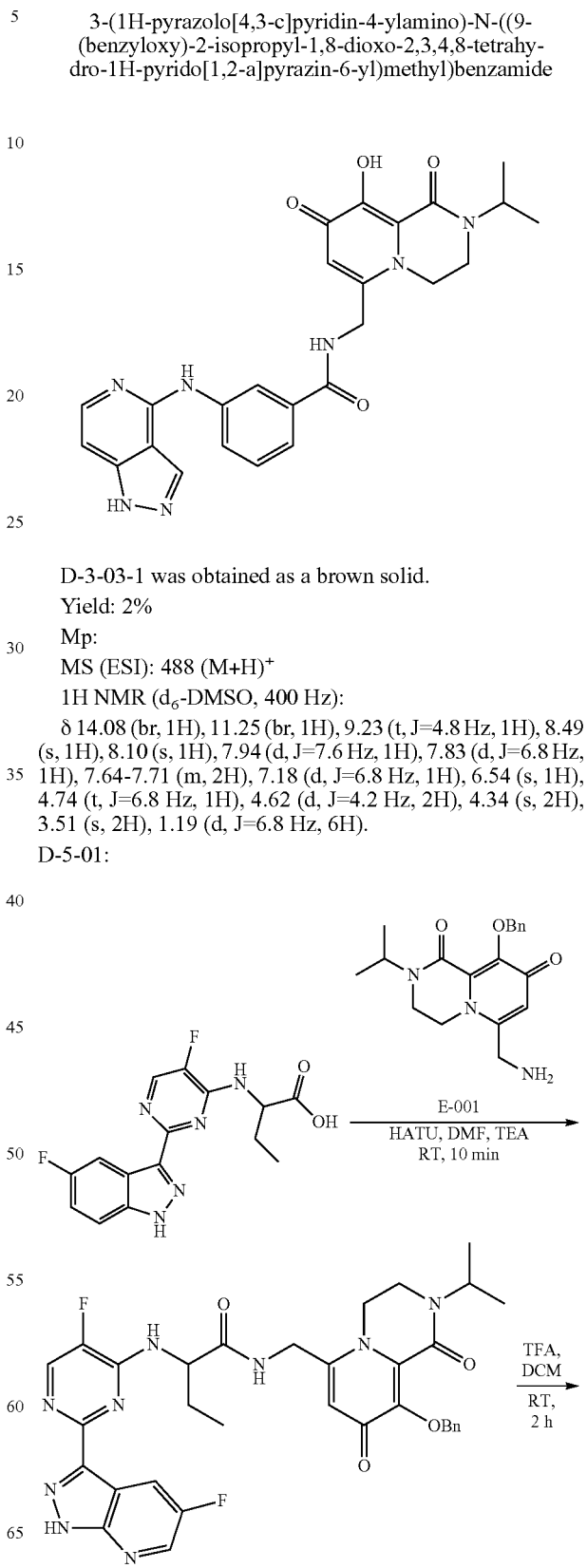

D-3-03-1 was obtained as a brown solid.
Yield: 2%
Mp:
MS (ESI): 488 (M+H)+
1H NMR (d$_6$-DMSO, 400 Hz):
δ 14.08 (br, 1H), 11.25 (br, 1H), 9.23 (t, J=4.8 Hz, 1H), 8.49 (s, 1H), 8.10 (s, 1H), 7.94 (d, J=7.6 Hz, 1H), 7.83 (d, J=6.8 Hz, 1H), 7.64-7.71 (m, 2H), 7.18 (d, J=6.8 Hz, 1H), 6.54 (s, 1H), 4.74 (t, J=6.8 Hz, 1H), 4.62 (d, J=4.2 Hz, 2H), 4.34 (s, 2H), 3.51 (s, 2H), 1.19 (d, J=6.8 Hz, 6H).

D-5-01:

69
-continued

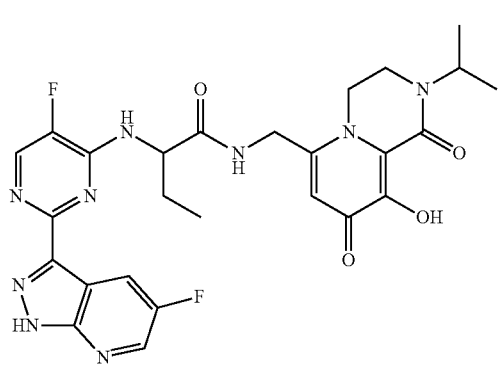

D-5-01

D-5-01 was synthesized in the similar manner as D-3-01-3. Purification by Prep-HPLC afforded D-5-01 (8.7 mg, 62%) as a pale yellow oil.

70

2-(5-fluoro-2-(5-fluoro-1H-pyrazolo[3,4-b]pyridin-3-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)butanamide

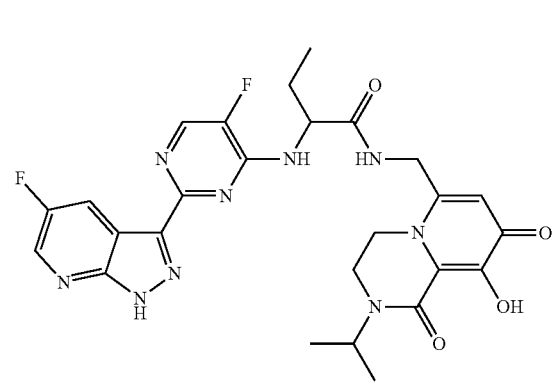 [SMILES: CCC(Nc1nc(-c2n[nH]c3ncc(F)cc23)ncc1F)C(=O)NCc1cc(=O)c(O)c2n1CCN(C(C)C)C2=O]

D-5-01 was obtained as a pale yellow oil.
Yield: 26%
Mp:
MS (ESI): 568 (M+H)$^+$
1H NMR (CD$_3$OD, 400 Hz):
δ 8.48 (s, 1H), 8.31 (s, 1H), 8.26 (d, J=7.6 Hz, 1H), 6.72 (s, 1H), 5.36 (t, J=4.8 Hz, 1H), 4.59-4.64 (m, 3H), 4.35-4.39 (m, 1H), 3.76-3.81 (m, 1H), 3.40-3.44 (m, 2H), 3.04-2.09 (m, 2H), 1.32 (d, J=6.8 Hz, 6H), 1.12 (t, J=7.2 Hz, 3H).
D-5-02:

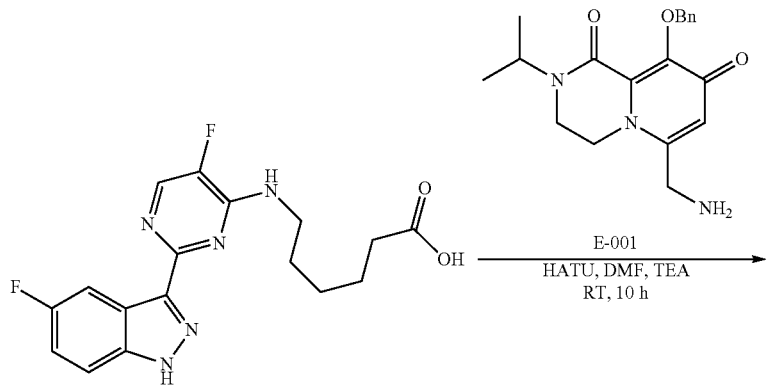

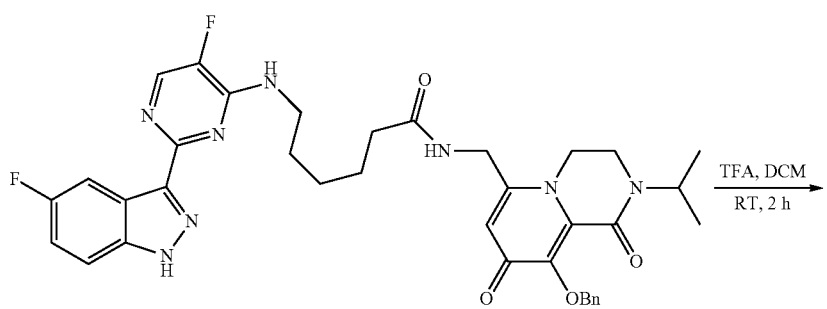

-continued

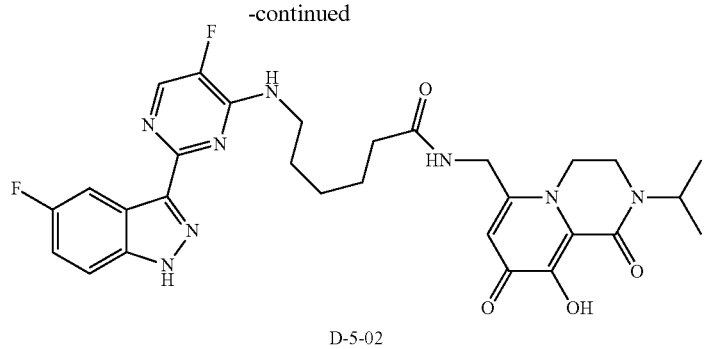

D-5-02

D-5-02 was synthesized in the similar manner as D-3-01-3. Purification by Prep-HPLC afforded D-5-02 (4.5 mg, 32%) as a brown oil.

6-(5-fluoro-2-(5-fluoro-1H-pyrazolo[3,4-b]pyridin-3-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)hexanamide

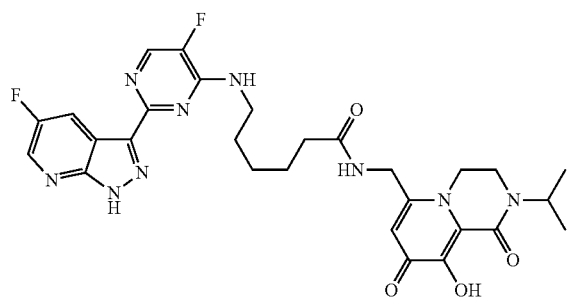 [SMILES: CC(C)N1CCn2c(CNC(=O)CCCCCNc3nc(-c4n[nH]c5ncc(F)cc45)ncc3F)cc(=O)c(O)c2C1=O]

D-5-02 was obtained as brown oil.
Yield: 12%
Mp:
MS (ESI): 596 (M+H)$^+$
1H NMR (CD$_3$OD, 400 Hz):
δ 8.63 (s, 1H), 8.39 (d, J=5.2 Hz, 1H), 8.29 (d, J=4.4 Hz, 1H), 6.65 (s, 1H), 4.80-4.85 (m, 1H), 4.47 (s, 2H), 4.35 (s, 2H), 3.82 (t, J=6.8 Hz, 2H), 3.72 (s, 2H), 2.38 (t, J=7.2 Hz, 2H), 1.87-1.90 (m, 2H), 1.77-1.81 (m, 2H), 1.56-1.59 (m, 2H), 1.27 (d, J=6.8 Hz, 6H).
D-5-03:

-continued

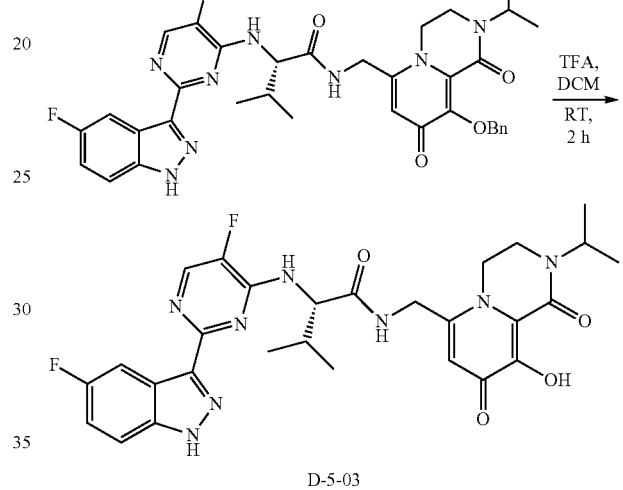

D-5-03

D-5-03 was synthesized in the similar manner as D-3-01-3. Purification by Prep-HPLC afforded D-5-03 (6.2 mg, 42%) as a pale yellow oil.

(S)-2-(5-fluoro-2-(5-fluoro-1H-pyrazolo[3,4-b]pyridin-3-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)-3-methylbutanamide

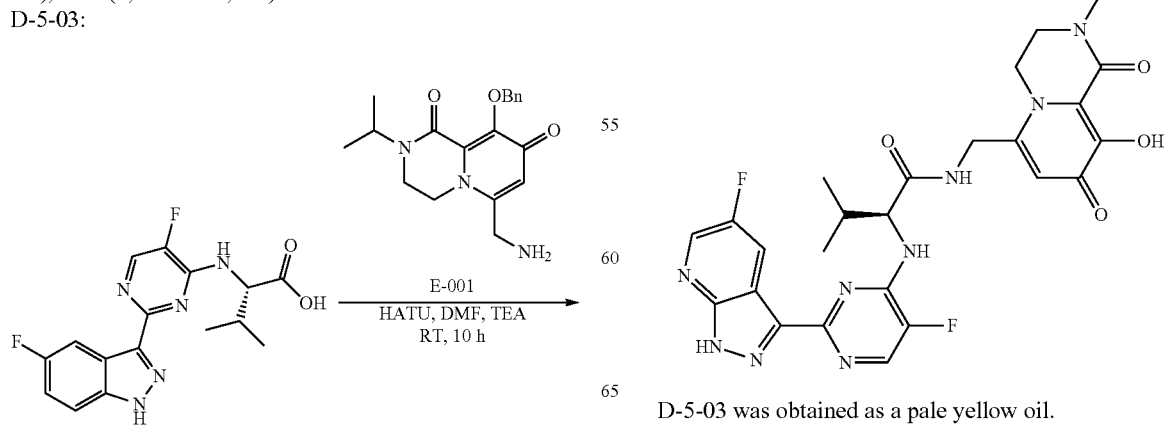

D-5-03 was obtained as a pale yellow oil.
Yield: 17%

Mp:
MS (ESI): 582 (M+H)+
1H NMR (CD3OD, 400 Hz):
δ 8.52 (s, 1H), 8.37 (d, J=2.8 Hz, 1H), 8.30 (dd, J=8.0 Hz, 2.4 Hz, 1H), 6.94 (s, 1H), 4.63-4.71 (m, 1H), 4.52-4.59 (m, 3H), 4.44 (d, J=7.2 Hz, 1H), 4.06-4.10 (m, 1H), 3.47-3.57 (m, 2H), 2.37-2.42 (m, 1H), 1.17-1.22 (m, 12H).
D-2-06:

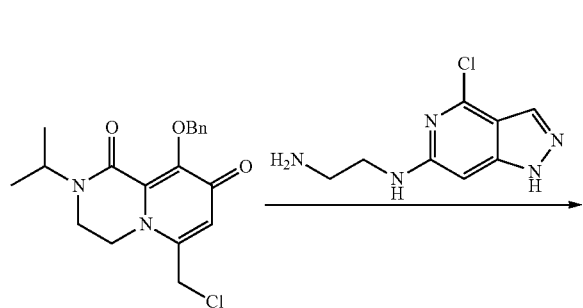

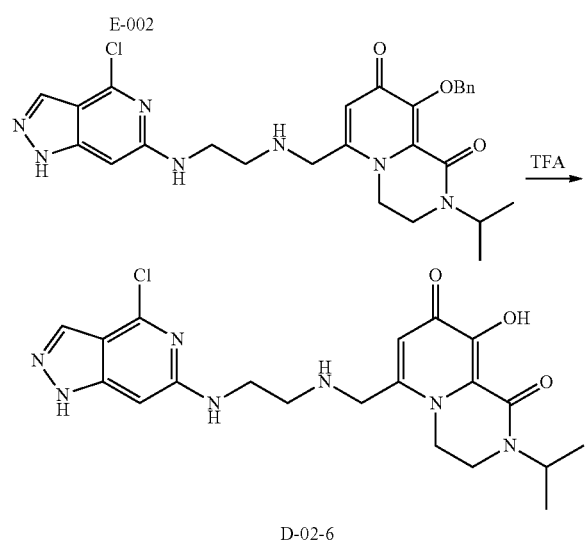

D-2-06 was synthesized in the similar manner as D-2-04. Purification by Prep-HPLC afforded D-2-06 (3.8 mg, 1.3%) as a white solid.

6-((2-(4-chloro-1H-pyrazolo[4,3-c]pyridin-6-ylamino)ethylamino)methyl)-9-hydroxy-2-isopropyl-3,4-dihydro-1H-pyrido[1,2-a]pyrazine-1,8(2H)-dione

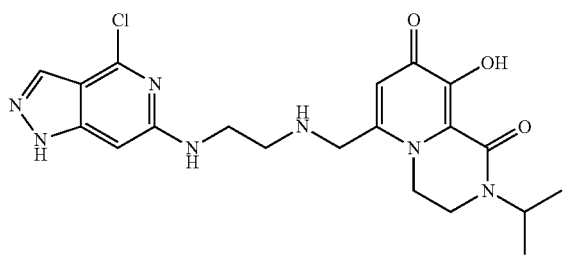 [SMILES: CC(C)N1CCn2c(CNCCNc3cc4[nH]ncc4c(Cl)n3)cc(=O)c(O)c2C1=O]

D-2-06 was obtained as a white solid
Yield: 0.7%
Mp:
MS (ESI): 446 (M+H)+

1H NMR (CD3OD, 400 Hz):
δ 8.09 (s, 1H), 6.50 (s, 1H), 6.28 (s, 1H), 4.84-4.88 (m, 1H), 4.35-4.38 (m, 2H), 3.83 (s, 2H), 3.49 (t, J=5.2 Hz, 2H), 3.42 (t, J=5.2 Hz, 2H), 2.97 (t, J=6.0 Hz, 2H), 1.20 (d, J=6.8 Hz, 6H).
D-4-01-5:

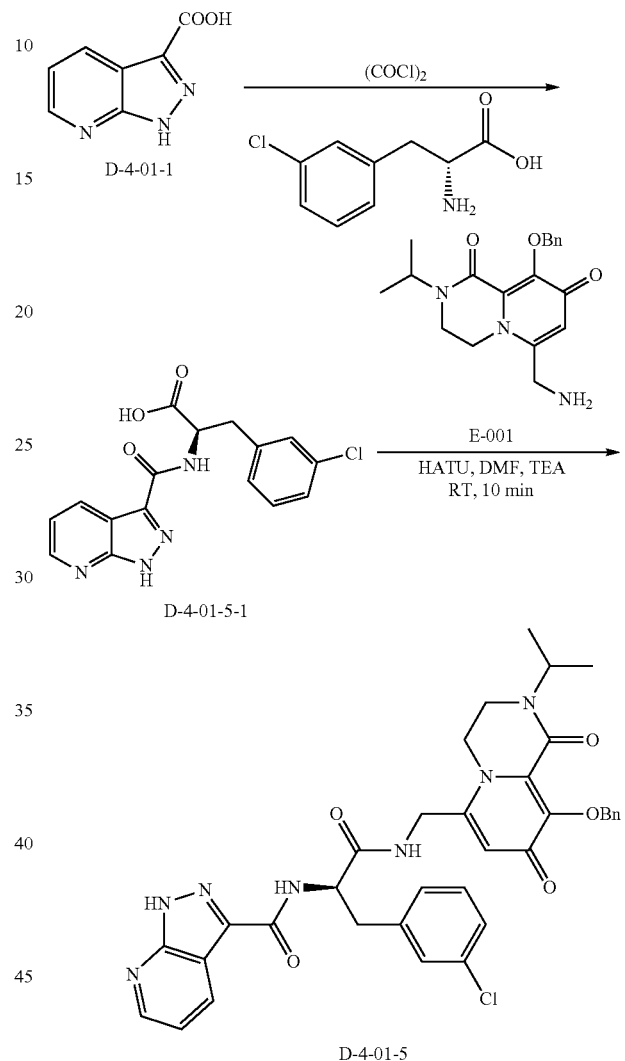

Synthesis of D-4-01-5-1:
To a mixture of D-4-01-1 (30 mg, 0.18 mmol) in DCM (3 mL) was added oxalyl dichloride (2 mL). The reaction mixture was stirred at r.t. for 3 h. The solution was concentrated and the residue was dissolved in DCM (3 mL). TEA (37 mg, 0.37 mmol) and (R)-2-amino-3-(3-chlorophenyl)propanoic acid (36 mg, 0.18 mmol) was then added and the solution was stirred at r.t. overnight. The resultant was concentrated to give D-4-01-5-1 (20 mg, 32%), which was used directly for the next step.
Synthesis of D-4-01-5:
A mixture of D-4-01-5-1 (20 mg, 0.06 mmol) and HATU (33 mg, 0.08 mmol) in DMF (3 mL) was stirred at r.t. for 0.5 h. After that, TEA (14 mg, 0.14 mmol) and E-001 (20 mg, 0.08 mmol) was added. The reaction mixture was stirred at r.t. overnight. The resultant was purified by Prep-HPLC to give D-4-01-5 (1.5 mg, 4%) as a pale white solid.

75

(R)—N-(3-(3-chlorophenyl)-1-((9-hydroxy-2-isopropyl-1,8-dioxo-2,3,4,8-tetrahydro-1H-pyrido[1,2-a]pyrazin-6-yl)methylamino)-1-oxopropan-2-yl)-1H-pyrazolo[3,4-b]pyridine-3-carboxamide

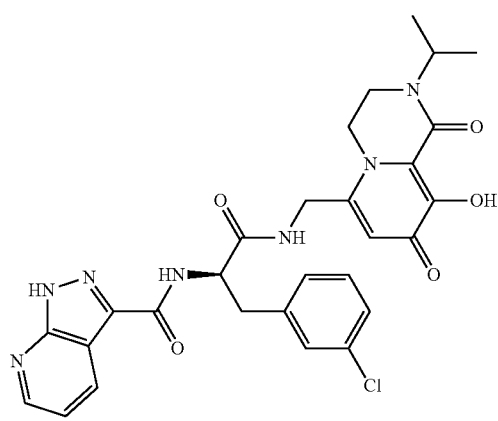 [SMILES: CC(C)N1CCn2c(CNC(=O)[C@@H](Cc3cccc(Cl)c3)NC(=O)c3n[nH]c4ncccc34)cc(=O)c(O)c2C1=O]

D-4-01-5 was obtained as a pale white solid.
Yield: 1%
Mp:
MS (ESI): 578 (M+H)+
1H NMR (d6-DMSO, 400 Hz):
δ 14.22 (br, 1H), 12.56 (br, 1H), 8.55-8.74 (m, 2H), 8.42-8.45 (m, 1H), 7.42 (s, 1H), 7.17-7.36 (m, 4H), 6.23 (s, 1H), 4.70-4.80 (m, 2H), 4.38-4.43 (m, 1H), 4.25-4.30 (m, 1H), 4.04 (s, 2H), 4.35 (s, 2H), 3.16 (d, J=6.4 Hz, 2H), 1.14 (d, J=6.4 Hz, 6H).
D-5-06:

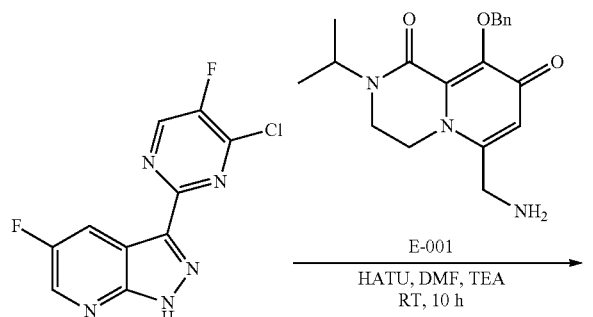

76

-continued

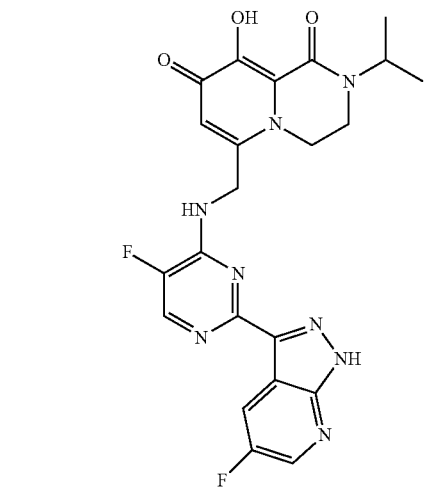

D-5-06 was synthesized in the similar manner as D-1-01. Purification by Prep-HPLC afforded D-5-06 (3.2 mg, 10%) as an orange oil.

6-((5-fluoro-2-(5-fluoro-1H-pyrazolo[3,4-b]pyridin-3-yl)pyrimidin-4-ylamino)methyl)-9-hydroxy-2-isopropyl-3,4-dihydro-1H-pyrido[1,2-a]pyrazine-1,8(2H)-dione

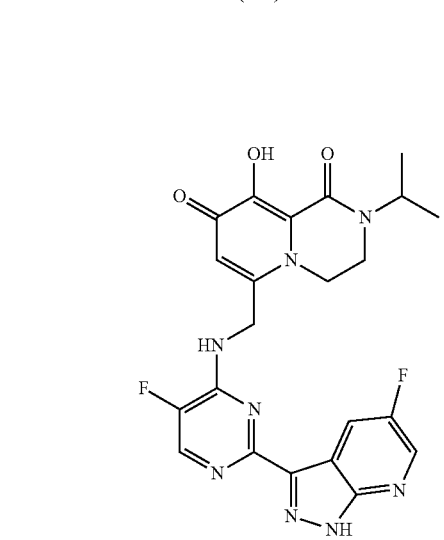

D-5-06 was obtained as an orange oil.
Yield: 7%
Mp:
MS (ESI): 483 (M+H)+
1H NMR (CD3OD, 400 Hz):
δ 8.54 (s, 1H), 8.39 (d, J=3.6 Hz, 1H), 8.29-8.31 (m, 1H), 7.04 (s, 1H), 5.08 (s, 2H), 4.93-4.98 (m, 1H), 4.71 (t, J=5.2 Hz, 2H), 3.83-3.86 (m, 2H), 1.32 (d, J=6.8 Hz, 6H).

D-6-03:

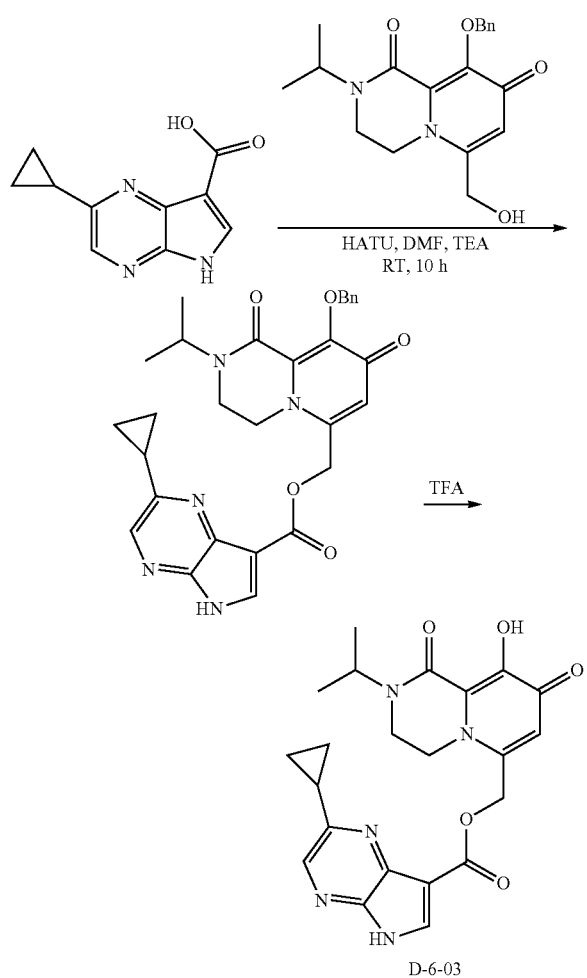

D-6-03 was synthesized in the similar manner as D-3-01-3. Purification by Prep-HPLC afforded D-6-03 (2.2 mg, 9%) as a brown oil.

2-Cyclopropyl-N-((9-hydroxy-2-isopropyl-1,8-dioxo-2,3,4,8-tetrahydro-1H-pyrido[1,2-a]pyrazin-6-yl)methyl)-5H-pyrrolo[2,3-b]pyrazine-7-carboxamide

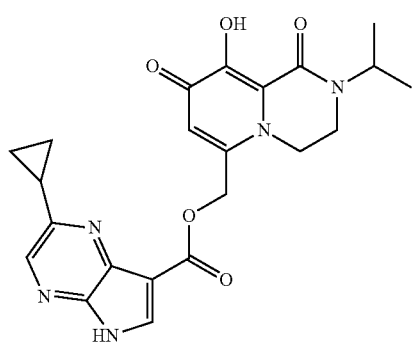 [SMILES: CC(C)N1CCn2c(COC(=O)c3c[nH]c4ncc(C5CC5)nc34)cc(=O)c(O)c2C1=O]

D-6-03 was obtained as a brown oil.
Yield: 15%
Mp:
MS (ESI): 438 (M+H)+
1H NMR (CD3OD, 400 Hz):

δ 8.41 (br, 1H), 8.25 (s, 1H), 6.78 (br, 1H), 5.44-5.51 (m, 2H), 5.06-5.10 (m, 2H), 4.50 (br, 1H), 3.75 (br, 2H), 2.29 (br, 1H), 1.28-1.35 (m, 6H), 1.04 (s, 4H).

D-6-04:

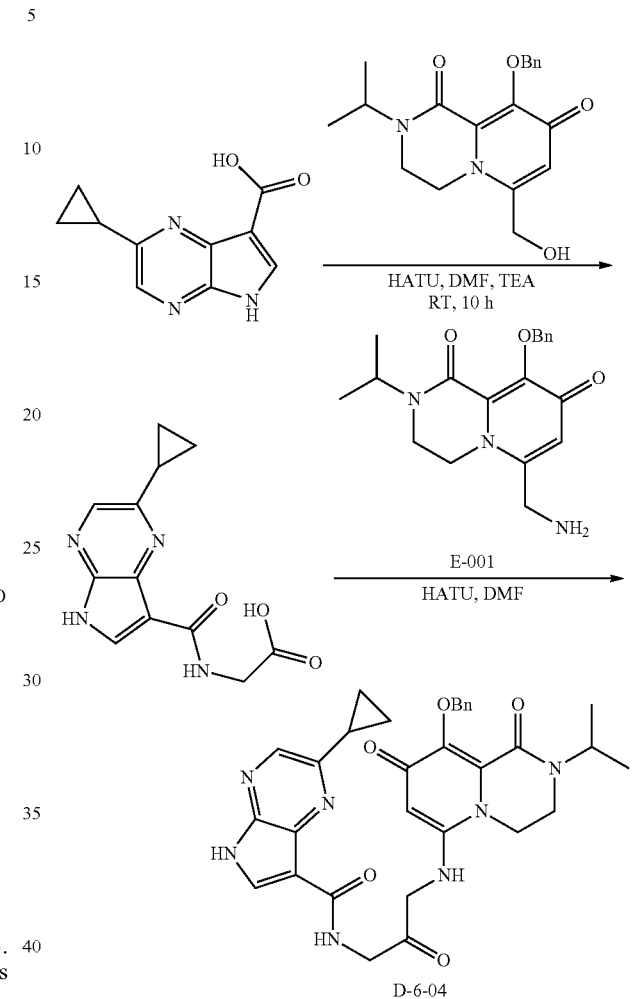

D-6-04 was synthesized in the similar manner as D-3-01-3. Purification by Prep-HPLC afforded D-6-04 (4.0 mg, 10%) as a pale white solid.

2-Cyclopropyl-N-(2-((9-hydroxy-2-isopropyl-1,8-dioxo-2,3,4,8-tetrahydro-1H-pyrido[1,2-a]pyrazin-6-yl)methylamino)-2-oxoethyl)-5H-pyrrolo[2,3-b]pyrazine-7-carboxamide

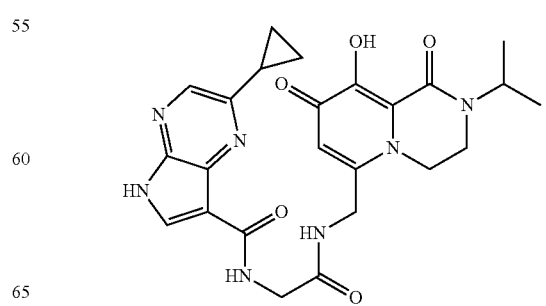

D-6-04 was obtained as a pale white solid.
Yield: 4%
Mp:
MS (ESI): 494 (M+H)+
1H NMR (d6-DMSO, 400 Hz):
δ 12.78 (br, 1H), 12.60 (s, 1H), 8.63-8.68 (m, 2H), 8.38 (s, 1H), 8.30 (d, J=2.8 Hz, 1H), 6.48 (s, 1H), 4.72-4.75 (m, 1H), 4.46 (d, J=5.2 Hz, 2H), 4.22-4.25 (m, 2H), 4.13-4.16 (m, 2H), 3.65 (s, 2H), 2.32-2.35 (m, 1H), 1.18 (d, J=6.8 Hz, 6H), 1.00-1.10 (m, 4H).
D-2-05:

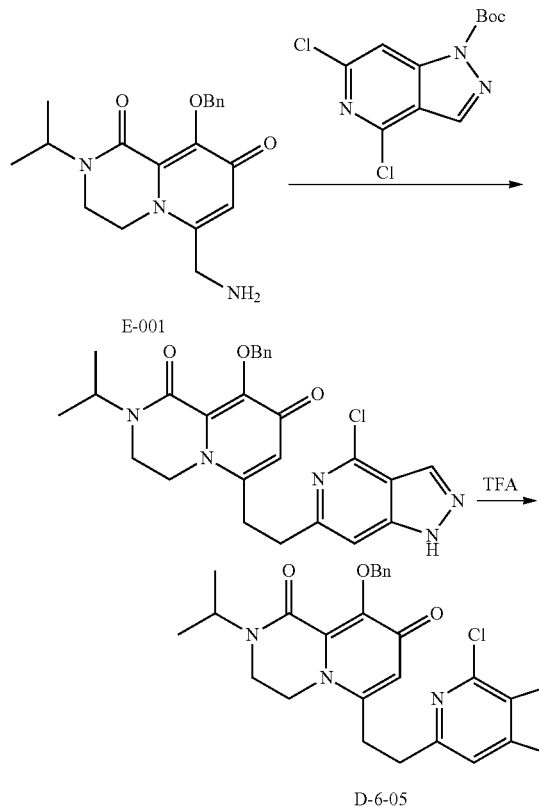

D-2-05 was synthesized in the similar manner as D-1-01. Purification by Prep-HPLC afforded D-2-05 (13 mg, 76%) as a yellow oil.

6-((4-chloro-1H-pyrazolo[4,3-c]pyridin-6-ylamino)methyl)-9-hydroxy-2-isopropyl-3,4-dihydro-1H-pyrido[1,2-a]pyrazine-1,8(2H)-dione

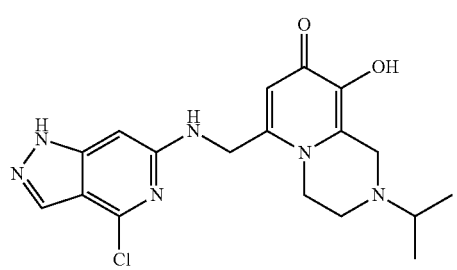 [SMILES: CC(C)N1CCn2c(CNc3cc4[nH]ncc4c(Cl)n3)cc(=O)c(O)c2C1]

D-2-05 was obtained as a yellow oil.
Yield: 55%

Mp:
MS (ESI): 403 (M+H)+
1H NMR (CD3OD, 400 Hz):
δ 8.81 (s, 1H), 7.20 (s, 1H), 6.84 (s, 1H), 4.92-5.11 (m, 3H), 4.76 (d, J=1.2 Hz, 2H), 3.86-3.89 (m, 2H), 1.32 (d, J=6.8 Hz, 6H).
D-3-01-2:

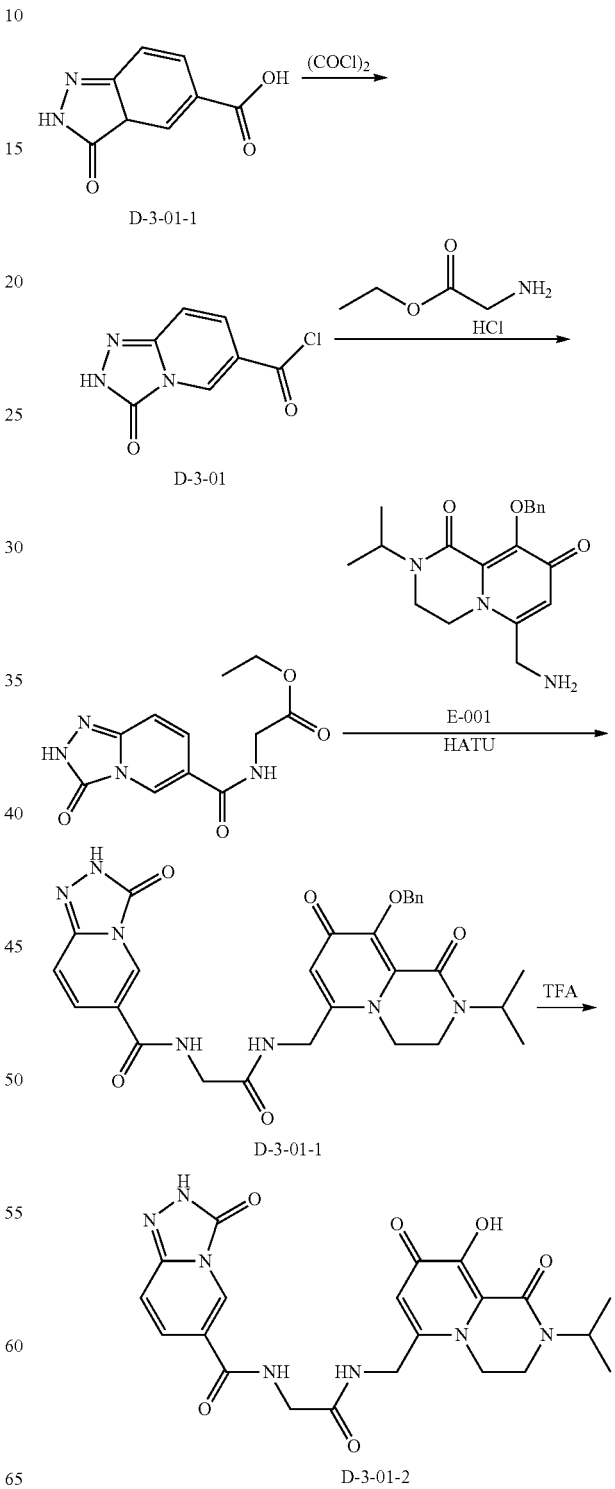

D-3-01-2 was synthesized in the similar manner as D-3-01-3. Purification by Prep-HPLC afforded D-3-01-2 (5 mg, 25%) as a pale yellow oil.

N-(2-((9-hydroxy-2-isopropyl-1,8-dioxo-2,3,4,8-tetrahydro-1H-pyrido[1,2-a]pyrazin-6-yl)methylamino)-2-oxoethyl)-3-oxo-2,3-dihydro-[1,2,4]triazolo[4,3-a]pyridine-6-carboxamide

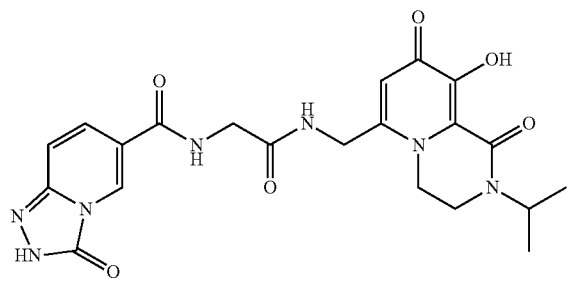 [SMILES: CC(C)N1CCn2c(CNC(=O)CNC(=O)c3ccc4n[nH]c(=O)n4c3)cc(=O)c(O)c2C1=O]

D-3-01-2 was obtained as a pale yellow oil.

Yield: 4%

Mp:

MS (ESI): 470 (M+H)$^+$

1H NMR (d$_6$-DMSO, 400 Hz):

δ 12.67 (s, 1H), 9.09 (t, J=5.2 Hz, 1H), 8.66 (d, J=5.6 Hz, 1H), 8.49-8.52 (m, 2H), 7.54 (t, J=9.2 Hz, 1H), 7.24-7.29 (m, 1H), 6.71 (s, 1H), 4.73 (t, J=6.8 Hz, 1H), 4.41-4.46 (m, 2H), 4.23-4.32 (m, 2H), 3.90-3.96 (m, 2H), 3.52-3.68 (m, 2H), 1.13-1.24 (m, 6H).

D-3-02-8:

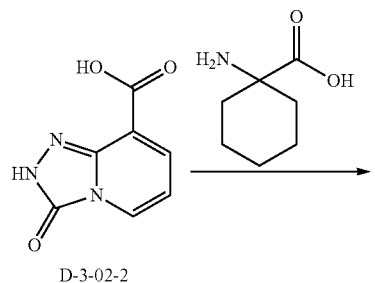

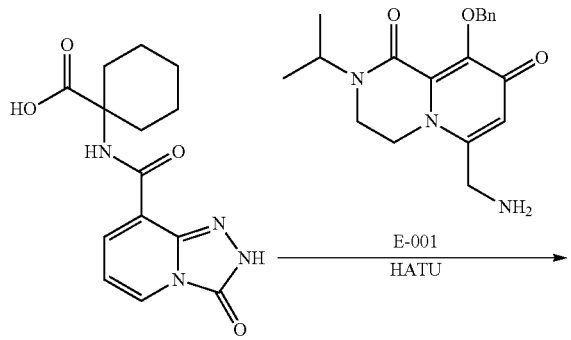

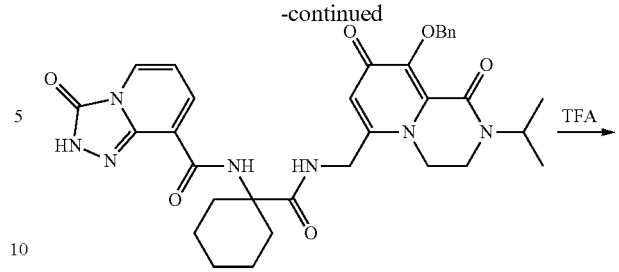

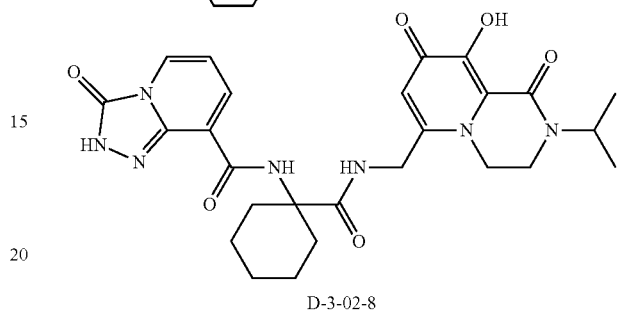

D-3-02-8 was synthesized in the similar manner as D-3-02-3. Purification by Prep-HPLC afforded D-3-02-8 (8 mg, 31%) as a pale yellow solid.

N-(1-((9-hydroxy-2-isopropyl-1,8-dioxo-2,3,4,8-tetrahydro-1H-pyrido[1,2-a]pyrazin-6-yl)methylcarbamoyl)cyclohexyl)-3-oxo-2,3-dihydro-[1,2,4]triazolo[4,3-a]pyridine-8-carboxamide

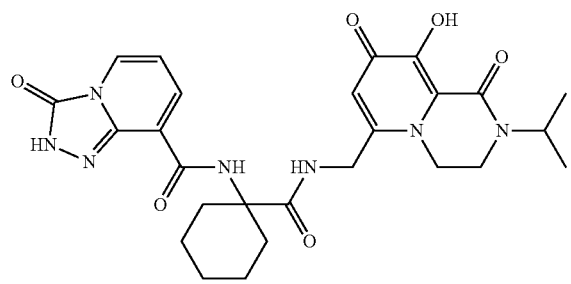 [SMILES: CC(C)N1CCn2c(CNC(=O)C3(NC(=O)c4cccn5c(=O)[nH]nc45)CCCCC3)cc(=O)c(O)c2C1=O]

D-3-02-8 was obtained as a pale yellow solid.

Yield: 4%

Mp:

MS (ESI): 538 (M+H)$^+$

1H NMR (d$_6$-DMSO, 400 Hz):

δ 12.41 (s, 1H), 8.33 (s, 1H), 8.09-8.14 (m, 1H), 7.94 (d, J=6.8 Hz, 1H), 6.78 (t, J=6.8 Hz, 1H), 4.72 (t, J=6.8 Hz, 1H), 4.21-4.35 (m, 2H), 4.06 (s, 1H), 3.51-3.54 (m, 1H), 3.07 (d, J=6.0 Hz, 4H), 2.06-2.14 (m, 2H), 1.73-1.79 (m, 2H), 1.57-1.63 (m, 2H), 1.45-1.47 (m, 2H), 1.16 (t, J=7.2 Hz, 6H).

D-3-02-9:

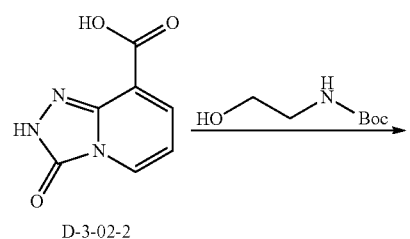

-continued

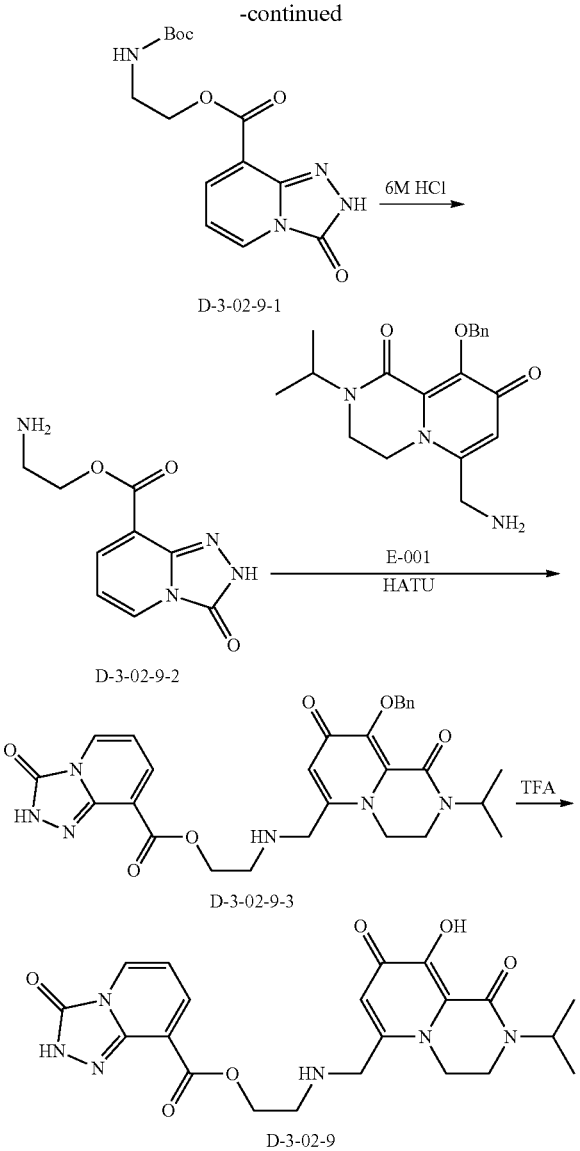

Synthesis of D-3-02-9-1:
A mixture of D-3-02-2 (60 mg, 0.33 mmol) and HATU (165 mg, 0.42 mmol) in DCM (5 mL) was stirred at r.t. for 0.5 h. After that, DIEA (84 mg, 0.66 mmol) and tert-butyl 2-hydroxyethylcarbamate (204 mg, 0.33 mmol) was added. The reaction mixture was stirred at r.t. overnight. The resultant was purified by Prep-TLC (MeOH/DCM=1/5) to give D-3-02-9-1 (60 mg, 55%) as a yellow solid.

Synthesis of D-3-02-9-2:
To a mixture of D-3-02-9-1 (60 mg, 0.18 mmol) in MeOH (3 mL) was added 6N HCl (6 mL). The mixture was stirred at r.t. for 0.5 h and then concentrated. The residue was purified by Prep-TLC (MeOH/DCM=1/2) to give D-3-02-9-2 (30 mg, 73%) as a yellow oil.

Synthesis of D-3-02-9-3:
A mixture of D-3-02-9-2 (30 mg, 0.13 mmol), $K_2CO_3$ (37 mg, 0.27 mmol) and E-002 (48 mg, 0.13 mmol) in DMF (3 mL) was stirred at r.t. for 3 h. The mixture was filtered and concentrated under the reduced pressure. The residue was purified by Prep-TLC (MeOH/DCM=1/5) to give D-3-02-9-3 (20 mg, 27%) as a yellow oil.

Synthesis of D-3-02-9:
In the same manner as D-1-01, purification by Prep-HPLC afforded D-3-02-9 (9 mg, 53%) as a brown solid.

2-((9-hydroxy-2-isopropyl-1,8-dioxo-2,3,4,8-tetrahydro-1H-pyrido[1,2-a]pyrazin-6-yl)methylamino)ethyl-3-oxo-2,3-dihydro-[1,2,4]triazolo[4,3-a]pyridine-8-carboxylate D-3-02-9 was obtained as a brown solid.
Yield: 6%
Mp:
MS (ESI): 457 (M+H)$^+$
1H NMR (CD$_3$OD, 400 Hz):
δ 7.97 (d, J=12.0 Hz, 2H), 6.90 (s, 1H), 6.76 (s, 1H), 5.37 (s, 2H), 4.75-4.80 (m, 1H), 4.50-4.55 (m, 2H), 3.70 (br, 2H), 3.61 (br, 2H), 3.57 (br, 2H), 1.17 (d, J=6.4 Hz, 6H).

D-4-01:

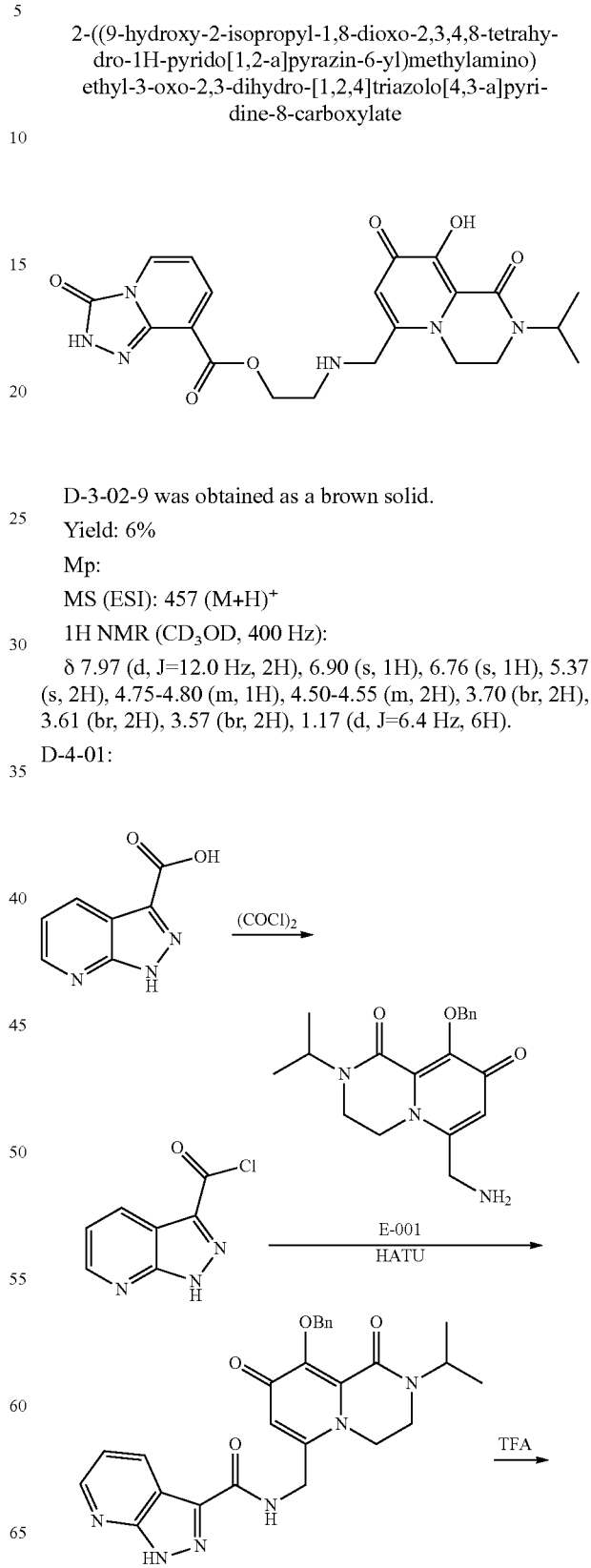

85
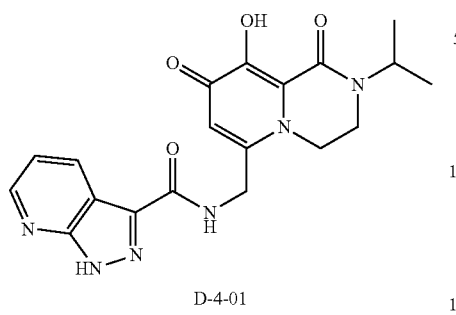
D-4-01
D-4-01 was synthesized in the similar manner as D-3-01-3. Purification by Prep-HPLC afforded D-4-01 (3 mg, 18%) as a brown solid.
86
N-((9-hydroxy-2-isopropyl-1,8-dioxo-2,3,4,8-tetrahydro-1H-pyrido[1,2-a]pyrazin-6-yl)methyl)-1H-pyrazolo[3,4-b]pyridine-3-carboxamide
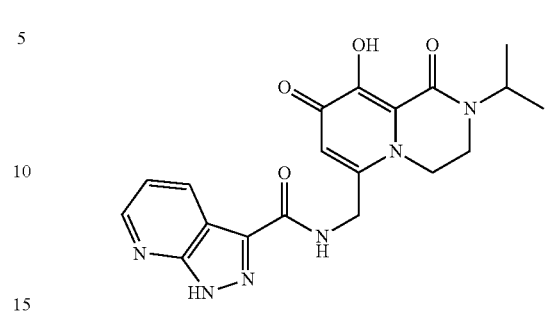
D-4-01 was obtained as a brown solid.
Yield: 6%
Mp:
MS (ESI): 397 (M+H)$^+$
1H NMR (CD$_3$OD, 400 Hz):
δ 8.60-8.63 (m, 2H), 7.38 (d, J=3.2 Hz, 1H), 7.19 (s, 1H), 4.85-4.90 (m, 3H), 4.66 (s, 2H), 3.85 (s, 2H), 1.26-1.31 (m, 6H).
D-4-01-3:
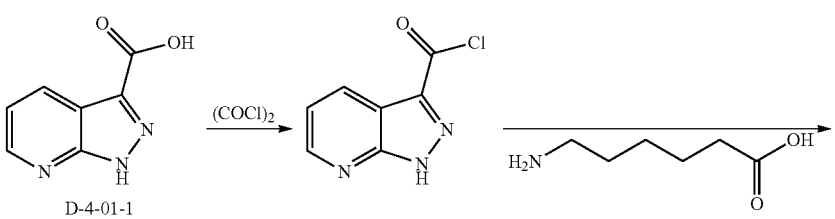
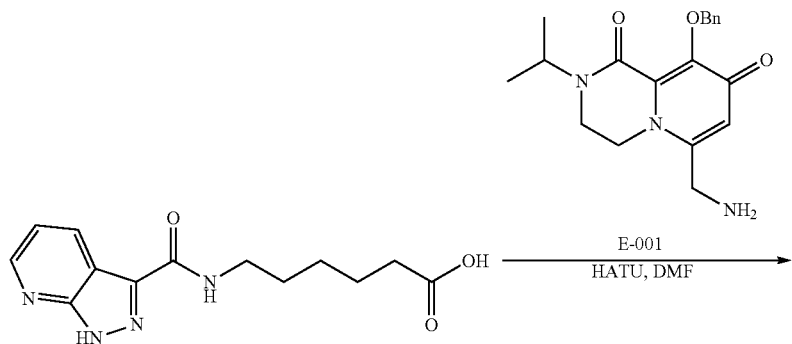
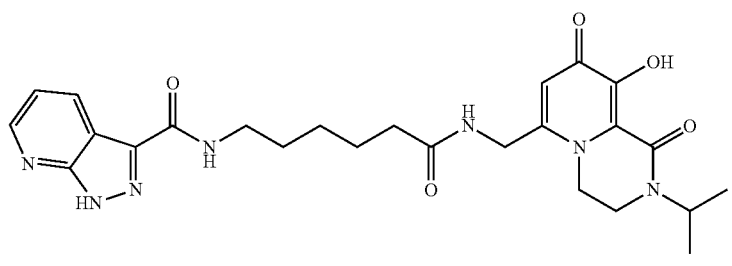
D-4-01-3

D-4-01-3 was synthesized in the similar manner as D-3-01-3. Purification by Prep-HPLC afforded D-4-01-3 (10 mg, 27%) as a brown solid.

N-(6-((9-hydroxy-2-isopropyl-1,8-dioxo-2,3,4,8-tetrahydro-1H-pyrido[1,2-a]pyrazin-6-yl)methylamino)-6-oxohexyl)-1H-pyrazolo[3,4-b]pyridine-3-carboxamide

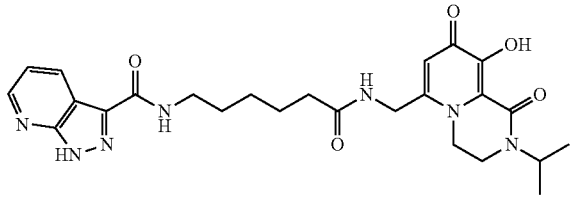 [SMILES: CC(C)N1CCn2c(CNC(=O)CCCCCNC(=O)c3n[nH]c4ncccc34)cc(=O)c(O)c2C1=O]

D-4-01-3 was obtained as a brown solid.
Yield: 10%
Mp:
MS (ESI): 510 (M+H)+
1H NMR (CD₃OD, 400 Hz):
δ 8.56-8.63 (m, 2H), 7.31-7.34 (m, 1H), 6.57 (s, 1H), 5.03-5.09 (m, 1H), 4.46 (s, 2H), 4.31 (s, 2H), 3.69 (d, J=15.6 Hz, 2H), 3.40-3.46 (m, 2H), 2.30-2.34 (m, 2H), 1.66-1.72 (m, 4H), 1.39-1.46 (m, 2H), 1.21-1.31 (m, 6H).
D-4-01-4:

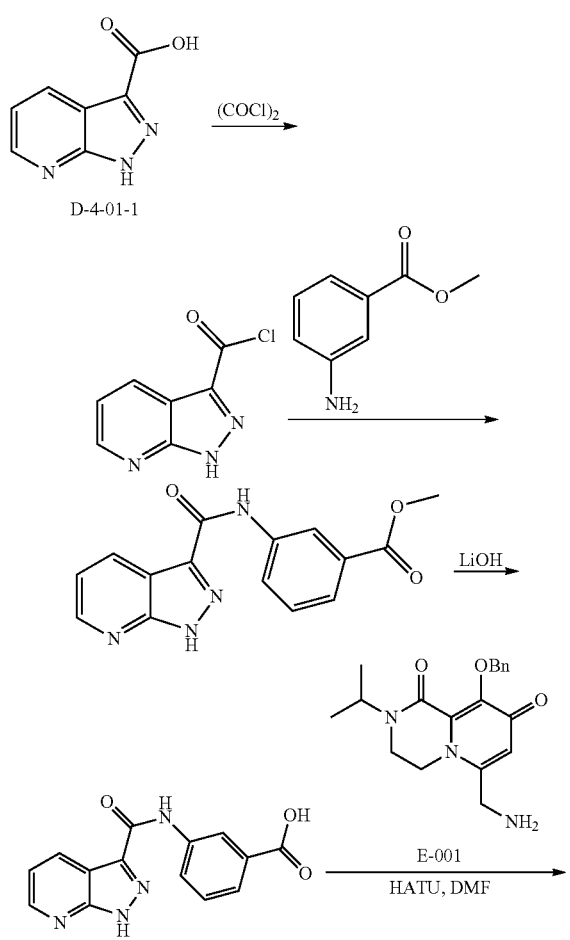

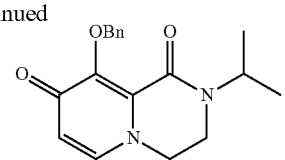

D-4-01-4

D-4-01-4 was synthesized in the similar manner as D-3-01-3. Purification by Prep-HPLC afforded D-4-01-4 (6 mg, 33%) as pale white solid.

N-(3-((9-hydroxy-2-isopropyl-1,8-dioxo-2,3,4,8-tetrahydro-1H-pyrido[1,2-a]pyrazin-6-yl)methylcarbamoyl)phenyl)-1H-pyrazolo[3,4-b]pyridine-3-carboxamide

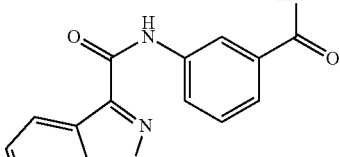

D-4-01-4 was obtained as a pale white solid.
Yield: 6%
Mp:
MS (ESI): 516 (M+H)+
1H NMR (CD₃OD, 400 Hz):
δ 8.70 (d, J=6.0 Hz, 2H), 8.43 (s, 1H), 7.93-8.00 (m, 1H), 7.70 (s, 1H), 7.55 (s, 1H), 7.34-7.40 (m, 2H), 4.90-5.12 (m, 3H), 4.74 (s, 2H), 3.90 (s, 2H), 1.32 (d, J=6.0 Hz, 6H).
D-5-04:

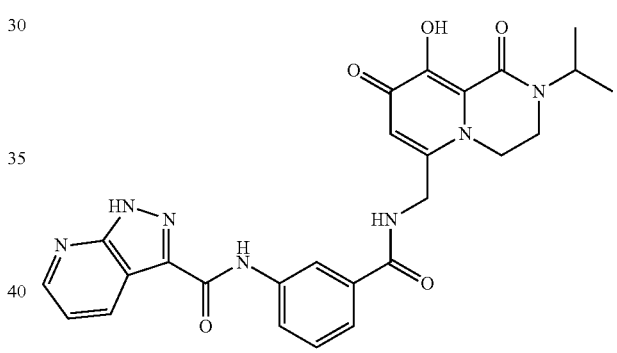

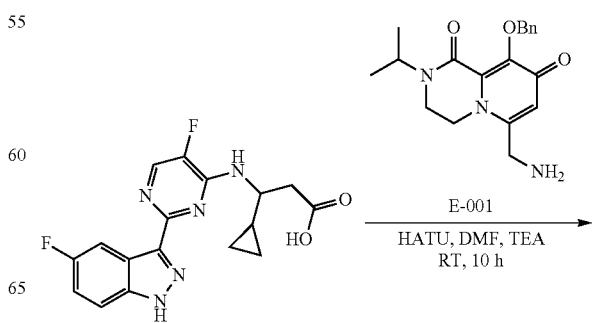

89
-continued

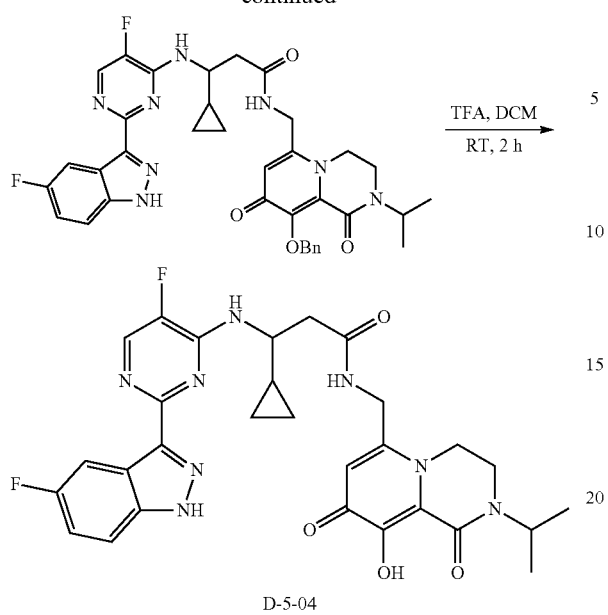

D-5-04

D-5-04 was synthesized in the similar manner as D-3-01-3. Purification by Prep-HPLC afforded D-5-04 (5 mg, 71%) as a brown oil.

90

3-cyclopropyl-3-(5-fluoro-2-(5-fluoro-1H-pyrazolo[3,4-b]pyridin-3-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)propanamide

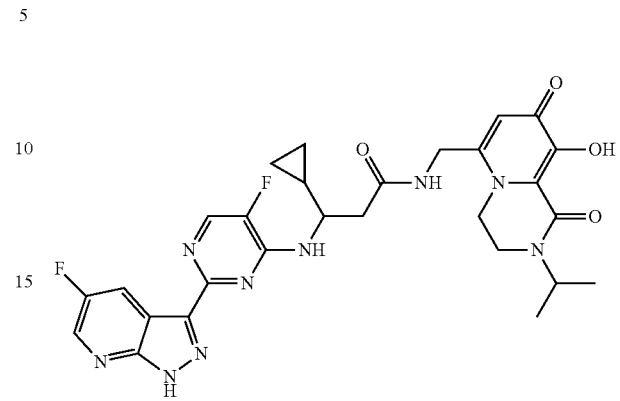

D-5-04 was obtained as a brown oil.
Yield: 29%
Mp:
MS (ESI): 594 (M+H)$^+$
1H NMR (CD$_3$OD, 400 Hz):
δ 8.56-8.59 (m, 2H), 8.26 (d, J=4.4 Hz, 1H), 6.64 (s, 1H), 4.77 (s, 1H), 4.50 (d, J=4.0 Hz, 1H), 4.36-4.46 (m, 4H), 3.54-3.63 (m, 2H), 2.88 (d, J=4.8 Hz, 2H), 1.28 (d, J=6.8 Hz, 1H), 1.19-1.24 (m, 6H), 0.43-0.79 (m, 4H).
D-5-05:

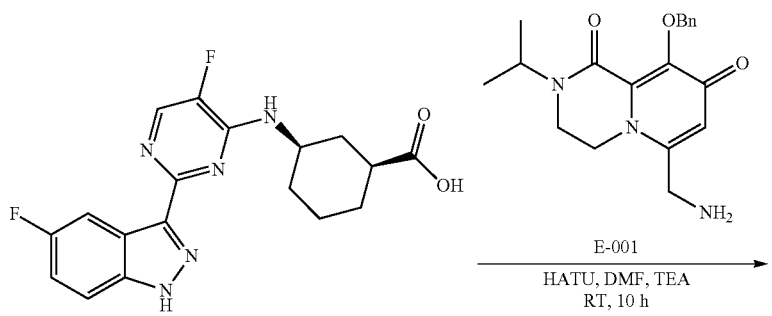

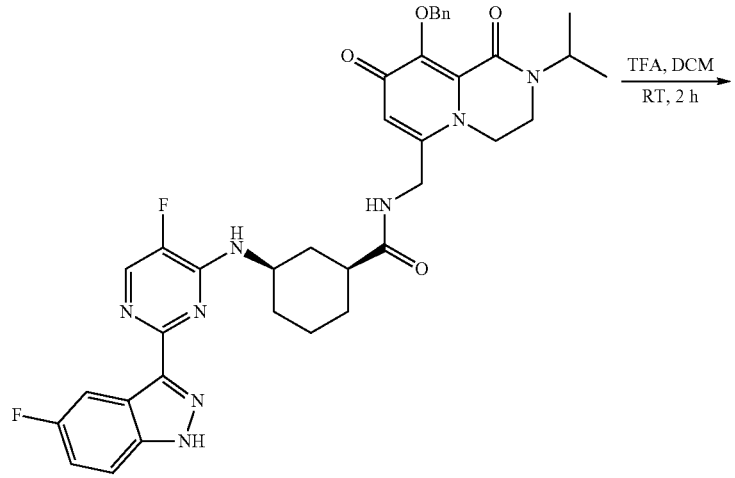

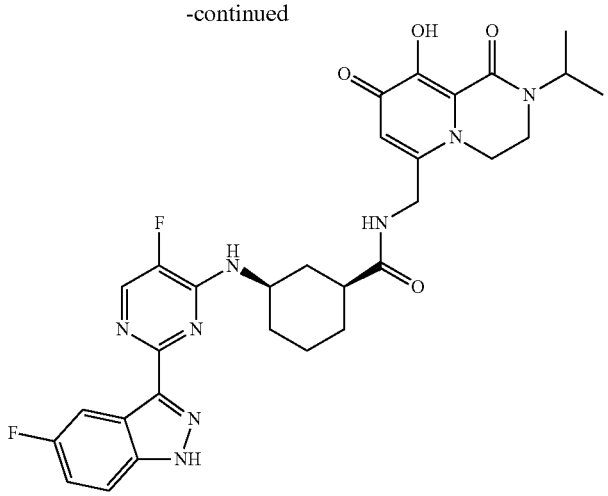

D-5-05

D-5-05 was synthesized in the similar manner as D-3-01-3. Purification by Prep-HPLC afforded D-5-05 (5 mg, 19%) as a brown oil.

cis-3-(5-fluoro-2-(5-fluoro-1H-pyrazolo[3,4-b]pyridin-3-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)cyclohexanecarboxamide

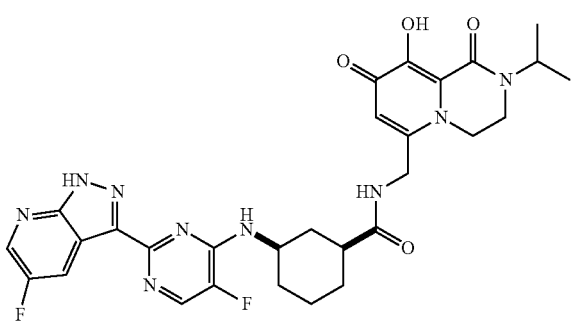

D-5-05 was obtained as a brown oil.
Yield: 15%
Mp:
MS (ESI): 608 (M+H)$^+$
1H NMR (CD$_3$OD, 400 Hz):
δ 8.63 (s, 1H), 8.39 (d, J=6.8 Hz, 1H), 8.32 (d, J=4.4 Hz, 1H), 6.77 (s, 1H), 5.01 (d, J=9.6 Hz, 2H), 4.54 (d, J=3.2 Hz, 2H), 4.41-4.47 (m, 2H), 3.73 (s, 2H), 2.83 (s, 1H), 2.23-2.31 (m, 2H), 1.81 (s, 1H), 1.68 (s, 1H), 1.55-1.58 (m, 2H), 1.28-1.32 (m, 2H), 1.20-1.26 (m, 6H).
D-6-01:

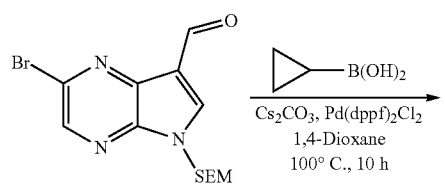

-continued

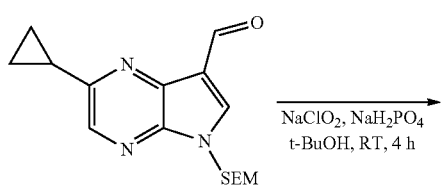

D-6-02

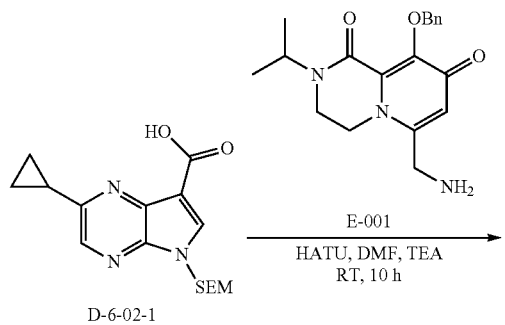

D-6-02-1

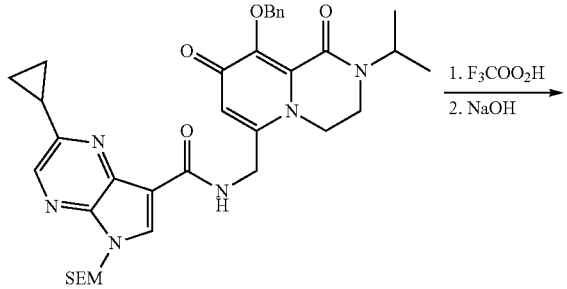

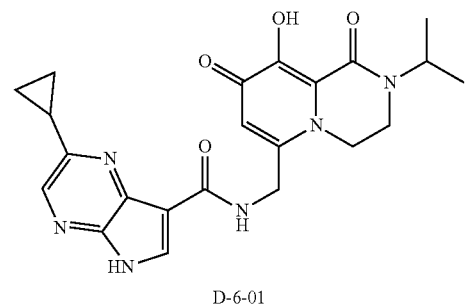

D-6-01

Synthesis of D-6-02:

A mixture of C-003 (3.60 g, 10.1 mmol), cyclopropylboronic acid (1.30 g, 15.2 mmol), Cs$_2$CO$_3$ (6.60 g, 20.3 mmol) and Pd(dppf)Cl$_2$ (0.37 g, 0.51 mmol) in dioxane (100 mL) was refluxed for 5 h under N$_2$ atmosphere. The solvent was removed by the reduced pressure and the residue was purified by column chromatography on silica gel (ethyl acetate/petroleum ether=1/50~1/10) to give D-6-02 (2.61 g, 81%) as a pale yellow solid.

Synthesis of D-6-02-1:

To a mixture of D-6-02 (3.00 g, 9.5 mmol) and sodium dihydrogen phosphate (3.90 g, 33.1 mmol) in tert-butanol/water (50 mL/4 mL) was added 2-methyl-2-butene (3.31 g, 47.0 mmol). A mixture of sodium chlorite (2.62 g, 28.4 mmol) in water (4 mL) was subsequently added dropwise. The mixture was stirred at r.t. for 5 h. The solvent was removed under the reduced pressure and the resultant was adjusted to pH=6.0 with 2M HCl. the mixture was extracted with ethyl acetate (2×30 mL). The organic phase was dried and concentrated to afford D-6-02-1 (2.61 g, 83%) as a pale yellow solid. In the following steps, D-6-01 was synthesized in the similar manner as D-6-05. Purification by Prep-HPLC afforded D-6-01 (5.2 mg, 24%) as a brown oil.

2-cyclopropyl-N-((9-hydroxy-2-isopropyl-1,8-dioxo-2,3,4,8-tetrahydro-1H-pyrido[1,2-a]pyrazin-6-yl)methyl)-5H-pyrrolo[3,2-b]pyrazine-7-carboxamide (D-6-01)

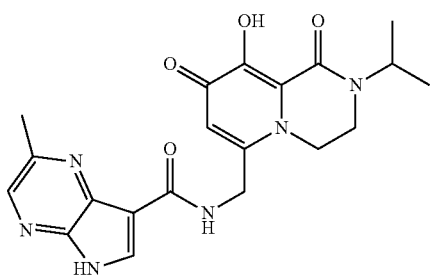 [SMILES: Cc1cnc2[nH]cc(C(=O)NCc3cc(=O)c(O)c4n3CCN(C(C)C)C4=O)c2n1]

D-6-01 was obtained as a brown oil.

Yield: 1%

Mp:

MS (ESI): 437 (M+H)$^+$ $^1$H NMR (CD$_3$OD, 400 Hz):

δ 8.35 (s, 1H), 8.30 (s, 1H), 7.17 (s, 1H), 4.95-5.00 (m, 3H), 4.67 (br, 2H), 3.86 (br, 2H), 2.34 (br, 1H), 1.31 (d, J=6.4 Hz, 6H), 1.10-1.14 (m, 4H).

$^{13}$C NMR (d$_6$-DMSO, 300 Hz):

D-6-05:

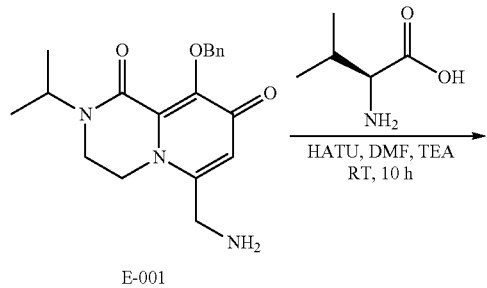

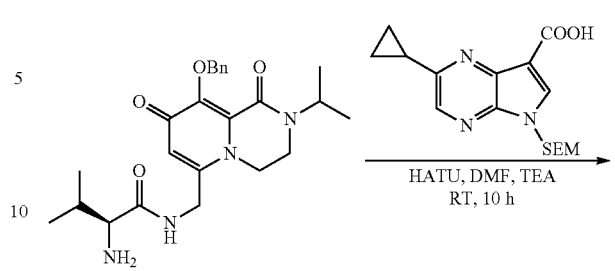

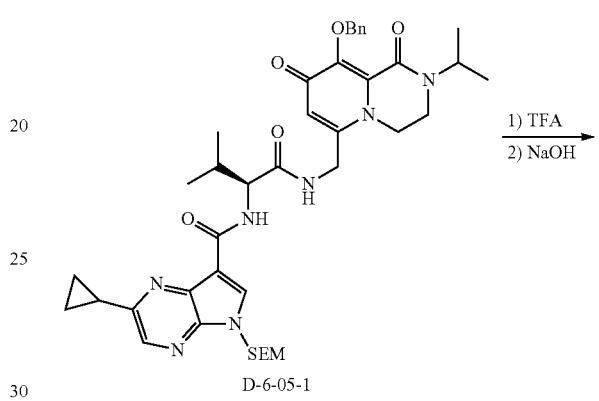

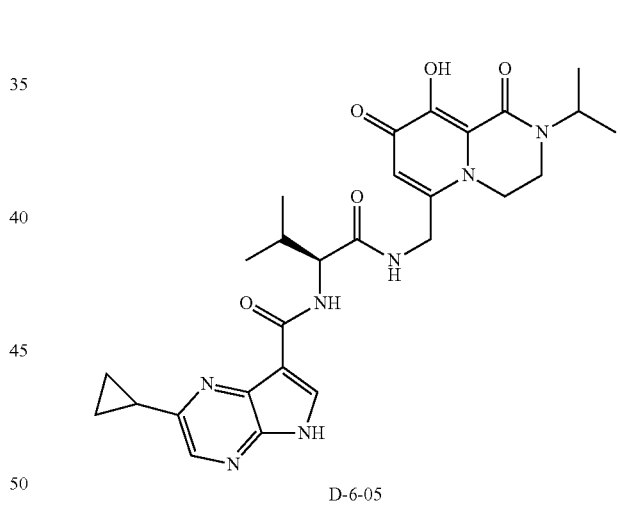

D-6-05-1 was synthesized in the similar manner as D-3-02-3-2. To a solution of D-6-05-1 (20 mg, 0.03 mmol) in DCM (3 mL) was added TFA (2 mL). The solution was stirred at r.t. for 2 h and then concentrated. The residue was redissolved in DCM (5 mL) and 4N NaOH (5 mL) was added. The solution was stirred at r.t. overnight. The pH of the solution was adjusted to 7 with 2N HCl. The resultant was concentrated and the solid was washed by MeOH/DCM=1/10 (8 mL×3). The organic phase was concentrated and the residue was purified by Prep-HPLC to afford the product D-6-05 (6 mg, 43%) as a pale white solid.

95

(S)-2-cyclopropyl-N-(1-((9-hydroxy-2-isopropyl-1,8-dioxo-2,3,4,8-tetrahydro-1H-pyrido[1,2-a]pyrazin-6-yl)methylamino)-3-methyl-1-oxobutan-2-yl)-5H-pyrrolo[3,2-b]pyrazine-7-carboxamide

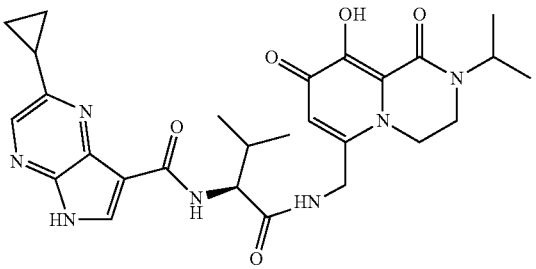 [SMILES: CC(C)[C@H](NC(=O)c1c[nH]c2ncc(C3CC3)nc12)C(=O)NCc1cc(=O)c(O)c2n1CCN(C(C)C)C2=O]

D-6-05 was obtained as a pale white solid.

Yield: 19%

Mp:

MS (ESI): 536 (M+H)$^+$

1H NMR (CD$_3$OD, 400 Hz):

δ 9.01 (d, J=6.8 Hz, 1H), 8.38 (s, 1H), 8.23 (s, 1H), 7.07 (s, 1H), 4.90 (s, 1H), 4.68 (d, J=5.2 Hz, 1H), 4.56-4.60 (m, 1H), 4.50 (s, 3H), 3.74-3.77 (m, 2H), 2.33-2.35 (m, 2H), 1.26-1.29 (m, 4H), 1.11-1.17 (m, 12H).

D-6-06:

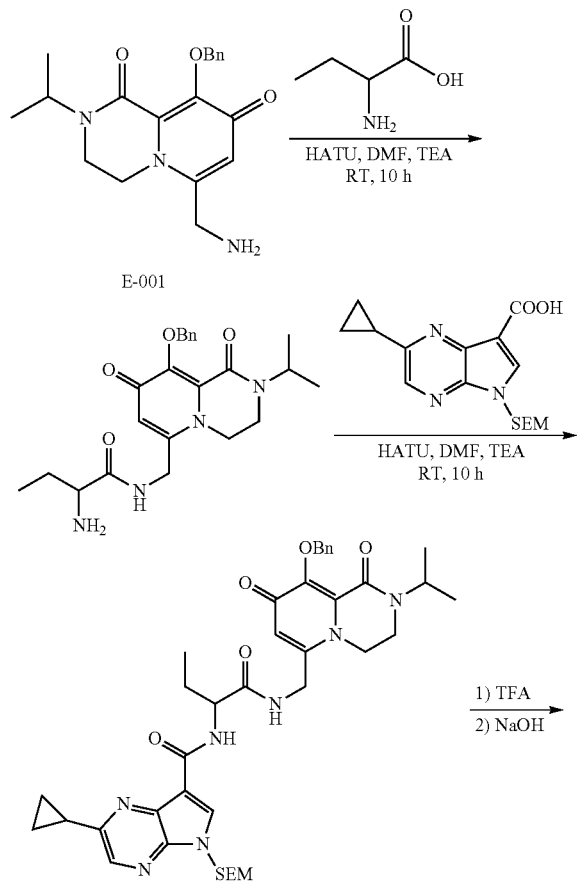

96

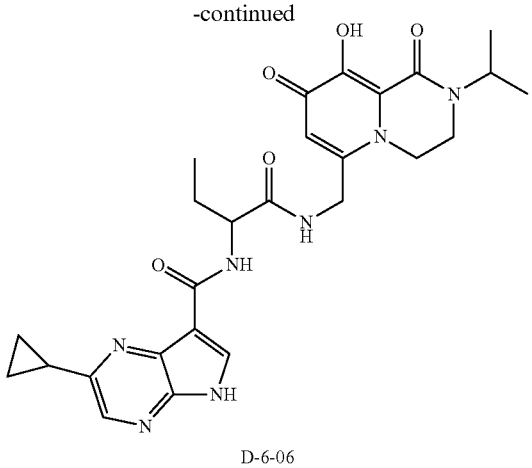

D-6-06

D-6-06 was synthesized in the similar manner as D-6-05. Purification by Prep-HPLC afforded D-6-06 (5 mg, 36%) as a white solid.

2-Cyclopropyl-N-(1-((9-hydroxy-2-isopropyl-1,8-dioxo-2,3,4,8-tetrahydro-1H-pyrido[1,2-a]pyrazin-6-yl)methylamino)-1-oxobutan-2-yl)-5H-pyrrolo[3,2-b]pyrazine-7-carboxamide D-6-06 was obtained as a white solid.

Yield: 16%

Mp:

MS (ESI): 522 (M+H)$^+$

1H NMR (d$_6$-DMSO, 400 Hz):

δ 12.62 (s, 1H), 8.82 (d, J=5.6 Hz, 1H), 8.73 (d, J=7.6 Hz, 1H), 8.41 (s, 1H), 8.29 (d, J=2.8 Hz, 1H), 6.59 (s, 1H), 4.70-4.74 (m, 1H), 4.60-4.64 (m, 1H), 4.45-4.49 (m, 2H), 4.25-4.33 (m, 2H), 3.66 (s, 2H), 2.34 (d, J=8.0 Hz, 1H), 1.77-1.87 (m, 2H), 1.17 (d, J=4.8 Hz, 6H), 1.06 (t, J=3.2 Hz, 4H), 0.93-1.02 (m, 3H).

D-6-07:

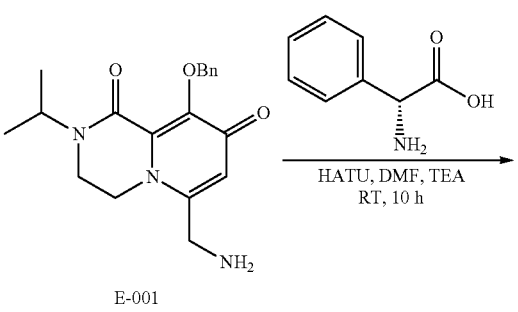

-continued

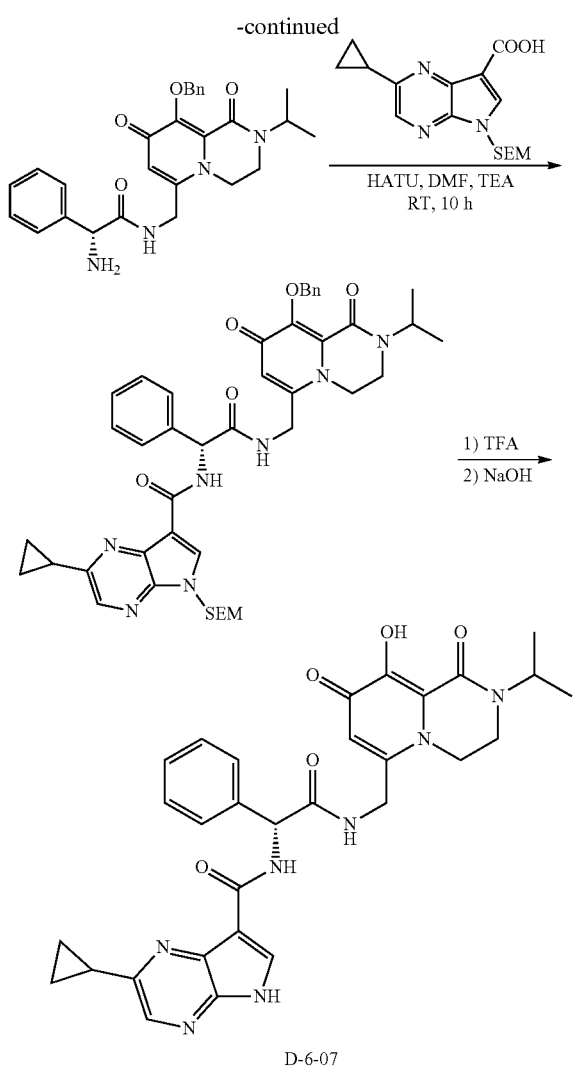

D-6-07

D-6-07 was synthesized in the similar manner as D-6-05. Purification by Prep-HPLC afforded D-6-07 (3 mg, 21%) as a white solid.

(R)-2-cyclopropyl-N-(2-((9-hydroxy-2-isopropyl-1,8-dioxo-2,3,4,8-tetrahydro-1H-pyrido[1,2-a]pyrazin-6-yl)methylamino)-2-oxo-1-phenylethyl)-5H-pyrrolo[3,2-b]pyrazine-7-carboxamide

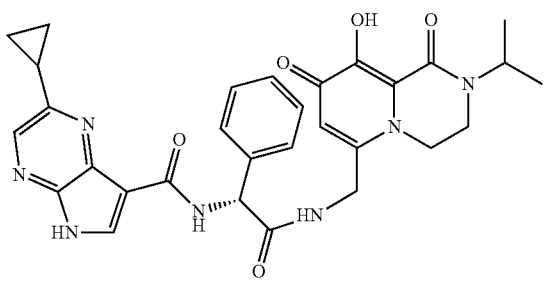 [SMILES: CC(C)N1CCn2c(CNC(=O)[C@H](NC(=O)c3c[nH]c4ncc(C5CC5)nc34)c3ccccc3)cc(=O)c(O)c2C1=O]

D-6-07 was obtained as a white solid.
Yield: 9%
Mp:
MS (ESI): 570 (M+H)$^+$
1H NMR (d$_6$-DMSO, 400 Hz):
δ 12.62 (s, 1H), 9.34 (d, J=8.0 Hz, 1H), 9.05 (s, 1H), 8.43 (s, 1H), 8.30 (d, J=1.4 Hz, 1H), 7.52 (d, J=7.2 Hz, 2H), 7.41 (t, J=7.2 Hz, 2H), 7.35 (d, J=7.2 Hz, 1H), 6.36 (s, 1H), 5.73 (d, J=7.6 Hz, 1H), 4.68 (d, J=6.8 Hz, 1H), 4.40-4.44 (m, 1H), 4.07-4.09 (m, 2H), 3.47-3.49 (m, 2H), 3.34-3.38 (m, 2H), 2.33 (d, J=3.6 Hz, 1H), 1.22-1.23 (m, 6H), 1.13-1.15 (m, 4H).
D-6-08:

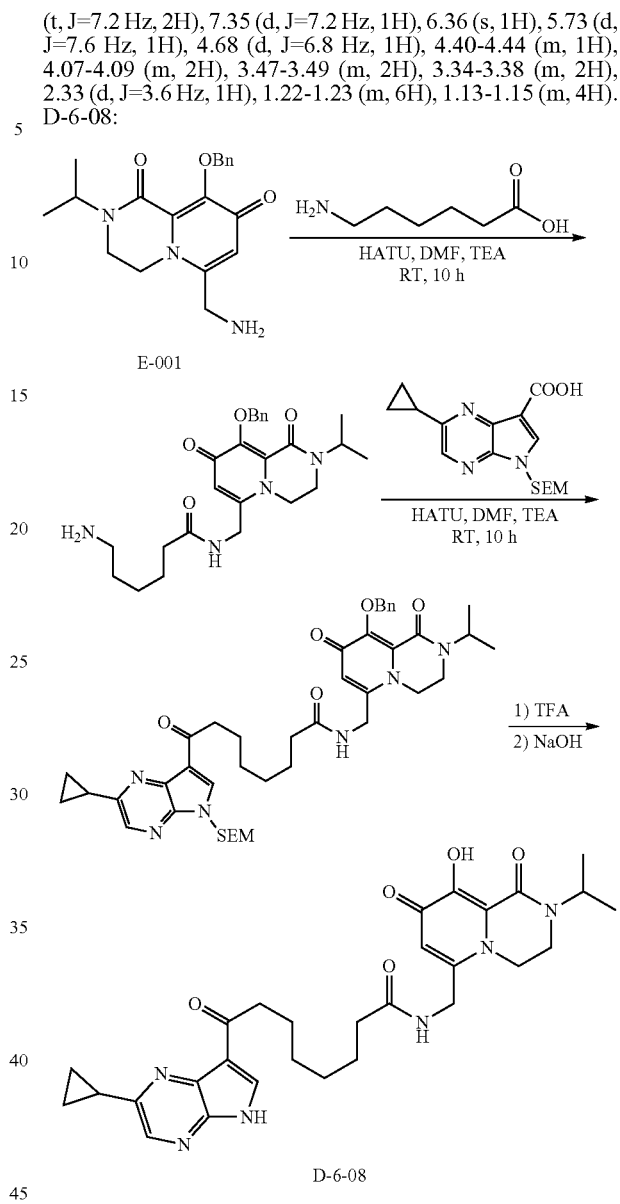

D-6-08

D-6-08 was synthesized in the similar manner as D-6-05. Purification by Prep-HPLC afforded D-6-08 (10 mg, 71%) as a pale white solid.

2-Cyclopropyl-N-(6-((9-hydroxy-2-isopropyl-1,8-dioxo-2,3,4,8-tetrahydro-1H-pyrido[1,2-a]pyrazin-6-yl)methylamino)-6-oxohexyl)-5H-pyrrolo[3,2-b]pyrazine-7-carboxamide

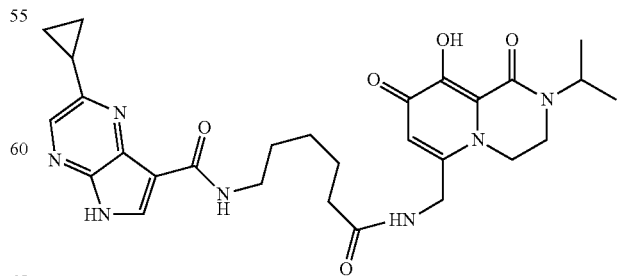

D-6-08 was obtained as a pale white solid.
Yield: 31%

Mp:

MS (ESI): 550 (M+H)⁺

1H NMR (CD₃OD, 400 Hz):

δ 8.34 (s, 1H), 8.21 (s, 1H), 7.11 (s, 1H), 4.57-4.64 (m, 4H), 4.11 (d, J=7.2 Hz, 1H), 3.81 (s, 2H), 3.53 (s, 2H), 2.33-2.39 (m, 2H), 2.04 (d, J=9.2 Hz, 1H), 1.72-1.77 (m, 4H), 1.54 (s, 2H), 1.24-1.31 (m, 6H), 1.09-1.15 (m, 4H).

D-6-09:

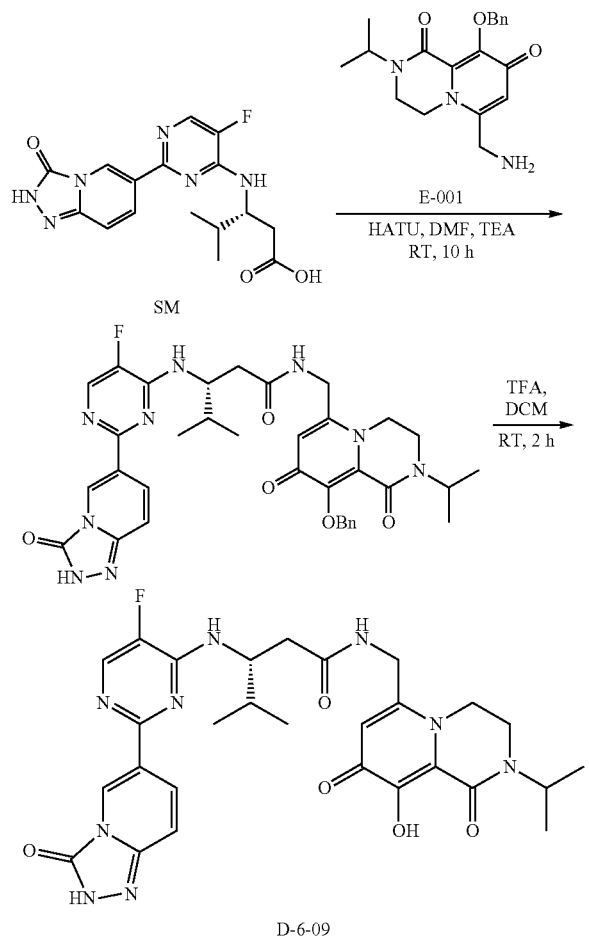

D-6-09

D-6-09 was synthesized in the similar manner as D-3-02-3. Purification by Prep-HPLC afforded D-6-09 (5 mg, 42%) as a brown oil.

(3R)-3-(5-Fluoro-2-(3-oxo-3,8a-dihydro-[1,2,4]triazolo[4,3-a]pyridin-6-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)-4-methylpentanamide

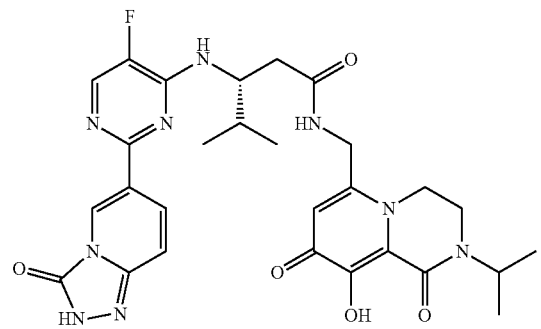 [SMILES: CC(C)[C@@H](CC(=O)NCc1cc(=O)c(O)c2n1CCN(C(C)C)C2=O)Nc1nc(-c2ccc3n[nH]c(=O)n3c2)ncc1F]

D-6-09 was obtained as a brown oil.

Yield: 16%

Mp:

MS (ESI): 594 (M+H)⁺

1H NMR (CD₃OD, 400 Hz):

δ 8.64 (s, 1H), 7.94-8.09 (m, 2H), 7.23 (t, J=9.6 Hz, 1H), 6.56 (s, 1H), 4.91 (s, 1H), 4.72-4.80 (m, 2H), 4.52 (s, 2H), 4.34-4.37 (m, 2H), 3.67 (s, 1H), 2.73-2.80 (m, 2H), 1.95-2.00 (m, 1H), 1.20-1.32 (m, 6H), 1.00-1.12 (m, 6H).

D-6-10:

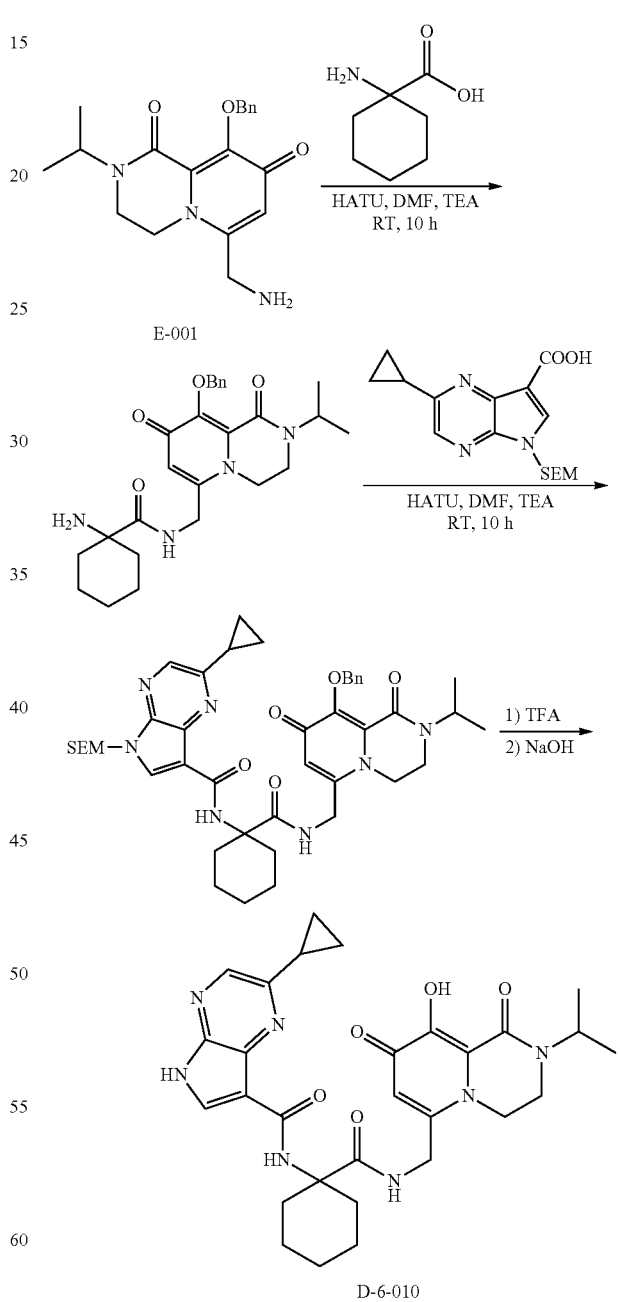

D-6-010

D-6-10 was synthesized in the similar manner as D-6-05. Purification by Prep-HPLC afforded D-6-10 (10 mg, 71%) as a brown solid.

101

2-Cyclopropyl-N-(1-((9-hydroxy-2-isopropyl-1,8-dioxo-2,3,4,8-tetrahydro-1H-pyrido[1,2-a]pyrazin-6-yl)methylcarbamoyl)cyclohexyl)-5H-pyrrolo[3,2-b]pyrazine-7-carboxamide

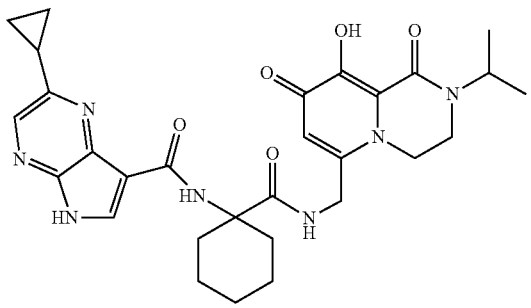 [SMILES: CC(C)N1CCn2c(CNC(=O)C3(NC(=O)c4c[nH]c5ncc(C6CC6)nc45)CCCCC3)cc(=O)c(O)c2C1=O]

D-6-10 was obtained as a brown solid.

Yield: 31%

Mp:

MS (ESI): 562 (M+H)⁺

1H NMR (CD$_3$OD, 400 Hz):

δ 8.92 (s, 1H), 8.39 (s, 1H), 8.21 (s, 1H), 7.07 (s, 1H), 4.94 (s, 1H), 4.45-4.48 (m, 4H), 3.75 (d, J=9.2 Hz, 2H), 2.30-2.38 (m, 4H), 1.91-1.98 (m, 1H), 1.79-1.82 (m, 4H), 1.67-1.70 (m, 2H), 1.29-1.37 (m, 6H), 1.12-1.18 (m, 4H).

D-6-11:

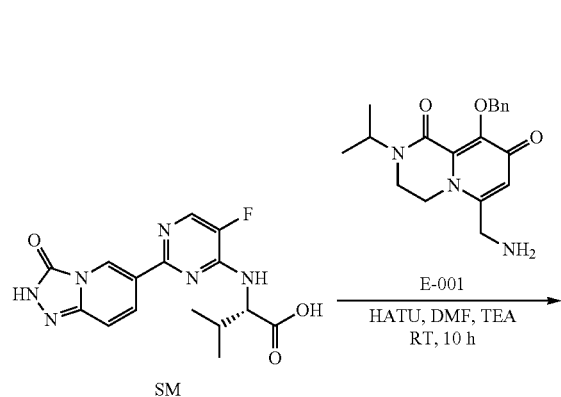

102

-continued

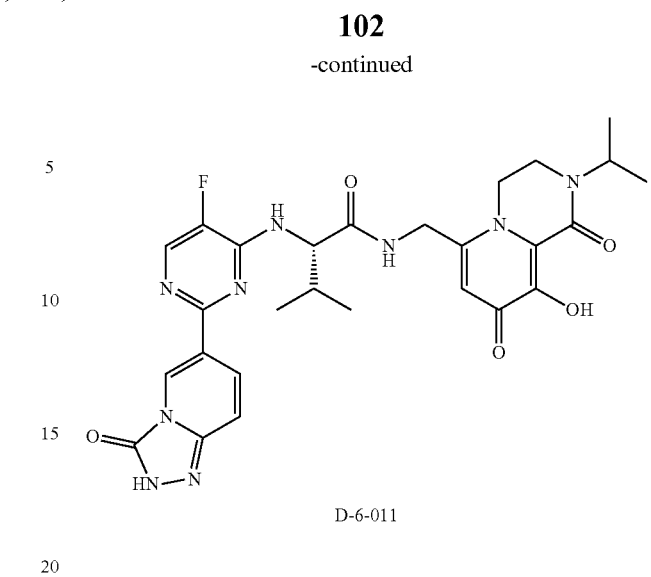

D-6-011

D-6-11 was synthesized in the similar manner as D-3-02-3. Purification by Prep-HPLC afforded D-6-11 (5 mg, 55%) as a brown solid.

(2S)-2-(5-Fluoro-2-(3-oxo-3,8a-dihydro-[1,2,4]triazolo[4,3-a]pyridin-6-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)-3-methylbutanamide

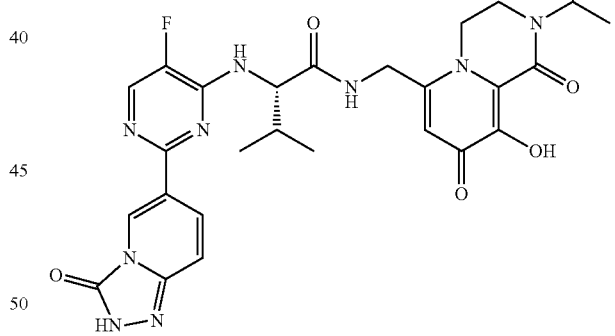

D-6-11 was obtained as a brown solid.

Yield: 29%

Mp:

MS (ESI): 580 (M+H)⁺

1H NMR (CD$_3$OD, 400 Hz):

δ 8.50 (s, 1H), 8.18 (s, 1H), 8.01 (d, J=5.6 Hz, 1H), 7.14 (d, J=9.6 Hz, 1H), 6.59 (s, 1H), 4.85-4.90 (m, 1H), 4.68-4.71 (m, 2H), 4.29-4.33 (m, 2H), 4.17-4.26 (m, 1H), 3.80 (d, J=5.6 Hz, 1H), 3.45-3.50 (m, 1H), 2.25-2.28 (m, 1H), 1.08-1.19 (m, 12H).

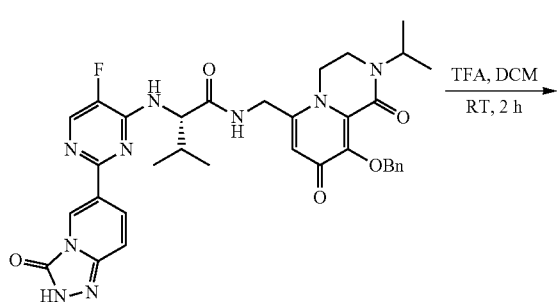

D-6-12:

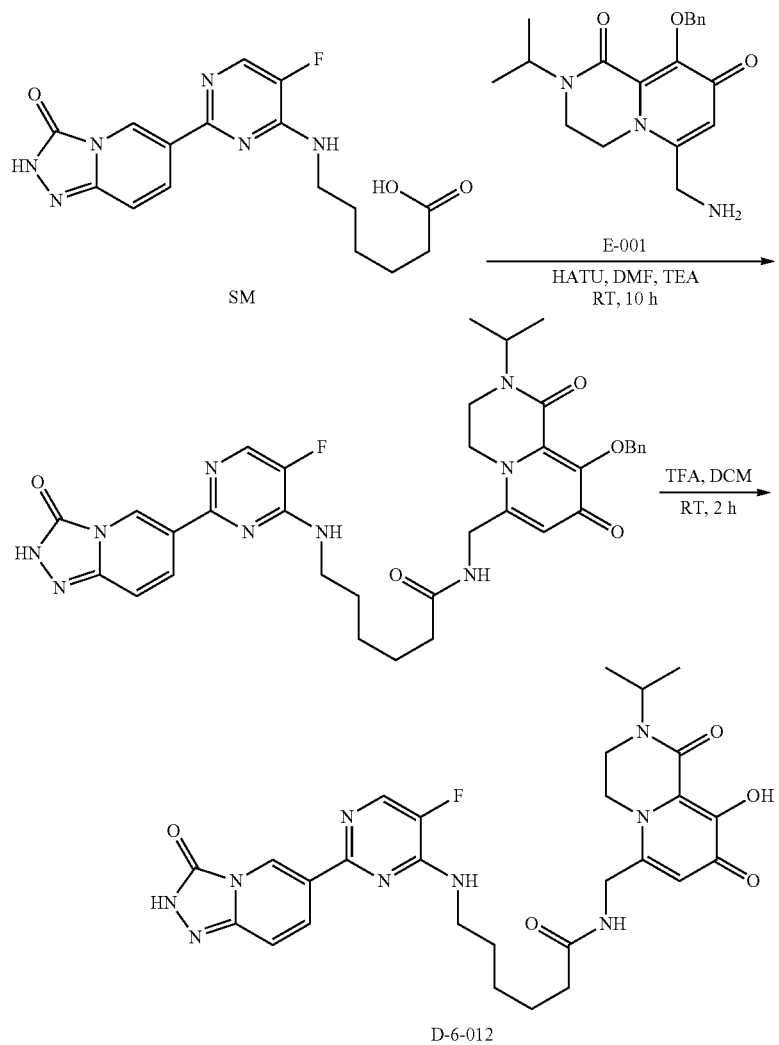

D-6-12 was synthesized in the similar manner as D-3-02-3. Purification by Prep-HPLC afforded D-6-12 (3 mg, 23%) as a yellow solid.

6-(5-Fluoro-2-(3-oxo-3,8a-dihydro-[1,2,4]triazolo[4,3-a]pyridin-6-yl)pyrimidin-4-ylamino)-N-((9-hydroxy-2-isopropyl-1,8-dioxo-2,3,4,8-tetrahydro-1H-pyrido[1,2-a]pyrazin-6-yl)methyl)hexanamide Mp:
MS (ESI): 594 (M+H)$^+$
1H NMR (CD$_3$OD, 400 Hz):
δ 8.73 (s, 1H), 8.08-8.12 (m, 2H), 7.24-7.27 (m, 1H), 6.78 (s, 1H), 4.52 (s, 1H), 4.40-4.42 (m, 2H), 3.75 (s, 2H), 3.64 (t, J=6.8 Hz, 2H), 2.37 (t, J=6.8 Hz, 2H), 1.77 (t, J=6.8 Hz, 4H), 1.49-1.53 (m, 2H), 1.30-1.33 (m, 2H), 1.27 (d, J=6.8 Hz, 6H)

D-6-13:

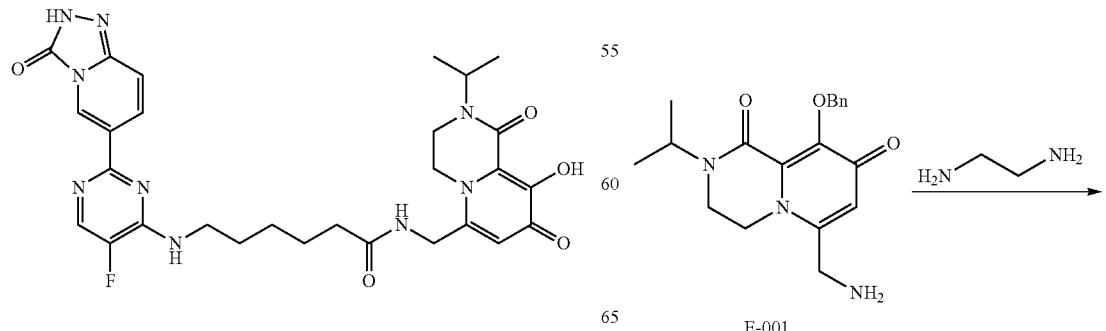

D-6-12 was obtained as a yellow solid.
Yield: 19%

-continued

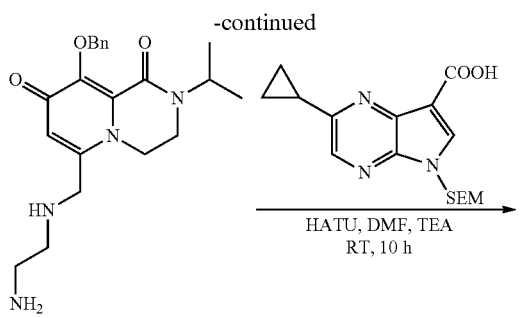

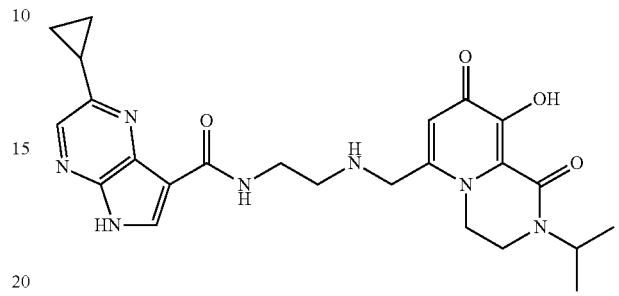

Synthesis of D-6-13-1:
A mixture of E-002 (30.00 mg, 0.1 mmol) in ethane-1,2-diamine (0.5 mL) was stirred at r.t. for 0.5 h. The resultant was purified by Prep-HPLC to afford D-6-13-1 (19.20 mg, 50%) as a white solid.

Synthesis of D-6-13-2:
To a mixture of D-6-02-1 (16.65 mg, 0.05 mmol) and D-6-13-1 (19.20 mg, 0.05 mmol) in DMF (1 mL) was added triethylamine (10.10 mg, 0.10 mmol) and HATU (28.50 mg, 0.075 mmol). The mixture was stirred at r.t. for 10 h. The resultant was purified by Prep-TLC to afford D-6-13-2 (15.70 mg, 45%) as a white solid.

Synthesis of D-6-13:
To a solution of D-6-13-2 (15.70 mg, 0.022 mmol) in dichloromethane (1 mL) was added trifluoroacetic acid (0.5 mL) at 20° C. After 6 h, the mixture was concentrated in vacuo. The residue was suspended in THF (1 mL) and 2.0 M aqueous NaOH (1 mL) added. The mixture was stirred at r.t. for 15 h and then concentrated in vacuo. Water (5 mL) was added and the resultant was extracted with ethyl acetate (2×2 mL). The organic phase was dried and concentrated in vacuo. The residue was purified by Prep-HPLC to give D-6-13 (4.3 mg, 40%) as a pale white solid.

2-Cyclopropyl-N-(2-((9-hydroxy-2-isopropyl-1,8-dioxo-2,3,4,8-tetrahydro-1H-pyrido[1,2-a]pyrazin-6-yl)methylamino)ethyl)-5H-pyrrolo[2,3-b]pyrazine-7-carboxamide (D-6-13)

D-6-13 was obtained as a pale white solid.
Yield: 1%
Mp:
MS (ESI): 480 (M+H)$^+$
$^1$H NMR (CD$_3$OD, 400 Hz):
δ 8.18 (d, J=5.6 Hz, 2H), 6.61 (s, 1H), 4.75 (s, 1H), 4.42 (s, 2H), 4.30-4.31 (m, 2H), 3.80-3.81 (m, 2H), 3.64-3.65 (m, 2H), 3.40-3.41 (m, 2H), 2.21 (s, 1H), 1.17 (d, J=6.8 Hz, 6H), 0.94-0.96 (m, 4H)
$^{13}$C NMR (d$_6$-DMSO, 300 Hz):
D-6-14:

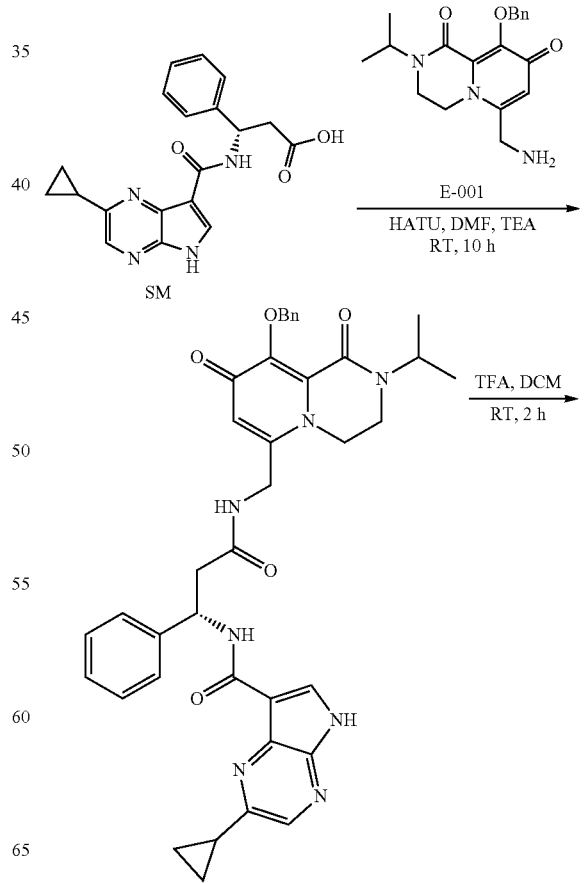

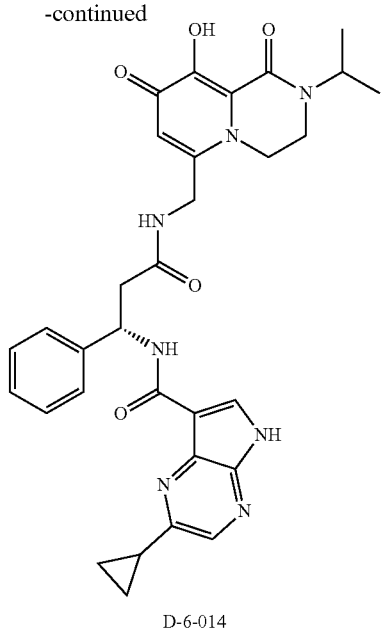

D-6-014

D-6-14 was synthesized in the similar manner as D-3-01-3. Purification by Prep-HPLC afforded D-6-14 (10.00 mg, 46%) as a pale yellow solid.

(S)-2-Cyclopropyl-N-(3-((9-hydroxy-2-isopropyl-1,8-dioxo-2,3,4,8-tetrahydro-1H-pyrido[1,2-a]pyrazin-6-yl)methylamino)-3-oxo-1-phenylpropyl)-5H-pyrrolo[2,3-b]pyrazine-7-carboxamide (D-6-14)

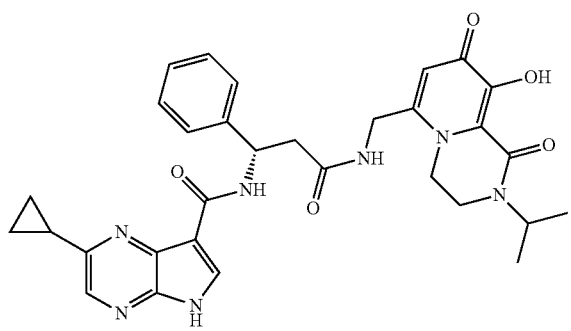 [SMILES: CC(C)N1CCn2c(CNC(=O)C[C@H](NC(=O)c3c[nH]c4ncc(C5CC5)nc34)c3ccccc3)cc(=O)c(O)c2C1=O]

D-6-14 was obtained as a pale yellow solid.

Yield: 1%

Mp:

MS (ESI): 584 (M+H)$^+$ $^1$H NMR (CD3OD, 400 Hz):

δ 8.34 (s, 1H), 8.15 (s, 1H), 7.45 (d, J=7.2 Hz, 2H), 7.36 (t, J=7.2 Hz, 2H), 7.29 (t, J=7.2 Hz, 1H), 6.87 (s, 1H), 5.63 (t, J=4.0 Hz, 1H), 4.85-4.90 (m, 1H), 4.49 (s, 2H), 4.26 (t, J=5.2 Hz, 2H), 3.59-3.65 (m, 2H), 2.92-3.00 (m, 2H), 2.28-2.33 (m, 1H), 1.30-1.32 (m, 1H), 1.27 (d, J=6.8 Hz, 7H), 1.09-1.15 (m, 2H), 0.98-1.02 (m, 1H).

$^{13}$C NMR (d$_6$-DMSO, 300 Hz):

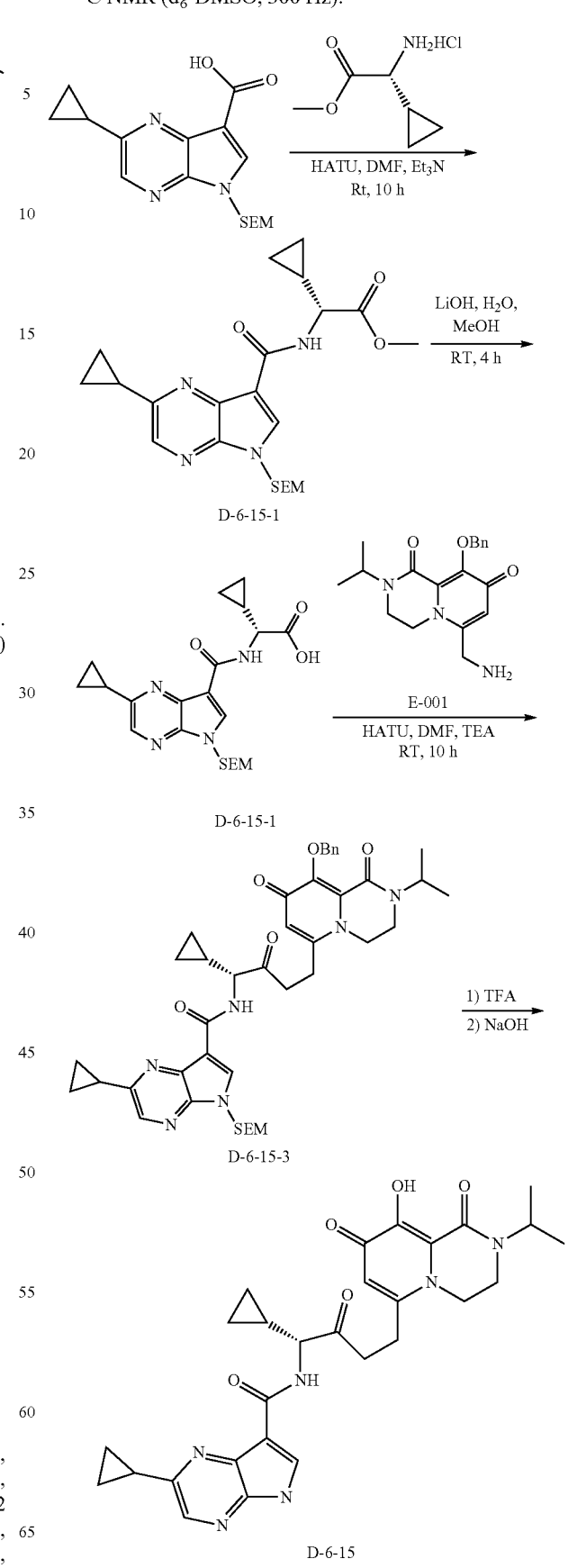

To a mixture of D-6-02-1 (33.30 mg, 0.10 mmol) and (S)-methyl 2-amino-2-cyclopropylacetate hydrochloride (16.51 mg, 0.10 mmol) in DMF (1 mL) was added triethylamine (20.20 mg, 0.20 mmol) and HATU (57.00 mg, 0.15 mmol). The mixture was stirred at r.t. for 10 h. The resultant was purified by Prep-TLC to afford D-6-15-1 (30.00 mg, 67%) as a white solid.

Synthesis of D-6-15-2:

A mixture of D-6-15-1 (30.00 mg, 0.068 mmol) and lithium hydroxide hydrate (5.40 mg, 0.14 mmol) in ethanol (1 mL)) was stirred at r.t. for 4 h. The solvent was removed in vacuo and the resultant was adjusted to pH=5. The formed precipitate was filtered off and dried in vacuo to give D-6-15-2 (20.00 mg, 69%) as a white solid.

Synthesis of D-6-15-3:

To a mixture of D-6-15-2 (20.00 mg, 0.047 mmol) and E-001 (15.86 mg, 0.047 mmol) in DMF (1 mL) was added $K_2CO_3$ (12.84 mg, 0.093 mmol) and HATU (26.51 mg, 0.070 mmol). The mixture was stirred at 30° C. for 5 h. The resultant was purified by Prep-TLC to afford D-6-15-3 (20.00 mg, 57%) as a pale yellow solid.

Synthesis of D-6-15:

To a solution of D-6-15-3 (20.00 mg, 0.027 mmol) in dichloromethane (1 mL) was added trifluoroacetic acid (0.5 mL) at 20° C. After 6 h, the mixture was concentrated in vacuo. The residue was suspended in THF (1 mL) and 2.0 M aqueous NaOH (1 mL) added. The mixture was stirred at r.t. for 15 h and then concentrated in vacuo. Water (5 mL) was added and the resultant was extracted with ethyl acetate (2×2 mL). The organic phase was dried and concentrated in vacuo. The residue was purified by Prep-HPLC to give D-6-15 (8.2 mg, 58%) as a white solid.

(R)-2-cyclopropyl-N-(1-cyclopropyl-2-((9-hydroxy-2-isopropyl-1,8-dioxo-2,3,4,8-tetrahydro-1H-pyrido[1,2-a]pyrazin-6-yl)methylamino)-2-oxoethyl)-5H-pyrrolo[3,2-b]pyrazine-7-carboxamide (D-6-15)

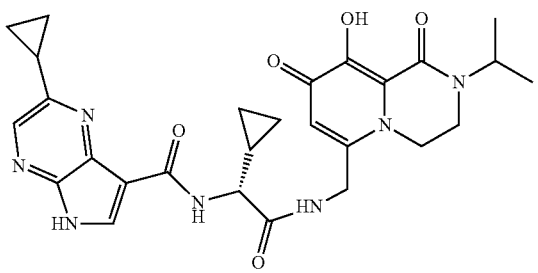 [SMILES: CC(C)N1CCn2c(CNC(=O)[C@H](NC(=O)c3c[nH]c4ncc(C5CC5)nc34)C3CC3)cc(=O)c(O)c2C1=O]

D-6-15 was obtained as a pale white solid.

Yield: 1%

Mp:

MS (ESI): 534 (M+H)$^+$ $^1$H NMR (d$_6$-DMSO, 400 Hz):

δ 12.97 (br, s, 1H), 12.63 (d, J=2.8 Hz, 1H), 8.77-8.85 (m, 2H), 8.49 (s, 1H), 8.28 (d, J=2.8 Hz, 1H), 6.69 (s, 1H), 4.71-4.76 (m, 1H), 4.48-4.53 (m, 2H), 4.32-4.38 (m, 2H), 4.21-4.28 (m, 1H), 3.68 (t, J=5.2 Hz, 2H), 2.31-2.37 (m, 1H), 1.17-1.26 (m, 8H), 1.01-1.13 (m, 3H), 0.50-0.58 (m, 3H), 0.41-0.45 (m, 1H).

$^{13}$C NMR (d$_6$-DMSO, 300 Hz):

2-cyclopropyl-N-(1-cyclopropyl-3-((9-hydroxy-2-isopropyl-1,8-dioxo-2,3,4,8-tetrahydro-1H-pyrido[1,2-a]pyrazin-6-yl)methylamino)-3-oxopropyl)-5H-pyrrolo[2,3-b]pyrazine-7-carboxamide (D-6-16)

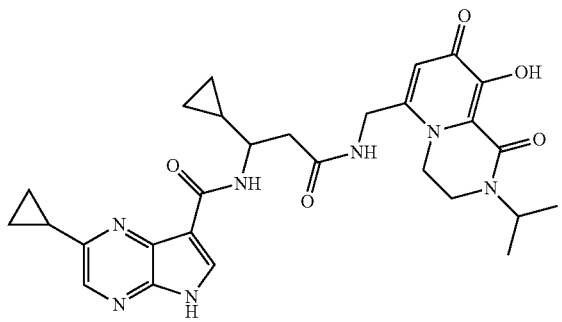 [SMILES: CC(C)N1CCn2c(CNC(=O)CC(NC(=O)c3c[nH]c4ncc(C5CC5)nc34)C3CC3)cc(=O)c(O)c2C1=O]

D-6-16 was obtained as a pale white solid in the same manner as D-6-15.

Yield: 1%

Mp:

MS (ESI): 548 (M+H)$^+$ $^1$H NMR (d$_6$-DMSO, 400 Hz):

δ 13.05 (br, s, 1H), 12.57 (d, J=2.8 Hz, 1H), 8.71 (t, J=5.6 Hz, 1H), 8.38 (s, 1H), 8.35 (d, J=8.8 Hz, 1H), 8.19 (d, J=3.2 Hz, 1H), 6.79 (s, 1H), 4.66-4.73 (m, 1H), 4.45-4.48 (m, 2H), 4.28-4.32 (m, 2H), 3.94 (t, J=8.0 Hz, 1H), 3.62 (d, J=3.2 Hz, 2H), 2.58-2.61 (m, 2H), 2.29-2.34 (m, 1H), 0.98-1.18 (m, 11H), 0.41-0.49 (m, 2H), 0.30-0.34 (m, 1H), 0.22-0.27 (m, 1H)

$^{13}$C NMR (d$_6$-DMSO, 300 Hz).

---

The invention claimed is:

1. A compound having the general formula (V)

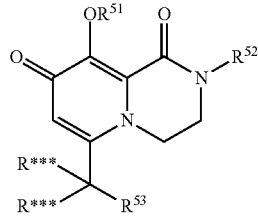

(V)

wherein $R^{51}$ is selected from the group consisting of —H, -(optionally substituted $C_{1-6}$ alkyl) and —C(O)-(optionally substituted $C_{1-6}$ alkyl);

$R^{52}$ is selected from the group consisting of —H, -(optionally substituted $C_{1-6}$ alkyl), —$(CH_2)_q$-(optionally substituted heterocyclyl), —$(CH_2)_q$-(optionally substituted carbocyclyl), —$(CH_2)_p$—$OR^{55}$, and —$(CH_2)_p$—$NR^{56}R^{57}$;

$R^{53}$ is selected from the group consisting of —$R^{54}$ and —$X^{51}R^{54}$;

$R^{54}$ is a bicyclic fused ring system comprising from 10 to 14 ring atoms and 1 to 4 nitrogen atoms as ring atoms, wherein the bicyclic fused ring system can optionally be substituted;

$R^{55}$ is selected from the group consisting of —H, —$C_{1-6}$ alkyl, and —$(CH_2CH_2O)_rH$;

$R^{56}$ is selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

$R^{57}$ is selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

$R^{58}$ is selected from the group consisting of —H and —$C_{1-6}$ alkyl;

$X^{51}$ is -$L_1$-(A-$(L_2)_m)_n$-;

$X^{52}$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, S, SO, and $SO_2$;

$L_1$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$;

$L_2$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$;

A is selected from the group consisting of $(CR^*R^{**})_t$, optionally substituted $C_{3-7}$ carbocyclyl, optionally substituted heterocyclyl having 3 to 7 ring atoms and combinations thereof;

R* is independently for each occurrence selected from the group consisting of —H, -(optionally substituted $C_{1-6}$ alkyl), -(optionally substituted $C_{3-7}$ carbocyclyl), alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

R** is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

or R* and R** can optionally form an optionally substituted $C_{3-7}$ carbocyclyl group or optionally substituted heterocyclyl group having 3 to 7 ring atoms;

R*** is independently for each occurrence —H, a —$C_{1-6}$ alkyl group, or a —$C_{1-6}$ alkyl group which is substituted by one or more halogen atoms;

m is 0 or 1;

n is 0 or 1;

p is 1 to 4;

q is 0 to 4;

r is 1 to 3;

s is 0 to 4; and t is 1 to 6;

wherein the alkyl group can be optionally substituted with one or more substituents which are independently selected from the group consisting of halogen, —CN, —$NR^{56}R^{57}$, —OH, and —O—$C_{1-6}$ alkyl; and wherein the bicyclic fused ring system can be optionally substituted with one or more substituents which are independently selected from the group consisting of (=O), halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms); and wherein the hydrocarbon group, heterocyclyl group, and/or carbocyclyl group can be optionally substituted with one or more substituents which are independently selected from the group consisting of halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms), or a pharmaceutically acceptable salt, racemate, enantiomer, or diastereomer or mixture thereof.

2. The compound according to claim 1, wherein $R^{51}$ is selected from the group consisting of —H and —$C_{1-6}$ alkyl.

3. The compound according to claim 1, wherein $R^{52}$ is selected from the group consisting of —H and —$C_{1-6}$ alkyl.

4. The compound according to claim 1, wherein $R^{53}$ is —$X^{51}R^{54}$.

5. The compound according to claim 1, wherein $R^{54}$ is a bicyclic fused ring system comprising a five-membered ring and a six-membered ring and 1 to 4 nitrogen atoms as ring atoms, wherein the bicyclic fused ring system can optionally be substituted.

6. The compound according to claim 1, wherein $R^{54}$ is selected from the group consisting of

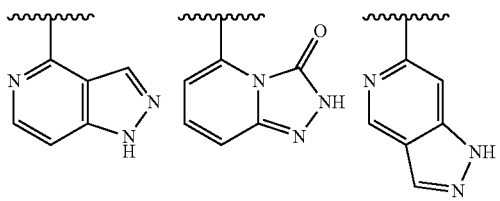

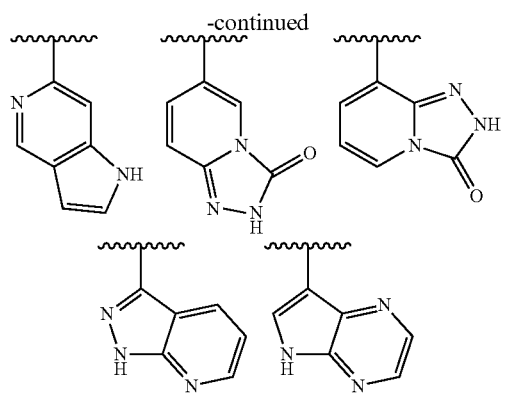

wherein

〜〜〜 indicates the point of attachment to the remainder of the molecule; and wherein the group can be optionally substituted with one or more substituents selected from the group consisting of halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms), preferably one or more substituents selected from the group consisting of halogen, —CN, —$CF_3$, and —$C_{3-7}$ carbocyclyl, more preferably one or more substituents selected from the group consisting of halogen and —$C_{3-7}$ carbocyclyl.

7. The compound according to claim 1, wherein $X^{51}$ is selected from the group consisting of -$L_1$- and -$L_1$-A-$L_2$-;

$L_1$ is selected from the group consisting of $NR^{56}$, $N(R^{56})$C(O), C(O)$NR^{56}$, C(O)O, OC(O), O and (optionally substituted heterocyclyl having 3 to 7 ring atoms)-$NR^{56}$;

$L_2$ is selected from the group consisting of $NR^{56}$, $N(R^{56})$C(O), C(O)$NR^{56}$, C(O)O, OC(O), O and (optionally substituted heterocyclyl having 3 to 7 ring atoms)-$NR^{56}$;

A is selected from the group consisting of $(CR*R**)_r$, cyclohexyl and phenyl;

R* is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

R** is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

or R* and R** can optionally form an optionally substituted $C_{3-7}$ carbocyclyl group or optionally substituted heterocyclyl group having 3 to 7 ring atoms; and t is 1 to 6.

8. A pharmaceutical composition comprising:

a compound according to claim 1, or a pharmaceutically acceptable salt, racemate, enantiomer, or diastereomer or mixture thereof, and one or more pharmaceutically acceptable excipient(s) and/or carrier(s).

9. The pharmaceutical composition according to claim 8, which additionally comprises at least one further medicament which is selected from the group consisting of polymerase inhibitors which are different from the compound having the general formula (V); neuramidase inhibitors; M2 channel inhibitors; alpha glucosidase inhibitors; ligands of another influenza target; antibiotics, anti-inflammatory agents, lipoxygenase inhibitors, EP ligands, bradykinin ligands, and cannabinoid ligands.

10. The compound according to claim 1, wherein the compound exhibits an $IC_{50}$ of less than about 50 μM in a FRET endonuclease activity assay and/or transcription assay.

11. The compound according to claim 2, wherein $R^{52}$ is selected from the group consisting of —H and —$C_{1-6}$ alkyl.

12. The compound according to claim 11, wherein $R^{53}$ is —$X^{51}R^{54}$.

13. The compound according to claim 12, wherein $R^{54}$ is a bicyclic fused ring system comprising a five-membered ring and a six-membered ring and 1 to 4 nitrogen atoms as ring atoms, wherein the bicyclic fused ring system can optionally be substituted.

14. The compound according to claim 13, wherein $R^{54}$ is selected from the group consisting of

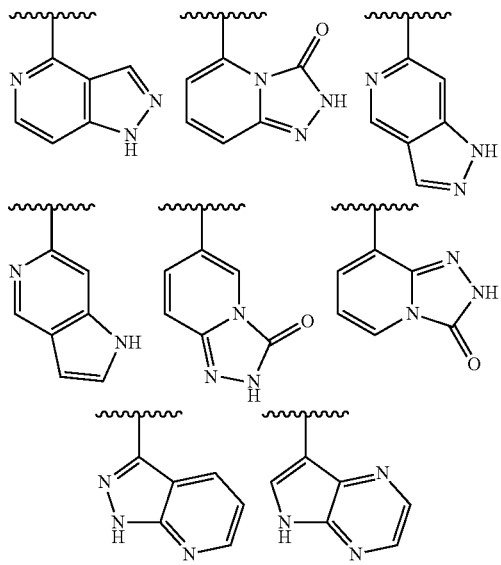

wherein
⁓⁓⁓ indicates the point of attachment to the remainder of the molecule; and
wherein the group can be optionally substituted with one or more substituents selected from the group consisting of halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms), preferably one or more substituents selected from the group consisting of halogen, —CN, —$CF_3$, and —$C_{3-7}$ carbocyclyl, more preferably one or more substituents selected from the group consisting of halogen and —$C_{3-7}$ carbocyclyl.

15. The compound according to claim 14, wherein $X^{51}$ is selected from the group consisting of -$L_1$- and -$L_1$-A-$L_2$-;
$L_1$ is selected from the group consisting of $NR^{56}$, $N(R^{56})$C(O), C(O)$NR^{56}$, C(O)O, OC(O), O and (optionally substituted heterocyclyl having 3 to 7 ring atoms)-$NR^{56}$;
$L_2$ is selected from the group consisting of $NR^{56}$, $N(R^{56})$C(O), C(O)$NR^{56}$, C(O)O, OC(O), O and (optionally substituted heterocyclyl having 3 to 7 ring atoms)-$NR^{56}$;

A is selected from the group consisting of $(CR^*R^{**})_t$, cyclohexyl and phenyl;
R* is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);
R** is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);
or R* and R** can optionally form an optionally substituted $C_{3-7}$ carbocyclyl group or optionally substituted heterocyclyl group having 3 to 7 ring atoms; and
t is 1 to 6.

16. A compound having the general formula (V)

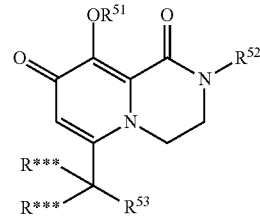

(V)

wherein
$R^{51}$ is selected from the group consisting of —C(O)—R, —C(O)—OR, —PO(OR$^A$)(OR$^B$) or —OC(O)OR, and R, $R^A$ and $R^B$ are independently selected from the group consisting of $C_{1-6}$ alkyl, aryl, or heteroaryl, and the alkyl, aryl, or heteroaryl may be optionally substituted with —OH or O—$C_{1-6}$alkyl;
$R^{52}$ is selected from the group consisting of —H, -(optionally substituted $C_{1-6}$ alkyl), —$(CH_2)_q$-(optionally substituted heterocyclyl), —$(CH_2)_q$-(optionally substituted carbocyclyl), —$(CH_2)_p$—$OR^{55}$, and —$(CH_2)_p$—$NR^{56}R^{57}$;
$R^{53}$ is selected from the group consisting of —$R^{54}$ and —$X^{51}R^{54}$;
$R^{54}$ is a bicyclic fused ring system comprising from 10 to 14 ring atoms and 1 to 4 nitrogen atoms as ring atoms, wherein the bicyclic fused ring system can optionally be substituted;
$R^{55}$ is selected from the group consisting of —H, —$C_{1-6}$ alkyl, and —$(CH_2CH_2O)_rH$;
$R^{56}$ is selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);
$R^{57}$ is selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

$R^{58}$ is selected from the group consisting of —H and —$C_{1-6}$ alkyl;

$X^{51}$ is -$L_1$-(A-($L_2$)$_m$)$_n$-;

$X^{52}$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, S, SO, and $SO_2$;

$L_1$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$;

$L_2$ is selected from the group consisting of $NR^{56}$, $N(R^{56})$ C(O), C(O)$NR^{56}$, O, C(O), C(O)O, OC(O); $N(R^{56})SO_2$, $SO_2N(R^{56})$, $N(R^{56})SO_2N(R^{56})$, S, SO, $SO_2$ and (optionally substituted heterocyclyl having 3 to 7 ring atoms)-$NR^{56}$;

A is selected from the group consisting of (CR*R**)$_p$, optionally substituted $C_{3-7}$ carbocyclyl, optionally substituted heterocyclyl having 3 to 7 ring atoms and combinations thereof;

R* is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

R** is independently for each occurrence selected from the group consisting of —H, -(optionally substituted $C_{1-6}$ alkyl), -(optionally substituted $C_{3-7}$ carbocyclyl), —$C_{1-4}$ alkyl-(optionally substituted $C_{3-7}$ carbocyclyl), -(optionally substituted heterocyclyl having 3 to 7 ring atoms), and —$C_{1-4}$ alkyl-(optionally substituted heterocyclyl having 3 to 7 ring atoms);

or R* and R** can optionally form an optionally substituted $C_{3-7}$ carbocyclyl group or optionally substituted heterocyclyl group having 3 to 7 ring atoms;

R*** is independently for each occurrence —H, a —$C_{1-6}$ alkyl group, or a —$C_{1-6}$ alkyl group which is substituted by one or more halogen atoms;

m is 0 or 1;
n is 0 or 1;
p is 1 to 4;
q is 0 to 4;
r is 1 to 3;
s is 0 to 4; and
t is 1 to 6;

wherein the alkyl group can be optionally substituted with one or more substituents which are independently selected from the group consisting of halogen, —CN, —$NR^{56}R^{57}$, —OH, and —O—$C_{1-6}$ alkyl; and wherein the bicyclic fused ring system can be optionally substituted with one or more substituents which are independently selected from the group consisting of (═O), halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms); and wherein the hydrocarbon group, heterocyclyl group, and/or carbocyclyl group can be optionally substituted with one or more substituents which are independently selected from the group consisting of halogen, —CN, —$CF_3$, —$(CH_2)_s$—$X^{52}$—$R^{58}$, —$C_{1-6}$ alkyl, —$C_{3-7}$ carbocyclyl, —$C_{1-4}$ alkyl-$C_{3-7}$ carbocyclyl, -(heterocyclyl having 3 to 7 ring atoms), and —$C_{1-4}$ alkyl-(heterocyclyl having 3 to 7 ring atoms), or a pharmaceutically acceptable salt, racemate, enantiomer, or diastereomer or mixture thereof.

17. A compound according to claim 16, wherein the R group in $R^{51}$ is selected from the group consisting of $C_{1-6}$ alkyl, phenyl, phenyl-OH and phenyl-$OCH_3$.

18. A pharmaceutical composition comprising a compound according any one of claim 16 or claim 17 or a pharmaceutically acceptable salt, racemate, enantiomer, or diastereomer or mixture thereof, and one or more pharmaceutically acceptable excipient(s) and/or carrier(s).

19. The pharmaceutical composition according to claim 18, which additionally comprises at least one further medicament which is selected from the group consisting of polymerase inhibitors which are different from the compound having the general formula (V); neuramidase inhibitors; M2 channel inhibitors; alpha glucosidase inhibitors; ligands of another influenza target; antibiotics, anti-inflammatory agents, lipoxygenase inhibitors, EP ligands, bradykinin ligands, and cannabinoid ligands.

* * * * *

SEQUENCE LISTING

<160> NUMBER OF SEQ ID NOS: 22

<210> SEQ ID NO 1
<211> LENGTH: 44
<212> TYPE: RNA
<213> ORGANISM: Artificial Sequence
<220> FEATURE:
<223> OTHER INFORMATION: m7G-capped RNA oligonucleotide

<400> SEQUENCE: 1 ggggggaauac ucaagcuaug caucgcauua ggcacgucga agua        44

<210> SEQ ID NO 2
<211> LENGTH: 15
<212> TYPE: RNA
<213> ORGANISM: Artificial Sequence
<220> FEATURE:
<223> OTHER INFORMATION: snatched cap sequence

<400> SEQUENCE: 2
gggggaauac ucaag                                                      15

<210> SEQ ID NO 3
<211> LENGTH: 211
<212> TYPE: RNA
<213> ORGANISM: Artificial Sequence
<220> FEATURE:
<223> OTHER INFORMATION: sequence of de novo synthesized viral mRNA;
      nucleotides 1-212

<400> SEQUENCE: 3
agcaaaagca ggguagauaa ucacucacug agugacauca aaaucauggc gucccaaggc      60
accaaacggu cuuacgaaca gauggagacu gauggagaac gccagaaugc cacugaaauc     120
agagcauccg ucggaaaaau gauuggugga auuggacgau cuacauccaa aaugugcaca     180
gaacuuaaac ucagugauua ugagggacgg u                                    211

<210> SEQ ID NO 4
<211> LENGTH: 120
<212> TYPE: RNA
<213> ORGANISM: Artificial Sequence
<220> FEATURE:
<223> OTHER INFORMATION: sequence of de novo synthesized viral mRNA;
      nucleotides 1425-1545

<400> SEQUENCE: 4
gcggggaguc uucgagcucu cggacgaaaa ggcagcgagc ccgaucgugc cuuccuuuga 60
caugaguaau gaaggaucuu auuucuucgg agacaaugca gaggaguacg acaauuaaag 120

<210> SEQ ID NO 5
<211> LENGTH: 21
<212> TYPE: DNA
<213> ORGANISM: Artificial Sequence
<220> FEATURE:
<223> OTHER INFORMATION: Label Extender 1 (LE1)

<400> SEQUENCE: 5 ccccttatg agttctcgtt t 21

<210> SEQ ID NO 6
<211> LENGTH: 26
<212> TYPE: DNA
<213> ORGANISM: Artificial Sequence
<220> FEATURE:
<223> OTHER INFORMATION: Blocking Probe 1 (BP1)

<400> SEQUENCE: 6
tcgtcccatc tattagtgag tgactc 26

<210> SEQ ID NO 7
<211> LENGTH: 22
<212> TYPE: DNA
<213> ORGANISM: Artificial Sequence
<220> FEATURE:
<223> OTHER INFORMATION: Capture Extended 1 (CE1)

<400> SEQUENCE: 7
actgtagttt tagtaccgca gg                                             22

<210> SEQ ID NO 8
<211> LENGTH: 21
<212> TYPE: DNA
<213> ORGANISM: Artificial Sequence
<220> FEATURE:
<223> OTHER INFORMATION: Capture Extender 2 (CE2)

<400> SEQUENCE: 8
gttccgtggt ttgccagaat g                                              21

<210> SEQ ID NO 9
<211> LENGTH: 24
<212> TYPE: DNA
<213> ORGANISM: Artificial Sequence
<220> FEATURE:
<223> OTHER INFORMATION: Blocking Probe 2 (BP2)

<400> SEQUENCE: 9
cttgtctacc tctgactacc tctt                                           24

<210> SEQ ID NO 10
<211> LENGTH: 19
<212> TYPE: DNA
<213> ORGANISM: Artificial Sequence
<220> FEATURE:
<223> OTHER INFORMATION: Capture Extender 3 (CE3)

<400> SEQUENCE: 10
gcggtcttac ggtgacttt                                                 19

<210> SEQ ID NO 11
<211> LENGTH: 20
<212> TYPE: DNA
<213> ORGANISM: Artificial Sequence
<220> FEATURE:
<223> OTHER INFORMATION: Capture Extender (CE4)

<400> SEQUENCE: 11
agtctcgtag gcagcctttt                                                20

<210> SEQ ID NO 12
<211> LENGTH: 21
<212> TYPE: DNA
<213> ORGANISM: Artificial Sequence
<220> FEATURE:
<223> OTHER INFORMATION: Blocking Probe 3 (BP3)

<400> SEQUENCE: 12
tactaaccac cttaacctgc t                                              21

<210> SEQ ID NO 13
<211> LENGTH: 24
<212> TYPE: DNA
<213> ORGANISM: Artificial Sequence
<220> FEATURE:
<223> OTHER INFORMATION: Blocking Probe 4 (BP4)

<400> SEQUENCE: 13
aagatgtagg tttacacgtg tctt                                           24

<210> SEQ ID NO 14
<211> LENGTH: 26
<212> TYPE: DNA
<213> ORGANISM: Artificial Sequence

```
<220> FEATURE:
<223> OTHER INFORMATION: Capture Extender 5 (CE5)

<400> SEQUENCE: 14
gaatttgagt cactaatact ccctgc                                          26

<210> SEQ ID NO 15
<211> LENGTH: 20
<212> TYPE: DNA
<213> ORGANISM: Artificial Sequence
<220> FEATURE:
<223> OTHER INFORMATION: Capture Extender 6 (CE6)

<400> SEQUENCE: 15
cccctcagaa gctcgagagc                                                 20

<210> SEQ ID NO 16
<211> LENGTH: 19
<212> TYPE: DNA
<213> ORGANISM: Artificial Sequence
<220> FEATURE:
<223> OTHER INFORMATION: Capture Extender 7 (CE7)

<400> SEQUENCE: 16
ctgcttttcc gtcgctcgg                                                  19

<210> SEQ ID NO 17
<211> LENGTH: 20
<212> TYPE: DNA
<213> ORGANISM: Artificial Sequence
<220> FEATURE:
<223> OTHER INFORMATION: Capture Extender 8 (CE8)

<400> SEQUENCE: 17
gctagcacgg aaggaaactg                                                 20

<210> SEQ ID NO 18
<211> LENGTH: 27
<212> TYPE: DNA
<213> ORGANISM: Artificial Sequence
<220> FEATURE:
<223> OTHER INFORMATION: Capture Extender 9 (CE9)

<400> SEQUENCE: 18
tactcattac ttcctagaat aaagaag                                         27

<210> SEQ ID NO 19
<211> LENGTH: 22
<212> TYPE: DNA
<213> ORGANISM: Artificial Sequence
<220> FEATURE:
<223> OTHER INFORMATION: Blocking Probe 5 (BP5)

<400> SEQUENCE: 19
cctctgttac gtctcctcat gc                                              22

<210> SEQ ID NO 20
<211> LENGTH: 27
<212> TYPE: DNA
<213> ORGANISM: Artificial Sequence
<220> FEATURE:
<223> OTHER INFORMATION: Label Extender 2 (LE2)

<400> SEQUENCE: 20
gatgattttt ttttttttt ttttttt                                          27
```

```
<210> SEQ ID NO 21
<211> LENGTH: 226
<212> TYPE: RNA
<213> ORGANISM: Artificial Sequence
<220> FEATURE:
<223> OTHER INFORMATION: sequence of de novo synthesized viral mRNA;
      nucleotides 1 to 212 with capped primer

<400> SEQUENCE: 21
gggggaauac ucaagagcaa aagcagggua gauaaucacu cacugaguga caucaaaauc     60
auggcguccc aaggcaccaa acggucuuac gaacagaugg agacugaugg agaacgccag    120
aaugccacug aaaucagagc auccgucgga aaaaugauug guggaauugg acgauucuac    180
auccaaaugu gcacagaacu uaaacucagu gauuaugagg gacggu                    226

<210> SEQ ID NO 22
<211> LENGTH: 141
<212> TYPE: RNA
<213> ORGANISM: Artificial Sequence
<220> FEATURE:
<223> OTHER INFORMATION: sequence of de novo synthesized viral mRNA;
      nucleotides 1425-1545 with polyA tail

<400> SEQUENCE: 22
gcggggaguc uucgagcucu cggacgaaaa ggcagcgagc ccgaucgugc cuuccuuuga     60
caugaguaau gaaggaucuu auuucuucgg agacaaugca gaggaguacg acaauuaaag    120
aaaaaaaaaa aaaaaaaaaa a                                              141
```